(12) United States Patent
Pilarski et al.

(10) Patent No.: US 7,504,212 B2
(45) Date of Patent: Mar. 17, 2009

(54) CANCER MONITORING AND THERAPEUTICS

(75) Inventors: Linda Pilarski, Spring Lake (CA); Sophia Adamia, Edmonton (CA); Andrew Belch, Edmonton (CA); Tony Reiman, St. Albert (CA); Mary Hay, Edmonton (CA)

(73) Assignee: Governors of the University of Alberta, Edmonton (CA)

( * ) Notice: Subject to any disclaimer, the term of this patent is extended or adjusted under 35 U.S.C. 154(b) by 0 days.

(21) Appl. No.: 10/672,399

(22) Filed: Sep. 25, 2003

(65) Prior Publication Data

US 2005/0003368 A1    Jan. 6, 2005

Related U.S. Application Data

(60) Provisional application No. 60/472,401, filed on May 22, 2003.

(51) Int. Cl.
  *C12Q 1/68*   (2006.01)
  *G01N 33/574* (2006.01)
  *A61K 31/70*  (2006.01)

(52) U.S. Cl. .............................. 435/6; 514/44; 435/7.23

(58) Field of Classification Search ............... 435/6, 435/7.1
    See application file for complete search history.

(56) References Cited

U.S. PATENT DOCUMENTS 6,303,343 B1 * 10/2001 Kopf-Sill .................. 435/91.1
6,812,339 B1 * 11/2004 Venter et al. ............. 536/24.31

OTHER PUBLICATIONS

Anthony Calabro, Martin M. Oken, Vincent C. Hascall, and Anna M. Masellis Characterization of hyaluronan synthase expression and hyaluronan synthesis in bone marrow mesenchymal progenitor cells: . . . Blood, vole 100, p. 2578-2585, 2002.*

Desikan R, Li Z, Jagannath S. Waldenstrom's macroglobulinaemia: current therapy and future approaches. BioDrugs. 2002;16(3):201-207.*

Adamia S, Crainie M. Kriangkum J, Mant MJ, Belch AR, Pilarski LM.Abnormal expression of hyaluronan synthases in patients with Waldenstrom's macroglobulimenia. Semin Oncol. Apr. 2003;30(2):165-8.*

Raje N, Anderson KC, Multiple myeloma. Curr Treat Options Oncol. Apr. 2000;1(1):73-82.*

* cited by examiner

*Primary Examiner*—Larry R. Helms
*Assistant Examiner*—Lei Yao
(74) *Attorney, Agent, or Firm*—Craig K. Sherburne

(57) ABSTRACT

Provided for are three novel isoenzyme variants of the human Hyaluronan Synthase gene, HAS1Va, HAS1Vb, and HAS1Vc. Also provided is a method for assessing disease, or susceptibility to disease, in a patient; in which a cell or sample of a cell population is mixed with at least one compound which specifically binds to HAS1Va, HAS1Vb, HAS1Vc or HAS2 isoenzyme or isoenzyme variant genomic mRNA transcript or products arising therefrom; and methods of treatment.

5 Claims, 22 Drawing Sheets

The x-axes represent molecular size (bp) of PCR product and the y-axes Relative Fluorescent units (RFU). ———, ——— internal size standard peaks; ———— PCR product peaks.

The x-axes represent molecular size (bp) of PCR product and the y-axes Relative Fluorescent units (RFU). ▬▬ internal size standard peaks; ▬▬▬ PCR product peaks.

MM B cells 48h after culturing

Particle Exclusion Assay in combination with HA staining

Sorted MM B cells → Fixation with 2% PFA → Indirect HA staining → PEA

MM B 48h after culturing

HABP Streptavidin Alexa 633    Streptavidin Alexa 633

HAS 1Vb

HAS 1Vb - 361 aa - 39.52 KD

HAS 1Vc

HAS 1Vc - 354/381 aa - ~36 KD

Kaplan-Meier survival plots for patients with Multiple Myeloma. p=0.03, using the log rank test.

Kaplan-Meier survival plots for patients with Multiple Myeloma. p=0.03, using the log rank test.

Kaplan-Meier survival plots for patients with Multiple Myeloma. p=0.002, using the log rank test.

Kaplan-Meier survival plots for patients with Multiple Myeloma. p=0.02, using the log rank test.

204-321aa - Glycosyl transferase   231-382aa - Chitin

*Weigel, 1997; Heldermon et al., 2001*

Secondary mRNA structure predicted

HAS1FL

HAS1Vc

HAS1Vc

HAS1Vb

HAS1Va

RT-PCR product analysis on microfluidic chip.

Negative Control

15 cycles

20 cycles

FIG 18 splice sites on intron 4 (fragment)

```
   1  ■taagctgag gggaccaggt ggtcgg■at gtgtggaggc caatgaatat cctagcgtgt gtgcatgctg agagttctcc aaatccaaag
  91  taactcacca gacaatgggc tctatccagt gagactttag aggagagagg aggataccat aatgggcaga gggccattt gcattgagcc
 181  aatggactct accaagtgag atattaggga agaggggaag atactataag ggacaaggct ggcatttgca ttgaaccatg gaatgcggtg
 271  aacctcacca agagaggcaa g■gagggta ■agaattcca cctagaattg agatagg■g agttgtcct gtcatggaga ccaaggtagc
 361  acagtgggga gtgaagtagg aaggcaaga gacaaatgga tagagtggga tctaactagt gagagagcca cggagaaaga aacaagtgag
 451  agagaggag ccctgaact cta■aagtt cttcaagaga agacaagtaa ttccatgaga ctccagggag gatgatctag accaagtgaa
 541  gttcagggga gagtgatttc tgcaaagcca ggtccactga aataccccaga ggaaacttgg gataatccag gggaatccat gcattaattc
 631  actcaacaaa tattcactag gtgcctagaa tgtttaagct gcggggatac agcaataggc agcaggaca ccaattgatt acatcagttg
 721  gggagacaca caagaaataa ataagtagaa catacagtat gttcatgata tgtgttatgg agataaataa tgccggcaa gggtggtgga
 811  taggaagttt tgggggttggg gtgaagtgt taagtgggagt gcctga■g■ ggatgggct caaggctgag aatagtgtgg ctggagcact
 901  gaactgggg agtattagga gagcaggatg gagagttaag gagtgtcca ctcatgaaag gcttatagt ctaaggactc tgactaagat
 991  gaggagca tgggaggtt ttaagcagag aagtgacacg ttgtaatgg atccctctgg cagccgtttt gggtacagac tacaaaagc
1081  aaggtccgaa gcaggaggc cactgaggat gtgcctagaa acaggggaag gagtctggac actgtcaagt aatgcccagg atctcctct
1171  tgtgtggggct tggctggaaa ccatgcaggg attgattaat gatgtctgcc acaaaacagg aaggaggcct gatggtcc ttgagaagtt
1261  ctaatacata gactaccctg ggtagcaacc acaccccatct tgcctcctcc tat■ggcct gccagtaata ■aagcatgg tagtattagt
1351  aatatgttag tgatagtatt agtaata■g tcagtaacca acatgatatt agtaacagca ataagtaatgg taacagcaat agtacatgta
1441  aaaacgtag tagctaacat ttattgagca aatactatct actgtccta agcacttggc gttaatttc agcctggagt gcaggggcac gatcatgct
1531  ttgtcttatg agagccttt tttttttctt ■■atagagtc ttgctgtgtt gtccagggctc agggctgagt gggactacag gccaccacgc ccgctaatt
1621  cactgcagcc tcaaactcct gacctcaagt gattccccca tctccagcctc tgttgcctag gctgatctca aactcttagc cccctagc cccctacct
1711  ttttttttt tttttttttt ttagagatgg ggtctcacta tgttcctag gctgatctca atggtgctt attattat ttatttattt attagt■g■a
1801  cagccctta agtgctggg attacaggca catcccacc atggtgctt agcctcccaa agtgctggga ttacaggagt gagccaccgc
1891  gatggggct tgctatgttg cccaggctgg tcttgaactc agcctcccca cttatcccct agcctcccaa agtgctggga ttacaggagt gagccaccgc
1981  gtccaggct aggaaccatt atccaccta ttctacacat ggaacactg aggctagag aggttaagaa actgccccc agtgccgtc
2071  cacagtggtc atttctgcct cc■a
```

■ donor splice sites (7) score (0.96-0.98)  ■ acceptor splice sites (5) score (0.98-1)

CANCER MONITORING AND THERAPEUTICS

CROSS REFERENCE TO RELATED APPLICATIONS

This application claims priority to U.S. provisional application Ser. No. 60/472,401, filed May 22, 2003, the disclosure of which is incorporated by reference.

FIELD OF THE INVENTION

The invention relates to methods of diagnosis of disease based upon novel variants of the Hyaluonic Acid Synthase gene; methods for diagnosis of predisposition to disease; methods for treatment of disease; and methods for isolation and purification of novel variants of the mammalian Hyaluronic Synthase Genes.

BACKGROUND OF THE INVENTION

Current models of carcinogenesis describe cancer as a progression of genetic mutations in a tumour cell mass and these models have contributed to the discoveries of many tumour suppressor genes and potential oncogenes (Hanahan D. et al. *Cell* 100:57 (2000)). The progression of genetic mutations can arise from a genetic instability in the cell leading to a loss in replication fidelity, genetic translocations or loss of genetic material. Solid tumours, however, are more than clonal expansions of tumour cells; tumours are heterogeneous and have a complex structure, with Bissell et al. describing a tumour as a unique "organ" formed by "tissues" (Bissell, M. J. et al. *Nat Rev Cancer* 1:46 (2001)). The cells composing these tissues interact with each other and with other types of cells, and exchange information through cell-cell interactions or through interactions with cytokines and the extracellular matrix (ECM) (Bissell, M. J. et al. *Nat Rev Cancer* 1:46 (2001)). Playing an important role in these interactions, and possibly playing a role in proliferative disease progression as taught in the art and as discovered by the inventors and herein disclosed, is hyaluronic acid (hereinafter "HA").

HA, a non-sulfated negatively charged glycosaminoglycan, is composed of repeating disaccharide units of D-glucorinic acid and N-acetylglucosamine. HA is completely biodegradable by a natural catalytic pathway and is widely distributed in all connective tissue of eukaryotes and in the capsules of group A and C streptococci (Laurent, T. C. et al. *FASEB J*. 6:2397 (1992)). HA is involved in many biological processes such as embryogenesis, cell adhesion and motility, cell growth and differentiation, and angiogenesis (Baneijee, S. D. et al. *J Cell Biol* 119:643 (1992); Bourguignon, L. Y. et al. *J Biol Chem* 272:27913 (1997); Lees, V. C. et al. *Lab Invest* 73:259 (1995); West, D. C. et al. *Science* 228:1324 (1985)).

HA, which is widely distributed in all connective tissue of eukaryotes, is a water-like molecule; because of this characteristic HA has been regarded as an ideal lubricant of the joints and has been successfully used in the treatment of patients with arthritis (Radin, E. L. et al. *Nature* 228:377 (1970)), where HA forms a layer between the cartilage surfaces in joints and protects them from frictional damage (Hlavacek, M., *J Biomech* 26:1151 (1993)). In arthritis, the mechanism forming protective HA layers is disrupted since the concentration of HA itself and molecular weight of the HA molecules are low as compared to normal tissues (Hlavacek, M., *J Biomech* 26:1151 (1993)). Depletion of HA results in degradation of the ECM and promotes osteoarthritis, a degenerative disease of articular cartilage.

Dramatically increased HA-rich matrix formation has been observed around proliferating and migrating cells during morphogenesis, regeneration and healing. High amounts of HA molecules are synthesized:

1) prior to the mesenchymal cell differentiation and throughout embryonic development, the condensation and differentiation of the mesenchymal cells are accompanied by the spatial distribution of HA in the different regions of the limb bud (Kosher, R. A. et al. *Cell Differ* 17:159 (1985); Kosher, R. A. et al. *Nature* 291:231 (1981); Kosher, R. A. et al. *J Embryol Exp Morphol* 56:91 (1980));
2) during brain development around proliferating and migrating neuronal cells, (Verna, J. M. et al. *Int J Dev Neurosci*. 7:389 (1989)); and
3) during formation of heart valves when cushion cells migrate from the endocardium to the myocardium (Camenisch, T. D. et al. *J Clin Invest* 106:349 (2000)).

HA matrices are removed from the cells after final differentiation at the end of morphogenetic events (Gakunga, P. et al. *Development* 124:3987 (1997)). Throughout morphogenesis HA creates hydrated pathways, thus facilitating free movement of the cells in this microenvironment (Gakunga, P. et al. *Development* 124:3987 (1997)). HA molecules are conducive to cell proliferation and migration, preventing differentiation of cells until sufficient number and appropriate positioning of cells is established, which is essential for the formation of tissues and/or organs (Gakunga, P. et al. *Development* 124:3987 (1997)). In addition, the formation of hydrated pathways by HA molecules is closely associated with the surface of different types of cells, and these associations promote cell adhesion and aggregation (Sionov, R. V. et al. *Adv Cancer Res* 71:241 (1997); Lee, V. et al. *J Cell Biochem* 79:322 (2000)).

The motility of malignant cells is mediated through interactions with HA, which is an important extracellular matrix molecule (Docherty, R. et al. *J Cell Sci* 92:263 (1989); Ropponen, K. et al. *Cancer Res* 58:342 (1998); Ruoslahti, E. *J Biol Chem* 264:13369 (1989); Sherman, L. et al. *Curr Opin Cell Biol* 6:726 (1994); Zhang, W. et al. *Biochem J* 349:91 (2000)). High or very low levels of HA in the serum of patients with multiple myeloma (MM) correlate with dramatically reduced median survival of these patients (Dahl, I. M. et al. *Blood* 93:4144 (1999b)). Moreover, HA mediates survival of MM cell lines against dexamethasone-induced apoptosis through IL-6-dependent and -independent autocrine pathways (Vincent, T. et al. *Br J Haematol* 121:259 (2003)). HA also increases intracellular $Ca^{2+}$ levels by binding to CD44, suggesting that HA may activate intracellular signaling through activation of protein kinase C (Fraser, S. P. *FEBS Lett* 404:56 (1997); Liu, D. et al. *Cell Immunol* 174:73 (1996); Milstone, L. M. et al. *J Cell Sci* 107:3183 (1994)). Also secretion of HA is stimulated by growth factors which activate classical and novel isoform (PKCa) of PKC (Anggiansah, C. L. et al. *J Physiol* 550:631 (2003)). In addition to its role as an ECM and signaling molecule, HA plays a significant role in the process of mitosis and in the maintenance of cell shape or volume (DeAngelis, P. L., *Cell Mol Life Sci* 56:670 (1999); Evanko, S. P. et al. *Arterioscler Thromb Vasc Biol* 19:1004 (1999)).

Biochemical and cell biological studies suggest that HA is synthesized at the inner face of the plasma membrane and is immediately extruded into the extracellular matrix (ECM) where HA molecules are assembled and form a pericellular coat around the cell plasma membrane (Weigel, P. H. et al.

Biol Chem 272:13997 (1997)). The manner of the synthesis of HA molecules is unique and differs from the synthesis of other glycosaminoglycans that occurs at the golgi, with finished products exported to the cell surface by proteins. In addition to extracellular HA, an intracellular HA derived from an intracellular pool in the cell has also been detected (Evanko, S. P. et al. *Histochem Cytochem* 47:1331 (1999)). The production of HA is stimulated by phobol esters, the transforming growth factor beta (TGF-β), and the platelet-derived growth factor (PDGF) family, by activation of protein kinase C and cAMP (Honda, A et al. *Biochem J* 292:497 (1993); Pienimaki, J. P. et al. *J Biol Chem* 276:20428 (2001); Suzuki, M. et al. *Biochem J* 307:817 (1995)).

Hyaluronan synthase (HAS), is an integral membrane protein which mediates 7 distinct functions in order to assemble and translocate HA molecules through the cell plasma membrane. The HAS protein is associated with malignant cell transformation (Banerjee, S. D. et al. *J Cell Biol* 119:643 (1992); Suzuki, M. et al. *Biochem J* 307:817 (1995)). The activation of HAS and consequently HA production strongly correlates with the transforming activity of v-src (Sohara, Y. et al. *Mol Biol Cell* 12:1859 (2001)). Furthermore, tumour-specific activation of cell migration is mediated by two parallel pathways the Ras-MAPK and the PI3K-Akt pathway (Sohara, Y. et al. *Mol Biol Cell* 12:1859 (2001)).

Heldermon et al. proposed an updated topological structure of *Streptococcus pyogenes* hasA (sphasA) (Heldermon, C. D. et al. *Glycobiology* 11:1017 (2001)). Their proposed structure includes four transmembrane domains (TDM), two extracellular loops, two membrane-associated regions, an intracellular central loop, and intracellular amino and carboxyl terminals. Due to their extensive primary sequence identity, it has been proposed that eukaryotic and bacterial HAS proteins have the same topological organization and they belong to the same class, class 1, of HAS protein family (Table 1) (DeAngelis, P. L., *Cell Mol Life Sci* 56:670 (1999)). The eukaryotic HAS is 40% larger than bacterial HAS and its topology includes an additional trasmembrane domain and an extracellular loop.

TABLE 1

Classes of HAS proteins (DeAngelis, P. L., Cell Mol Life Sci 56:670 (1999))

| | Class I | Class II |
|---|---|---|
| Members | SpHas, seHas, cvHas, xlHas, vertebrate HAS1, 2, 3 | PmHas |
| Polypeptide Size | 417-588 residues | 972 residues |
| Topology | multiple pass, integral membrane protein | soluble with a docking segment for membrane partner |

Examination of the hydrophobic domains of HAS isoenzyme variants have shown the existence of cysteine residues in the amino acid sequences of the central domain (Heldermon, C. et al. *J Biol Chem* 276:2037 (2001)). Modification of these cysteine residues changes the enzymatic activities of the HAS proteins (Heldermon, C. et al. *J Biol Chem* 276:2037 (2001); Pummill, P. E. et al. *J Biol Chem* 278:19808 (2003)). Recently, it has been shown that single amino acid mutation introduced on the HAS protein alters the size of the HA molecules, specifically the size of HA chain can be either reduced or increased (Pummill, P. E. et al. *J Biol Chem* 278: 19808 (2003)). The serine, tyrosine, and cysteine(s) which are responsible for this process are conserved and located either on the central loop (tyrosine, and cysteine(s)) while serine is part of the TMD of the protein. A significant number of protein kinase C phosphorylation sites are predicted within the intracellular loop of the HAS protein suggesting that HAS activation is perhaps regulated by direct phosphorylation, and suggesting potential sites for therapeutic attack.

Three isoenzymes of HAS: HAS1, HAS2, and HAS3; have been detected in humans thus far. The related but separate genes of the HASs, which share at least one or two exon-intron boundaries and 55-71% amino acid sequence identity, are located on different chromosomes (hCh19-HAS1, hCh8-HAS2, hCh16-HAS3) and encode three different proteins with distinct enzymatic properties (Itano, N. et al. *J Biol Chem* 274:25085 (1999); Spicer, A. P. et al. *Genomics* 41:493 (1997)). Recently two variants of HAS3, HAS3v1 and HAS3v2, have been reported (NCBI database). The similarities of gene structure suggest that these genes might have arisen by a gene duplication event (Spicer, A. P. et al. *Genomics* 41:493 (1997)). Also localization of HASs in different chromosomes suggests differential expression of these genes and not completely similar functions. Each isoform of the HAS protein synthesizes different sizes of HA molecules with different functions. HAS3 synthesizes shorter forms of HA molecules compared to HAS1 and HAS2, both of which produce longer molecules of HA. The HAS1, which synthesizes high-molecular weight HA, may maintain a low, basal level of HA. HAS2 is involved in embryonic and cardiac cushion morphogenesis and subsequent development through cell migration and invasion (Camenisch, T. D. et al. *J Clin Invest* 106:349 (2000)). This form of HA induces cell proliferation and activates cell signaling cascades which stimulate angiogenesis.

Overexpression of HAS proteins and subsequent overproduction of HA molecules promotes growth and/or metastatic development in fibrosarcoma, prostate and mammary carcinoma. However, the removal of the HA matrix from a migratory cell membrane inhibits cell movement, as has been demonstrated by Baneijee et al. and Evanko et al. (Banedji, S. et al. *J Cell Biol* 144:789 (1999); Evanko, S.P. et al. *Arterioscler Thromb Vasc Biol* 19:1004 (1999)). HAS proteins, particularly the HAS2 isoenzyme, which is involved in embryonic and cardiac cushion morphogenesis and subsequent development through cell migration and invasion, appear to facilitate abnormal cell proliferation and the activation of cell signaling cascades that stimulate angiogenesis and may promote tumour progression (Lees, V.C. et al. *Lab Invest* 73:259 (1995); West, D. C. et al. *Science* 228:1324 (1985)).

HA overproduction by cushion cells not only provides a substrate for cardiac cell migration but also influences the transformation of these cells into a motile phenotype, suggesting a significant role in oncogenesis (Lees, V. C. et al. *Lab Invest* 73:259 (1995); Li, H. et al. *Int J Oncol* 17: 927 (2000)). HA is produced in large quantities by cells undergoing mitosis as well. It facilitates cell rounding and is involved in the post-mitotic separation of daughter cells (Evanko, S. P. et al. *J Histochem Cytochem* 47:1331 (1999); Tammi, R. et al. *Exp Cell Res* 195:524 (1991)). The activation of HAS enzymes appears to be essential for these events. The expression of the antisense of HAS2 and/or HAS3 in the aggressive prostate adenocarcinoma PC3M-LN4 cell line inhibited tumour growth (Liu N. et al. *Cancer Res* 61:5207 (2001)). This finding suggests that overproduction of HA is required for tumour progression and it appears that elevated production of HA by prostate stroma and cancer cells is a negative prognostic factor (Liu, N. et al. *Cancer Res* 61: 5207 (2001)). Overexpression of HAS2 and HAS3 promotes anchorage-independent growth and tumourigenicity in immunocompromised mice (Kosaki, R. et al. *Cancer Res* 59:1141 (1999); Liu, N. et al. *Cancer Res* 61:5207 (2001); Li, Y. et al. *Br J Cancer*

85:600 (2001)). Compared to HAS1 and HAS3, the HAS2 gene is easily regulated in response to mechanical injury in human peritoneal mesothelial cells in vitro and in dermal fibroblasts and osteoblasts in response to glucocorticoids (Yung, S. et al. *Kidney Int* 58:1953 (2000); Jacobson, A. et al. *Biochem J* 348:29 (2000); Zhang, W. et al. *Biochem J* 349:91 (2000)). Transfected HAS2 has been shown to induce transformed growth (Zoltan-Jones, A. et al. *J Biol Chem* 2003 Sep 3 [Epub ahead of print])

Overexpression of HAS1 or HAS2, both of which appear to synthesize high molecular weight HA, may activate hyaluronidase, an enzyme which degrades HA molecules and which is observed to be upregulated or downregulated during the progression of human cancer (Lees, V. C. et al. *Lab Invest* 73:259 (1995)). Shorter forms of HA resulting from HA degradation have been implicated in angiogenesis (Lees, V. C. et al. *Lab Invest* 73:259 (1995); West, D. C. et al. *Science* 228:1324 (1985); West, D. C. et al. *Ciba Found Symp* 143:187 (1989)). Therefore, changes to HAS1 and/or HAS3 gene regulation most likely results from significant changes in the cell or tissue in response to external or internal stimuli.

In mammary carcinoma cells, transfection with HAS1 transcripts resulted in the formation of increased metastasis as compared to that in controls (Itano, N. et al. *Cancer Res* 59:2499 (1999)). However, little is known about the role of HAS1 in various types of cancers, and regulation in response to external stimuli is not clear because of the nature of the gene. The lifetime of HAS1 transcripts may be very short and/or HAS1 may be expressed at low levels, compromising its detection by standard conventional gel electrophoresis. However, since HAS1 appears to be stringently regulated, its basal overexpression by tumour cells appears to be the result of dramatic changes in these cells.

In addition to extracellular HA molecules which are extruded into the extracellular compartment, an intracellular HA has been detected in the cytoplasm and the nucleus of various tissues such as the brain, liver, arteries, cumulus cells and oocytes (Dahl, I. M. et al. *Blood* 93:4144 (1999a); Furukawa, K. et al. *Biochim Biophys Acta* 585:575 (1979); Itano, N. et al. *Cancer Res* 59:2499 (1999); Londono, I. et al. *Histochem Cytochem* 36:1005 (1988); Margolis, R. K. et al. *Biochim Biophys Acta* 451:465 (1976); Ripellino, J. A. et al. *J Cell Biol* 106:845 (1988); Ripellino, J. A. et al. *J Cell Biol* 108:1899 (1989); Simpson, M. A. et al. *Am J Pathol* 161:849 (2002)). This intracellular HA can regulate gene transcription and/or the cell cycle by binding to the cell cycle control protein CDC37 and through the activation of the erk kinase pathway via the intracellular form of the HA binding receptor, Receptor for HA Mediated Motility (RHAMM) (Grammatikakis, N. et al. *J Biol Chem* 270:16198 (1995); Zhang, S. et al. *J Biol Chem* 273:11342 (1998)). In turn, activation of the erk kinase could induce transcription of many types of genes.

Intracellular localization of HA has been detected in nucleoli and in the nuclear periphery of areas of condensed chromatin (Evanko, S. P. et al. *J Histochem Cytochem* 47:1331 (1999)). Evanko et al. showed localization of intracellular HA during mitosis at the metaphase plate (Evanko, S. P. et al. *J Histochem Cytochem* 47:1331 (1999)). Furthermore, intracellular HA was detected around chromosomes during their rearrangement and separation in anaphase. In concert with previous findings, this work suggests a significant role of HA and HASs in mitosis and especially in chromatin condensation which occurs through interaction with histone and lamin (Cremer, T. et al. *Nat Rev Genet* 2:292 (2001)). Evanko et al. suggest a possible role for nuclear HA in ribosomal production and trafficking, or MRNA processing (Evanko, S. P. et al. *J Histochem Cytochem* 47:1331 (1999)). The source of intracellular HA, up to now, has remained unclear.

Multiple Myeloma (MM) is an incurable bone marrow (BM) cancer characterized by osteolytic bone lesions, BM plasmacytosis and monoclonal gammopathy. Molecular studies conducted in our laboratory revealed circulating, late stage, drug-resistant B-cells with clonotypic VDJ rearrangements in the peripheral blood (PB) of patients with MM. We believe that these cells migrate to the BM and give rise malignant plasma cells (PC) subsequently facilitating disease progressions. These drug-resistant clonotypic cells express the RHAMM oncogene. Furthermore, over-expression and/or inhibition of intracellular RHAMM dysregulates mitosis, likely leading to chromosomal instabilities and malignant spread in MM by mediating HA-dependent motility. Given the high remission rate and poor understanding of the disease, clinicians face a difficult challenge in directing treatment for the disease. A diagnostic test allowing the clinician to assess the severity of the disease through assessment of the likelihood of patient survival would be of great assistance to the medical community.

Current methods for monitoring myeloma involve bone marrow aspirates or core biopsies of the bone marrow, painful procedures that require an MD to perform them. The cells in the aspirate or biopsy are then viewed by an experienced pathologist using microscopic analysis, a time consuming process. This mode of testing depends on the biopsy needle penetrating an area of the bone marrow that is infiltrated by malignant cells. Since the distribution of such cells is not even throughout the bone marrow, this can result in "geographic misses" when the needle draws cells from an area that does not have malignant infiltration. It is also insensitive in that it cannot detect cells that have morphology different from that of classical plasma cells even though such cells may have the molecular signature that unequivocally identifies the myeloma clone. An alternate method involves analysis of monoclonal protein, the protein secreted by the bone marrow plasma cells, as measured by a blood test. This test is relatively painless but is insensitive, able to detect only relatively high levels of the protein excluding its use for monitoring minimal disease and early stages of relapse, and does not detect those patients whose cancer does not secrete the protein or as disease progression occurs has lost the ability to secrete it.

SUMMARY OF THE INVENTION

In order to overcome some of the above-discussed difficulties for monitoring progression of, or presence of, cancers of the blood, in one of its broad aspects the present invention provides a method involving the mixing of a cell or sample of a cell population from a mammal with a compound which specifically binds to specific expression patterns of HAS genes, and reacting further with additional compounds including at least two oligonucleotide primers to determine if a complex has formed with the first compound and the expressed patterns of HAS genes.

More specifically, the method of the subject invention in one of its broad aspects comprises the steps of: (1) mixing a cell or sample of a cell population from a mammal, usually human, with at least one compound which specifically binds to the HAS1Va or HAS1Vb or HAS1Vc mRNA transcript or products arising directly or indirectly therefrom; and (2) reacting said complex such that the presence or absence of the complex may be assessed.

More specifically the method of the subject invention in one of its broad embodiments involves a Reverse Transcriptase Polymerase Chain Reaction (RT-PCR) reaction comprising: (1) mixing a cell or sample of a cell population from a mammal, usually human, with reverse transcriptase in such conditions enabling conversion of mRNA to DNA templates, generating cDNA templates; (2) mixing said DNA templates with at least two oligonucleotide primers specific for the HAS1Va or HAS1Vb or HAS1Vc cDNA template; (3) reacting said complex with enzymes and compounds known to the art to enable specific fragments of DNA to be increased in number; and (4) detecting the presence of an increased number of resulting DNA fragments of particular size associated with the presence of HAS1Va or HAS1Vb or HAS1Vc mRNA transcript in the sample.

In another of its broad aspects the present invention provides for a method of assessing likelihood of survival over time in a multiple myeloma patient through characterization of HAS isoenzyme or isoenzyme variant expression in a cell or cell population obtained from the patient.

The invention further provides for a kit comprised of nucleotide primers complementary to the mRNA transcript of a HAS isoenzyme or isoenzyme variant gene product, and reagents sufficient to effect an appropriate reaction, for detection and characterization of HAS isoenzyme or isoenzyme variant(s) expression for use in a diagnostic or clinical assessment of a patient.

The invention further provides for a kit comprised of nucleotide primers complementary to the cDNA generated from the RNA transcript of a HAS isoenzyme or isoenzyme variant gene, and reagents sufficient to effect an appropriate reaction, for detection and characterization of HAS isoenzyme or isoenzyme variant(s) expression for use in a diagnostic or clinical assessment of a patient.

More specifically the invention provides for a kit comprised of (1) at least one compound which specifically binds to HAS isoenzyme or isoenzyme variant mRNA transcript or products arising directly or indirectly therefrom; (2) compounds sufficient to enable the reacting of said compound with a sample of a cell or cell population from a mammal, usually human, thereby forming a complex; (3) compounds enabling the presence or absence of the complex to be assessed; and (4) instructions enabling one to detect the presence of the HAS isoenzyme or isoenzyme variants.

More specifically the invention provides for a kit comprised of (1) at least one oligonucleotide which specifically binds to the HAS isoenzmye or isoenzyme variant mRNA transcript or products arising directly or indirectly therefrom; (2) compounds sufficient to enable the reacting of said compound with a sample of a cell or cell population from a mammal, usually human, thereby generating a multiplicity of specific nucleotide fragments; (3) detecting the presence of said multiplicity of specific nucleotide fragments; and (4) instructions enabling one to detect the presence of the HAS isoenzyme or isoenzyme variant.

More specifically the invention provides for a kit comprised of (1) at least one compound which specifically binds to the HAS isoenzyme or isoenzyme variant protein; (2) compounds sufficient to enable the reacting of said compound with a sample of a cell or cell population from a mammal, usually human, thereby forming a complex; (3) compounds enabling the presence or absence of the complex to be assessed; and (4) instructions enabling one to detect the presence of the HAS isoenzyme or isoenzyme variants.

The present invention further provides for a kit for monitoring of patients having previously-diagnosed Waldenstrom's Macroglobulinemia (hereinafter "WM"), on a regular basis, so as to assist in monitoring disease progression and/or treatment.

The present invention further provides for a kit for diagnosis of Multiple Myeloma (hereinafter "MM") and monitoring of previously-diagnosed MM patients, on a regular basis, assisting in monitoring disease progression and/or treatment.

The invention further provides for a method to assess clinical outcome in a Multiple Myeloma patient prior to determining treatment regimen through characterization of HAS isoenzyme or isoenzyme variant expression in a cell or cell population obtained from the patient.

The invention further provides for a method of treating cells or cell populations experiencing abnormal HAS isoenzyme or isoenzyme variant expression comprising administration of a compound to the cells sufficient to interfere with activity of HAS isoenzymes or isoenzyme variants.

The invention further provides for a method of treating cells or cell populations experiencing abnormal HAS isoenzyme or isoenzyme variant expression comprising administration of a compound sufficient to interfere with expression of the HAS isoenzymes or isoenzyme variants.

The invention further provides, in another aspect, for the use of nucleic acid probes or primers in characterization of HAS isoenzyme or isoenzyme variant expression in a cell or cell population as a determinant for the presence of disease in a cell or cell population.

The invention provides, in yet another aspect, for a method to diagnose the susceptibility of a cell or cell population to disease through characterization of the expression of HAS isoenzyme or isoenzyme variants.

The invention provides, in yet another aspect, for the use of nucleic acid probes or primers enabling characterization of HAS isoenzyme or isoenzyme variant expression in a cell or cell population as a determinant for disease in a cell or cell population.

The invention provides, in yet another aspect, for the use of nucleic acid probes or primers enabling characterization of HAS isoenzyme or isoenzyme variant expression in a cell or cell population as a determinant for the susceptibility of a cell or cell population to disease.

The invention, in a related broad aspect further provides for a method to treat cells or cell populations containing cells susceptible to disease comprising the assessment of the presence of expression of HAS isoenzymes or variants thereof, followed by treatment or elimination of the cells or cell populations in which abnormal HAS isoenzyme or isoenzyme variants are observed.

The invention, in a related broad aspect provides for a method to treat cells or cell populations containing diseased cells comprising the assessment of the presence of expression of HAS isoenzymes or variants thereof, followed by treatment or elimination of the cells or cell populations in which abnormal HAS isoenzyme or isoenzyme variants are observed.

The invention in a further aspect provides for a method to treat a cell population containing diseased cells comprising the assessment of the presence of expression of HAS isoenzymes or variants thereof, followed by treatment with compounds inhibitory to HAS isoenzyme or isoenzyme variant activity.

More specifically the invention provides for a method to treat a cell population containing diseased cells comprising the assessment of the presence of expression of HAS isoenzymes or variants thereof, followed by treatment with vesnarinone.

The invention in a flurther aspect provides for a method to treat cells or cell populations containing cells susceptible to disease comprising the assessment of the presence of expression of HAS isoenzymes or isoenzyme variants, followed by treatment with compounds inhibitory to HAS isoenzyme or isoenzyme variant activity.

The invention in a further aspect provides for a method to treat cells or cell population containing diseased cells comprising the assessment of the presence of expression of HAS isoenzymes or variants thereof, followed by treatment with compounds inhibitory of the gene expression of HAS isoenzyme or isoenzyme variant.

The invention in a further aspect provides for a method to treat cells or cell populations containing cells susceptible to disease comprising the assessment of the presence of expression of HAS isoenzymes or variants thereof, followed by treatment with compounds inhibitory of the gene expression of HAS isoenzyme or isoenzyme variant.

The invention in a further embodiment provides for a method to determine the presence of HAS1Va in a cell or cell population.

The invention in a further aspect provides for the use of nucleotide probes or primers to detect the presence of HAS1Va expression in a cell or cell population.

The invention in a fuirther embodiment provides for a method to determine the presence of HAS1Vb in a cell or cell population.

The invention in a further embodiment provides for the use of a nucleotide probe or primers to detect the presence of HAS1Vb expression in a cell or cell population.

The invention in a further embodiment provides for a method to determine the presence of HAS1Vc in a cell or cell population.

The invention in a further embodiment provides for the use of a nucleotide probe or primers to detect the presence of HAS1Vc expression in a cell or cell population.

The present invention provides for a DNA molecule, isolated and purified, comprising a DNA segment encoding the eukaryotic hyaluronan synthase isoenzyme variant HAS1Va; or biologically active subunit thereof. A preferred embodiment of the invention is a DNA molecule represented by SEQ ID NO:3.

The present invention provides for a DNA molecule, comprising a DNA segment encoding the eukaryotic hyaluronan synthase isoenzyme variant HAS1Vb; or biologically active subunit thereof. A preferred embodiment of the invention is a DNA molecule represented by SEQ ID NO:5.

The present invention provides for a DNA molecule, comprising a DNA segment encoding the eukaryotic hyaluronan synthase isoenzyme variant HAS1Vc; or biologically active subunit thereof. A preferred embodiment of the invention is a DNA molecule represented by SEQ ID NO:7.

As used herein, the term "HAS1Va" is preferably defined to mean a polypeptide comprising SEQ ID NO:4, as well as variants of SEQ ID NO:4 which have at least 80% identity or homology, preferably at least about 90%. Furthermore, the term HAS1Va is defined to mean a biologically active subunit of the polypeptide comprising SEQ ID NO:4, as well as variants of SEQ ID NO:4 which have at least 80% identity or homology, preferably at least about 90%. Biologically active subunits of HAS1Va and biologically active subunits of HAS1Va falling within the scope of the invention have at least about 50%, preferably at least about 80%, and more preferably at least about 90%, the activity of an HAS1Va polypeptide comprising SEQ ID NO:4. Activity of an HA synthase can be measured by methods known to the art, including but not limited to those methods described in Proc. Natl. Acad. Sci. USA 93, 4543(1996) and J. Biol. Chem. 271 9875(1996).

As used herein, the term "HAS1Vb" is preferably defined to mean a polypeptide comprising SEQ ID NO:6, as well as variants of SEQ ID NO:6 which have at least 80% identity or homology, preferably at least about 90%. Furthermore, the term HAS1Vb is defined to mean a biologically active subunit of the polypeptide comprising SEQ ID NO:6, as well as variants of SEQ ID NO:6 which have at least 80% identity or homology, preferably at least about 90%. Biologically active subunits of HAS1Vb and biologically active subunits of HAS1Vb falling within the scope of the invention have at least about 50%, preferably at least about 80%, and more preferably at least about 90%, the activity of an HAS1Vb polypeptide comprising SEQ ID NO:6. Activity of an HA synthase can be measured by methods known to the art as described above for HAS1Va.

As used herein, the term "HAS1Vc" is preferably defined to mean a polypeptide comprising SEQ ID NO:8, as well as variants of SEQ ID NO:8 which have at least 80% identity or homology, preferably at least about 90%. Furthermore, the term HAS1Vc is defined to mean a biologically active subunit of the polypeptide comprising SEQ ID NO:8 as well as variants of SEQ ID NO:8 which had at least 80% identity or homology, preferably at least about 90%. Biologically active subunits of HAS1Vc and biologically active subunits of HAS1Vc falling within the scope of the invention have at least about 50% preferably at least about 80% and more preferably at least about 90%, the activity of an HAS1Vc polypeptide comprising SEQ ID NO:8. Activity of an HA synthase can be measured by methods known in the art as described above for HAS1Va.

Contemplated by the invention is a HAS1Va or HAS1Vb or HAS1Vc specific oligonucleotide, comprising a DNA sequence that has at least 80%, preferably at least about 90%, and more preferably at least 95%, sequence identity with SEQ ID NO:3 (HAS1Va), SEQ ID NO:5 (HAS1Vb), or SEQ ID NO:7 (HAS1Vc) respectively. An oligonucleotide probe or primer of the invention has at least 7-50, preferably about 10-40, and more preferably 15-35 nucleotides. Preferably, the oligonucleotide probe or primer of the invention comprise at least 7 nucleotides on their 3' end which has at least 85% identity to SEQ ID NO:3, SEQ ID NO:5, or SEQ ID NO:7.

The invention provides for the use of an isolated and purified DNA molecule, such as a probe or a primer, for example an oligonucleotide, of at least seven, preferably at least fifteen, nucleotide bases which hybridize under stringent conditions to a cellular nucleotide molecules such that the HAS expression profile of the cell or cell population may be determined. The probes or primers of the invention may be detectably labelled or have a binding site for a detectable label. The probes or primers are useful to detect, quantify and/or amplify nucleotide strands with complementary sequences related to the HAS isoenzymes or isoenzyme variants in a cell or cell population thereby enabling one skilled in the art to determine the HAS expression profile in a cell or cell population.

The invention provides for the use of an isolated and purified DNA molecule, such as a probe or a primer, for example an oligonucleotide, of at least seven, preferably at least fifteen, nucleotide bases, which hybridize under stringent conditions to a cellular nucleotide molecules such that the expression of HAS1Va in a cell or cell population may be determined. The probes or primers of the invention may be detectably labelled or have a binding site for a detectable label. The probes or primers are usefuil to detect, quantify and/or amplify nucleotide strands with complementary sequences related to the HAS1Va isoenzyme variant in a cell or cell population thereby enabling one skilled in the art to determine the HAS1Va expression in a cell or cell population.

The invention provides for the use of an isolated and purified DNA molecule, such as a probe or a primer, for example an oligonucleotide, of at least seven, preferably at least fifteen, nucleotide bases, which hybridize under stringent conditions to a cellular nucleotide molecules such that the expression of HAS1Vb in a cell or cell population may be determined. The probes or primers of the invention may be detectably labelled or have a binding site for a detectable label. The probes or primers are useful to detect, quantify and/or amplify nucleotide strands with complementary sequences related to the HAS1Vb isoenzyme variant in a cell or cell population thereby enabling one skilled in the art to determine the HAS1Vb expression in a cell or cell population.

The invention provides for the use of an isolated and purified DNA molecule, such as a probe or primer, for example an oligonucleotide, of at least 7, preferably at least 15, nucleotide bases, which hybridize under stringent conditions to a cellular nucleotide molecules such that the expression of the HAS1Vc in a cell or cell population may be determined. The probes or primers of the invention may be detectably labelled or have a binding site for a detectable label. The probes or primers are useful to detect, quantify and/or amplify nucleotide strands with complimentary sequences related to the HAS1Vc isoenzyme variant in a cell or cell population thereby enabling one skilled in the art to determine the HAS1Vc expression in a cell or cell population.

Further provided is a method for detecting expression of HAS1Va. The method comprises contacting an agent that binds to HAS1Va nucleotide or derived nucleotide so as to form a complex. Then the presence of an amount of complex formation is detected and the presence of the complex formation is correlated with the presence or absence of the condition.

Further provided is a method for detecting expression of HAS1Vb. The method comprises contacting an agent that binds to HAS1Vb mRNA so as to form a complex. Then the presence of an amount of complex formation is detected and the presence of the complex formation is correlated with the presence or absence of the condition.

Further provided is a method for detecting expression of HAS1Vc. The method comprises contacting an agent that binds to HAS1Vc mRNA so as to form a complex. Then the presence of an amount of complex formation is detected and the presence of the complex formation is correlated with the presence or absence of the condition.

Further provided is a method for detecting HAS1 isoenzyme or isoenzyme variants where the nucleotide is generic DNA.

Further provided is a method for detecting HAS1 isoenzyme or isoenzyme variants where the derived nucleotide is mRNA.

Further provided is a method for detecting HAS1 isoenzyme or isoenzyme variants where the derived nucleotide is DNA.

Further provided is a method for detecting expression of HAS1Va. The method comprises contacting an amount of DNA obtained by reverse transcription of RNA from a mammalian cell or cell population which is suspected to express HAS1Va, with an amount of at least two oligonucleotides under conditions effective to amplify the DNA by a polymerase chain reaction so as to yield an amount of amplified HAS1Va DNA. At least one nucleotide is an HAS1Va specific oligonucleotide. The presence or amount of the amplified HAS1Va DNA is then detected.

Further provided is a method for detecting expression of HAS1Vb. The method comprises contacting an amount of DNA obtained by reverse transcription of RNA from a mammalian cell or cell population which is suspected to express HAS1Vb, with an amount of at least two oligonucleotides under conditions effective to amplify the DNA by a polymerase chain reaction so as to yield an amount of amplified HAS1Vb DNA. At least one nucleotide is an HAS1Vb specific oligonucleotide. The presence or amount of the amplified HAS1Vb DNA is then detected.

Further provided is a method for detecting expression of HAS1Vc. The method comprises contacting an amount of DNA obtained by reverse transcription of RNA from a mammalian cell or cell population which is suspected to express HAS1Vc, with an amount of at least two oligonucleotides under conditions effective to amplify the DNA by a polymerase chain reaction so as to yield an amount of amplified HAS1Vc DNA. At least one nucleotide is an HAS1Vc specific oligonucleotide. The presence or amount of the amplified HAS1Vc DNA is then detected.

Further provided is a method for detecting expression of HAS1Va. The method comprises contacting an amount of mRNA from a mammalian cell or cell population which is suspected to express HAS1Va, with an amount of at least two oligonucleotides under conditions effective to amplify the nucleotide by a polymerase chain reaction so as to yield an amount of amplified DNA. At least one nucleotide is a HAS1Va specific oligonucleotide. The presence or amount of the amplified HAS1Va nucleotide is then detected.

Further provided is a method for detecting expression of HAS1Vb. The method comprises contacting an amount of mRNA from a mammalian cell or cell population which is suspected to express HAS1Vb, with an amount of at least two oligonucleotides under conditions effective to amplify the DNA by a polymerase chain reaction so as to yield an amount of amplified DNA. At least one nucleotide is an HAS1Vb specific oligonucleotide. The presence or amount of the amplified HAS1Vb nucleotide is then detected.

Further provided is a method for detecting expression of HAS1Vc. The method comprises contacting an amount of mRNA from a mammalian cell or cell population which is suspected to express HAS1Vc, with an amount of at least two oligonucleotides under conditions effective to amplify the DNA by a preliminary chain reaction so as to yield an amount of amplified DNA. At least one nucleotide is an HAS1Vc specific oligonucleotide. The presence or amount of the amplified HAS1Vc is then detected.

The invention provides for detection of isoenzyme variant HAS1Va though contacting a cell or cell population with an agent, selected so as to interact selectively with HAS1Va polypeptide or protein, followed by detection of the complex formed by said agent and HAS1Va. The invention further provides for said agent to include, but not be limited to, an antibody or antibody fragment.

The invention provides for detection of isoenzyme variant HAS1Vb though contacting a cell or cell population with an agent, selected so as to interact selectively with HAS1Vb polypeptide or protein, followed by detection of the complex formed by said agent and HAS1Vb. The invention further provides for said agent to include, but not be limited to, an antibody or antibody fragment.

The invention provides for detection of isoenzyme variant HAS1Vc though contacting a cell or cell population with an agent, selected so as to interact selectively with HAS1Vc polypeptide or protein, followed by detection of the complex formed by said agent and HAS1Vc. The invention further provides for said agent to include, but not be limited to, an antibody or antibody fragment.

The invention provides for the method of determining the presence of HAS1Va in a cell or cell population through detection of a single nucleotide polymorphism of the HAS1 gene described by SEQ ID NO:1, resulting in the conversion of base-pair 924 from a cytosine to a thymidine residue.

The invention further provides for the detection of the single nucleotide polymorphism described herein through contacting an agent that binds to mRNA, or nucleic acid derived therefrom, to form a complex. Then the presence of an amount of complex formation is detected and the presence of the complex formation correlated with the presence or absence of HAS1Va.

The invention further provides for the detection of the single nucleotide polymorphism described herein through contacting an agent that binds to genomic DNA or nucleic acids derived from genomic DNA. Then the presence of an amount of complex formation is detected and the presence of the complex formation correlated with a predisposition to expression of HAS1Va.

BRIEF DESCRIPTION OF THE FIGURES

FIG. 18. Alternative predicted intron splice sites. Depiction of alternative and observed splice sites within the HAS1 mRNA sequence, SEQ ID NO:15.

DETAILED DESCRIPTION OF THE INVENTION

Definitions

Figure 1:
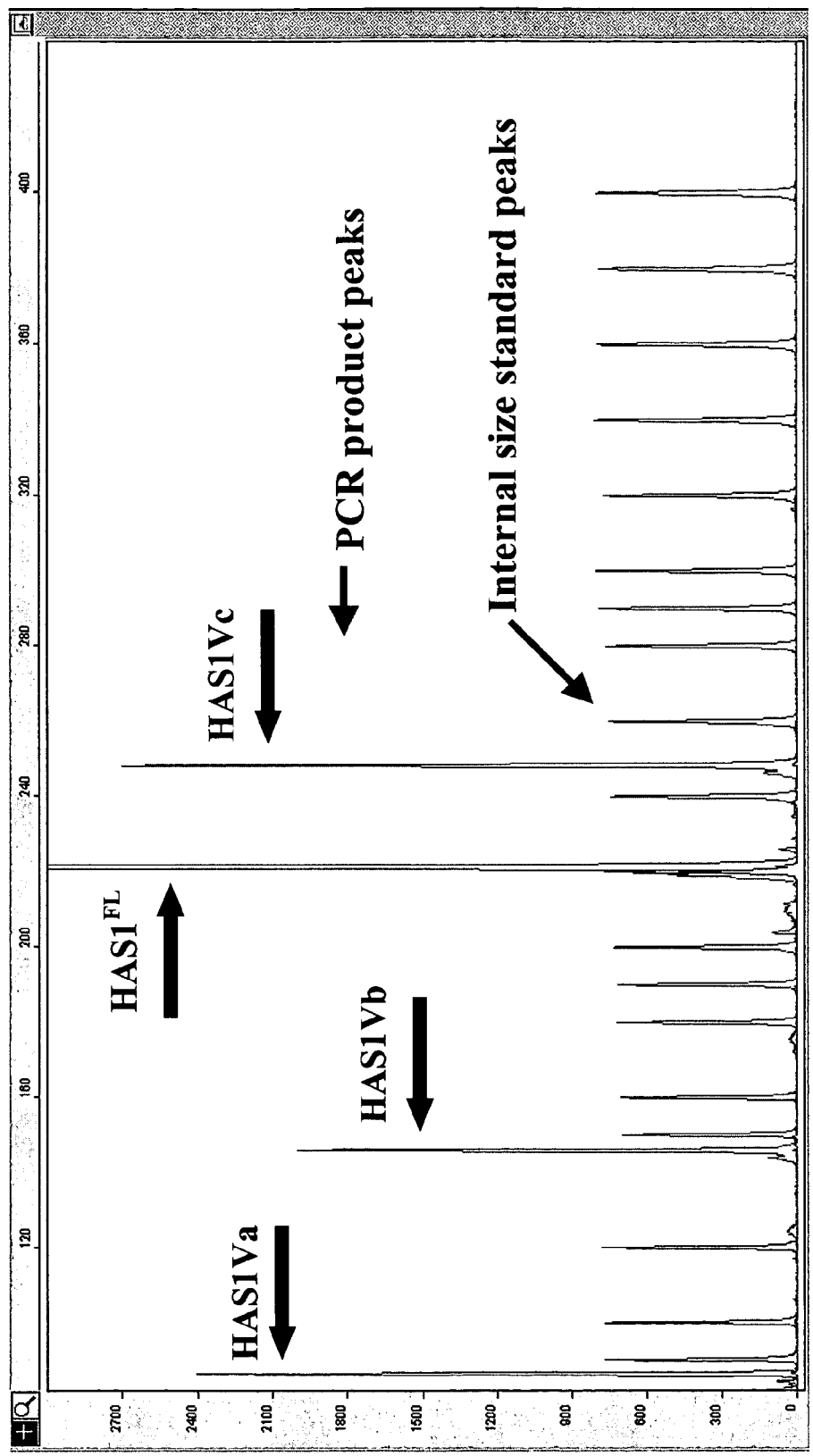
FIG. 1. Detection of HAS1 and its novel variants transcripts in MM patients. DNA size separation of fragments of RT-PCR product arising from a reaction of HAS1 specific primers with cDNA generated from cellular mRNA; with fragment size represented on the X-axes and quantity of fragments represented on the Y-axes.

As used herein "stringent conditions" means conditions that detect a nucleic acid molecule with at least 80%, preferably at least 90%, nucleotide sequence homology to the nucleotide sequence. See Sambrook et al. *Molecular Cloning a Laboratory Manual* Cold Spring Harbor Press 2 ed, (1989); *PCR Primer: A Laboratory Manual*. Carl Dieffenbach Ed. Cold Spring Harbor Press (1995), for a selection of conditions suitable for washing and hybridizing nucleic acids allowing for stable and specific duplex formation and/or Reverse. Transcriptase Polymerase Chain Reaction (RT-PCR). Stringent conditions are those that either employ low ionic strength and high temperature for washing, or employ a denaturing agent during hybridization.

As used herein "Polymerase Chain Reaction" or "PCR" refers to the process or technique of increasing the concentration of a segment of a target sequence of pre-selected genomic material comprised of, but not limited to, DNA, mRNA, cDNA, or fragments thereof, as generally described in U.S. Pat. Nos. 4,683,195, 4,683,202, and 4,965,188.

As used herein "isoenzyme variants" refers to a protein resulting from the alteration of the native HAS isoenzyme arising from post-translational or pre-translational modification.

As used herein "disease" means a state in a mammal which may directly or indirectly lead to a cellular, cell population, or systemic state detrimental to the mammal.

As used herein, the term "probe" refers to an oligonucleotide, single-stranded or double-stranded, produced synthetically or occurring naturally; that is capable of selectively binding to a nucleic acid of interest.

As used herein, the term "primer" refers to an oligonucleotide produced synthetically or naturally occurring, which is capable of acting as a point of initiation of nucleotide synthesis when placed under conditions in which nucleotide synthesis extending from the primer, complimentary to a nucleic acid strand, is possible.

As used herein, "therapeutic" refers to a method or process to vary the expression, transcription or post-translational modification of HAS1 or HAS1 isoenzyme variants in a cell or cell population; in which the expression, transcription or post-translational modification of HAS1 or HAS1 isoenzyme variants, or lack thereof, is deleterious to the cell or cell population or gives rise to a susceptibility to a condition which is deleterious to the cell or cell population.

As used herein, "microfluidic devices", sometimes termed "lab on a chip", "microfluidic chips" or "microsystem platforms" refer to the result of applying microelectronic fabrication technologies to produce a network of wells and channels etched into glass and/or molded into polymers that are bonded to glass or silicon chips. Within these wells and microchannels, cells and reagents can be manipulated by a variety of methods including gravity feed, applying electric or magnetic fields and results detected by, for example, image analysis or optical means. Microfluidic chips provide for PCR reactions and analysis of PCR products (Footz, T. S. et al. *Electrophoresis* 22:3868 (2001); Obeid, P. J. et al. *Analytical Chemistry* 75:288 (2003); Backhouse C. J. et al. *Electrophoresis* 24:1777 (2003)). They enable high resolution separations through polymer-filled microchannels using capillary electrophoresis of e.g. multiple PCR products, and can exhibit a high level of integration by combining multiple functions on a single chip, for example cell sorting and RT-PCR reactions for gene expression or genomic profiles of a given cell or population of cells (Backhouse, C. J. et al. *Proceedings of the International Conference on MEMS, NANO and Smart Systems* 377 (2003)). Within a microfluidic device, sample processing can be implemented and cells can be separated by a variety of means, including dielectrophoresis, and processed in a variety of ways, including analysis of HAS gene expression in the manner of the invention disclosed herein.

A Role for HAS1 in Malignant Spread

Clinically, MGUS is a non-malignant condition, found in 3% of the population over age 70. The cumulative risk for progression to MM after 30 years is 30% (Kyle R. A. et al. *Immun Rev* 194:112 (2003); Kyle, R. A. et al. *New England J Medicine* 346:564 (2002)). MGUS is widely viewed by those skilled in the art as a "pre-malignant" condition that can progress to frank MM. It is thus valuable to determine the gene expression patterns in MGUS in comparison to MM, to identify characteristics that may occur as the malignancy progresses from very early stages to more aggressive stages. For a variety of characteristics, MGUS differs from B cells in healthy donors, but also sometimes differs from those in patients with actively progressing MM. However, the characteristics of the monoclonal plasma cells that define MGUS suggest that MGUS might also plausibly be viewed as a malignant clone under stringent control that renders it dormant.

Because it represents the early stages of malignant progression, analysis of characteristics of gene expression in MGUS is widely thought to be valuable for identification of those patients who are at risk of progressing to actively progressing MM. It is difficult to clinically distinguish between early MM and advanced stage MGUS. MGUS patients have <10 g/L of mIg and <10% plasma cells in their BM. A variety of measures suggest that the MGUS clone may include plasma cells having malignant characteristics. Chromosomal changes are a common finding in plasma cells from MGUS (Avet-Loiseau, H. et al. *Blood* 94:2583 (1999)). A subset of MGUS plasma cells is extensively DNA hyperdiploid (Almeida, J. et al. *Pathol Biol (Paris)* 47:119 (1999)). The pattern of cytogenetic abnormalities detected over time suggests a multi-step process characterized by gradual acquisition of chromosomal abnormalities within the MGUS clone. Illegitimate IgH rearrangements, widely viewed as central to progression of MM, are found in the majority of plasma cells from 46% of MGUS patients (Avet-Loiseau, H. et al. *Cancer Res* 59: 4546 (1999)). The incidence of illegitimate IgH rearrangements is comparable to that found in MM (Avet-Loiseau, H. et al. *Blood* 94: 2583 (1999)). Despite the evidence that MGUS includes cells with properties comparable to those in MM, and the observation that some MGUS patients have plasma cell numbers approaching those in overt MM, MGUS patients have no evidence of malignant disease, suggesting that some type of control may be operative.

Clinically, MM has been considered as a bone marrow disease; however molecular studies done by many groups, including ours, have revealed a population of abnormal B cells, including the small lymphocytes and the large monocytoid cells, in the peripheral blood of patients with MM (Pilarski, L. M. et al. *Blood* 83:724 (1994); Pilarski, L. M. et al. *Blood* 90:3751 (1997); Szczepek, A. J., et al. *Blood* 89:1824 (1997)). These B cells are circulating late stage B cells characterized by a clonotypic IgH VDJ rearrangement, a unique marker for the identification of malignant cells in each patient (Pilarski, L. M. et al. *Blood* 83:724 (1994); Pilarski, L. M. et al. *Blood* 90:3751 (1997); Szczepek, A. J., et al. *Blood* 89:1824 (1997)). These malignant $CD19^+$ $CD20^+$ $CD24^+$ B cells appear to be drug-resistant cells characterized by stem cell like properties (i.e. the expression of stem cell marker CD34) and by the expression of many receptors required for adhesion and motility including CD44 and RHAMM (Jensen, G. S. et al. *Scand J Immunol* 36:843 (1992); Jensen, G. S. et al. *Am J Hematol* 43:29 (1993); Masellis-Smith, A. et al. *Blood* 87:1891 (1996); Masellis-Smith, A. et al. *Cancer Res* 57:930 (1997); Turley, E. A. et al *Blood* 81:446 (1993)). We believe that these clonotypic, late stage cells migrate to the bone marrow where they interact with bone marrow stromal cells and give rise malignant PC. Studies done by our lab have shown that the motility of clonotypic B cells is mediated by RHAMM and hyaluronan (HA) (Masellis-Smith, A. et al. *Blood* 87:1891 (1996)).

The observation that HASs are all found in the blood of MM patients but, with the exception of HAS3, not in the blood of healthy donors; coupled with the association between the presence of these isoenzyme variants in the blood and poor survival, in the absence of such prognostic significance for HAS isoenzyme variants in the BM, suggests that these HAS isoenzyme variants are upregulated in the malignant clone in MM and are markers of circulating tumour burden. Significant correlations between poor survival and expression of HAS genes in blood cells are found for HAS1, HAS2, HAS1Va and HAS1Vb. The particularly remarkable association between blood HAS1Vb and survival, and the rare detection of HAS1Vb in the BM, suggests that HAS1Vb may be preferentially upregulated in circulating malignant cells versus those resting in the BM.

HA is known to interact with other proteins to transmit signals. The coiled-coil protein RHAMM is distributed in different compartments of the cell, including the cell surface, nucleus and cytoplasm (Gares, S. L. et al. *J Leukoc Biol* 64:781 (1998); Maxwell, C. A. et al. *Mol Biol Cell* 14:2262 (2003); Entwistle, J. Hall et al. *J Cell Biochem* 61:569 (1996); Hall, C. L. et al. *Cell* 82:19 (1995)). Overexpression of RHAMM promotes malignant cell migration and leads to metastatic development and tumour growth. RHAMM is implicated in the Ras signaling pathway (Entwistle, J. et al. *J Cell Biochem* 61:569 (1996); Hall, C. L. et al. *Cell* 82:19 (1995)). Two splice variants of RHAMM have been identified: $RHAMM^{-exon4}$ and $RHAMM^{-exon13}$, both of which are overexpressed in MM and other B lymphocyte malignancies (Crainie, M. et al. *Blood* 93:1684 (1999)), which suggests a significant role for RHAMM in mediating the spread of malignant cells throughout the bone marrow of patients with MM (Maxwell, C. A. et al. *Mol Biol Cell* 14:2262 (2003)). HAS1 appears to be intracellular in its localization, MM cells express intracellular HA, and the domains through which RHAMM interacts with the centrosome overlap the HA binding domains (Maxwell, C. A. et al. *Mol Biol Cell* 14:2262 (2003)). The correlations between HAS gene expression and poor outcome may reflect sufficient modulation of RHAMM to allow some cells with mis-segregated chromosomes (due to RHAMM disruption of bipolar spindle) to complete mitosis with abnormal chromosomes complements. Thus we believe HAS1 variants potentiate genetic instability and survival of genetic variants by preventing the apoptosis that occurs when RHAMM is too strongly overexpressed. RHAMM and HASs may act in concert to promote tumour progression. We believe the inhibition of HAS proteins provide an effective target for down-regulating RHAMM mediated malignant cell migration, as well as modulating RHAMM interactions with the centrosomes and the mitotic spindle. A number of methods for detecting and inhibiting the related HAS isoenzyme HAS2, which may be referred to for guidance with respect to HAS1 and its isoenzyme variants, is shown in U.S. Pat. No. 6,492,150 B1; the disclosure of which is hereby incorporated by reference.

The expression of HAS1 and its novel variants by motile malignant B cells suggests that HAS1 and its novel variants are involved in oncogenic processes, particularly contributing to the spread of MM. The expression of HAS1 and HAS1 variants, possibly in combination with HAS3, appears sufficient to synthesize the HA pericellular coat around MM B cells with a motile phenotype.

Our research allows us to conclude that:

a) The cell-type expression pattern of HAS1, HAS1 isoenzyme variants and HAS2 in MM B cells and MM BM PC, detected by GeneScan analysis, indicates that HAS1 and HAS2 are restricted to malignant B cells and plasma cells respectively.

b) HAS1 is sufficient for the production of an HA pericellular matrix around MM B cells. Normal B cells, which lack HAS1 but express HAS3, do not produce an HA pericellular matrix, nor do HAS2 expressing MM plasma cells. These results suggest that HA synthesis by HAS1, but not by HAS2 or HAS3, underlies the ability of MM B cells to migrate in vitro and potentially to spread in vivo.

c) The detection of novel HAS1 variants in MM B cells at high levels suggests that overexpression of this gene and abnormal HAS1 gene splicing to create HAS1 variants are characteristic of malignant cells. The presence of HAS1Va in MGUS patients suggests that its overexpression may be an early event in myelomagenesis. Full length HAS1 is largely intracellular, and based on their sequence HAS1 isoenzyme variants are also intracellular isoenzymes which are likely to synthesize intracellular HA, a ligand for intracellular RHAMM, and thus contribute to the RHAMM-induced dysregulation of mitosis and subsequent chromosomal abnormalities.

Potential Therapeutic Approaches Directed at HAS Gene Expression

Inhibition of the HAS isoenzyme and isoenzyme variant proteins may be obtained through a multitude of ways currently known in the art. This includes diminishing or eliminating transcription of the HAS genes through introduction into cells, oligonucleotides antisense to the mRNA transcript of the HAS gene (Nishida, Y. et al. *J Biol Chem* 31:21893 (1999); Rilla, K. et al. *J Cell Sci* 115:3633 (2002)), or through knockout of the HAS gene using site specific recombination (Itano, N. et al. Japanese Patent JP2000116382). Alternatively the HAS enzymes may be partially or completely inhibited through administration of compounds found to alter, diminish or eliminate HAS enzyme function including but not limited to vesnarinone (Ueki, N. et al. *Bioch Biophys Acta* 1495:160 (2000)).

HASs and HAS isoenzyme variants are expected to be inhibited by antisense constructs administered therapeutically (Yacyshyn, B. R. et al. *Gastroenterology* 114:1133 (1998); Jansen, B. et al. *Lancet* 356:1728 (2000); Kretschmer-Kazemi Far, R. et al. *Bioinformatics* 17:1056 (2001); Klasa, R. J. et al. *Am Soc Hematology Educational Program* 2001:443 (2001)); small inhibitory RNA (siRNA) administered therapeutically (Butz, K. et al. *Oncogene*, 22:5938 (2003); Farrow, B. et al. *Surgery* 134:197 (2003); Oliveira, D. M. et al. *Genesis* 36:203 (2003); Miyagishi, M. et al. *Nucleic Acids Res Suppl* 2:113 (2002); Lu P.Y. et al. *Curr Opin Mol Ther* 5:225 (2003); De Schrijver, E., *Cancer Res* 63:3799 (2003)); HA mimetic peptides that can be administered therapeutically (Ziebell, M.R. et al. *Chem Biol* 8:1081 (2001)); synthetic "antibody" Fab fragments from a phage display library, including but not limited to diabodies and other synthetic peptide compounds selected for their ability to bind to HAS epitopes, would be expected to attack any HAS and HAS variants (Knappik, A. et al. *J Mol Biol* 296:57 (2000); Kriangkum, J. et al. *Hybridoma* 19:33(2000); Kriangkum, J. et al. *Biomol Eng* 18:31(2001); Xu, B. et al. *Hybridoma* 18:315 (1999); Grim, J. et al. *J Mol Med* 76:451 (1998); Deshane, J, *J Clin Invest* 96:2980 (1995)); and intrabodies (intracellular synthetic Fab fragments) would be expected to inhibit intracellular HAS1 variants (Grim, J. et al. *J Mol Med* 76:451(1998); Deshane, J., *J Clin Invest* 96:2980 (1995)).

HA as a Therapeutic to Target HAS Activity

The ability of HA, and/or binding of extracellular HA by HA receptors on the cell surface; to down regulate HAS activity is deduced from the ability of hyaluronidase, mediating removal of HA, to stimulate HAS and HA synthesis. Extracellular HA inhibits HAS activity and removal of this extracellular HA by hyaluronidase degradation results in upregulation of HA synthesis by HASs (Larnier, C. et al. *Biochim Biophys Acta* 1014:145 (1989); Philipson, L. H. et al. *Biochemistry* 24:7899 (1985)). Disassociation of HA from the cell membrane using high salt also leads to activation of hyaluronan synthase, as does loss of CD44, which likely decreases surface bound HA (Luke H. J., Prehm P *Biochem J.* 343 Pt 1:71, (1999)). Increased hyaluronan synthase activity correlates with increased HA degradation (Sampson, P.M. et al. *J Clin Invest* 90:1492 (1992)). Glioma cell lines that overexpress HAS2, do so in conjunction with hyaluronidase expression, suggesting the removal of HA promotes HAS activity (Enegd, B. et al. *Neurosurgery* 50:1311 (2002)). Prostate cancer cell lines require HAS activity for HA dependent adhesion and removal of surface HA ablates this adhesion; addition of high amounts of exogenous HA (500 µg/ml) inhibits resynthesis of surface HA capable of reinstating adhesive processes (Simpson, M. A. et al. *J Biol Chem* 276: 17949 (2001)), indicating that high levels of exogenous HA prevent HAS activity. Finally in Multiple Myeloma, a disease characterized by extensive overexpression of HAS isoenzyme and isoenzyme variants, hyaluronidase is upregulated; suggesting that removal of extracellular HA may promote HAS gene expression (Laudet, A. et al. *Clin Chim Acta* 301: 159 (2000)).

Therefore, exogenous HA is expected to modulate functional activity of HAS-1 variants. While an understanding of a precise mechanism is not necessary to practise the invention, infusion of HA is believed to have any or all of several possible outcomes:

a) As HAS1 variants have HA binding domains, so that exogenous HA may compete with the synthetic process inactivating HAS1 activity directly, thus preventing proper accumulation and localization of intracellular HA. This is expected to disrupt the biological activity of intracellular HA and thus the oncogenic impact of HAS1 variants. Infused HA may inhibit HAS1 variant synthetic activity for therapeutic benefit.

b) Fragments of exogenous or even intact HA are likely to be internalized. This is expected to drastically increase the levels of intracellular HA able to compete for RHAMM binding to the mitotic spindle, which would result in dramatic inhibition of RHAMM function and lack of malignant cell survival.

c) Exogenous, infused HA may act to stimulate HAS1 isoenzyme variants by upregulating hyaluronidase, thus cleaving HA and causing the enzyme to be activated to make more intracellular HA, this would again increase the levels of intracellular HA, causing the balance of RHAMM/mitotic spindle association to tip in favor or cell death rather than cell survival.

d) Hyaluronidases, enzymes that cleave and degrade HA, have been detected inside cells (Fiszer-Szafarz B. et al. *Biol Cell* 63:355(1988), Kulyk W. M. et al. *Dev Biol* 120:535(1987)). Exposure to therapeutically administered HA is expected to stimulate hyaluronidases inside the cell, which in turn would be expected to cleave intracellular HA made by HAS1 variants, thus preventing the modulation of RHAMM. Exposure of cells to exogenous HA is known to upregulate hyaluronidases, which cleave HA to smaller fragments. All cells make hyaluronidases.

Synthesis of HA by HAS isoenzymes and isoenzyme variants is likely to occur in different cellular compartments from internalized, exogenous, HA (Evanko, S.P. et al. *J Histochem Cytochem* 47:1331(1999)). This may mean that simply infusing HA in the absence of HAS1 variants may not have the same outcome as infusing HA to patients whose malignant cells express HAS1 variants: exogenous HA may regulate synthesis of endogenous HA with different functional impacts.

Use of HAS Isoenzyme Variant Genes and Polypeptides Thereof.

The genes responsible for the synthesis of HA in mammals may be exploited, through various recombinant genetic and other techniques known in the art, to produce HA. See for example U.S. Pat. Nos. 6,602,693B1 and 6,492,150B1; herein incorporated by reference.

The novel isoenzyme variants of HAS1 disclosed herein, represented by SEQ ID NO:3 (HAS1Va), SEQ ID NO:5 (HAS1Vb) and SEQ ID NO:7 (HAS1Vc) and the amino acid sequences SEQ ID NO:4 (HAS1Va), SEQ ID NO:6 (HAS1Vb) and SEQ ID NO:8 9HAS1Vc); are novel enzymes capable of producing intracellular HA. Furthermore, these novel isoenzymes represent novel elements capable of producing HA in either the in vivo, as part of a gene therapy for example, or in vitro, as part of a synthetic process of HA for example.

In vivo gene therapies based upon the HAS1Va, HAS1Vb and/or HAS1Vc isoenzyme variants may include antisense expression of the genes resulting in down-regulation of natively expressed HAS1 isoenzyme variants, "sense" expression inside cells resulting in increased HA production arising from the HAS1 isoenzyme variants, or combinations thereof. In vitro synthesis of HA using the HAS1 isoenzyme variants can be expected to synthesize HA in a different manner from HAS1, HAS2, or HAS3 due to the missing elements within the HAS1 isoenzyme variant sequence.

The probes and primers disclosed in the present invention are useful for detecting the expression of the genes of the present invention; specifically the HAS1Va, HAS1Vb, HAS1Vc and related nucleic acid molecules. The uses, methods, processes and procedures of such detection as well as purification and preparation of said probes and primers disclosed herein are well known in the art and derived without undue experimentation. Techniques and methods for the selection and generation of probes and primers, other than those disclosed herein, specific to or selective for, the novel nucleotide sequences represented in SEQ ID NO:3, 5 and 7, are well known in the art and therefore derivation of additional probes and primers can occur without undue experimentation.

The present invention also provides for the resulting nucleic acids, complementary to the nucleic acids disclosed herein, including but not limited to niRNA transcripts, complementary probes, primers, small inhibitory RNA molecules or antisense nucleotides.

Conformational Properties of HAS1 Splice Variant Transcripts Predict Aberrant Protein Structure and Suggest Therapeutic Approaches The existence of pseudoknots, a secondary structure, of mRNA is one of the requirements for programmed "−1" ribosomal frameshift, which has been detected in the human immunodeficiency virus type 1 (HIV1) (Dulude, D. et al. *Nucleic Acid Res* 30:5094 (2002)). HIV1 uses a programmed "−1" ribosomal frameshift during translation of its mRNA to produce the precursors of viral enzyme. A similar phenomenon has been detected in several other retroviruses and in humans (Brierley, I., *J Gen Virol* 76:1885 (1995); Brierley, I. et al. *Cold Spring Harb Symp Quant Biol* 66:233 (2001); Ivanov, I. P. et al. *RNA* 4:1230 (1998); Ivanov, I. P. et al. *Genomics* 52:119 (1998); Shigemoto, K. et al. *Nucleic Acids Res* 29:4079(2001); Tzeng, T. H. et al. *J Virol* 66:999 (1992)). Because of the presence of pseudoknots, before peptide bond formation during the translation process, the translation resumes in the new reading frame which produces proteins with altered functions. Also, the incidence of pseudoknots in the transcripts of any given mRNA modulates frameshifting efficiency (Baril, M. et al. *RNA* 9:1246 (2003); Baril, M. et al. *J Mol Biol* 331:571 (2003)). Furthermore, pseudoknots can influence the frameshift through functional interactions with the ribosomes (Brunelle, M. N. et al. *Nucleic Acids Res* 27:4783 (1999)). The manipulation of "−1" ribosomal frameshifting can be achieved through using chemical agents such as: chloramphenicol, which interferes with peptide bond formation; spectinomycin which inhibits translocation; and/or peptidyl transferase inhibitors such as anisiomycin (Dinman, J. D. et al. *Proc Natl Acad Sci USA* 94:6606 (1997); Brunelle, M. N., et al. *Nucleic Acids Res* 27:4783 (1999)). Therapeutic alteration of "−1" ribosomal frameshifting is predicted to have a beneficial clinical impact by modulating the expression of HAS1 isoenzyme variants.

As mentioned above, truncated forms of HAS1 variants retain the central loop, which includes cysteine residues that are conserved among class 1 HASs (Table 1). Recently it has been shown that modification of these amino acid changes enzymatic activity of HASs (Kumari, K. et al. *J Biol Chem* 277:13943 (2002); Heldermon, C. D. et al. *Glycobiology* 11:1017 (2001)). Pummill et al. showed that certain cysteine residues play a significant role in substrate binding, catalysis, or enzyme folding (Pummill, P. E. et al. *J Biol Chem* 277:21610 (2002)). Modification of these amino acids can be successfully achieved by direct mutagenesis or using inhibitory reagent such as N-ethylmaleimide (Pummill, P. E. et al. *J Biol Chem* 277:21610 (2002)). Thus these cysteine residues are ideal therapeutic targets to achieve inhibition of HAS1 isoenzyme and isoenzyme variants.

The sequencing and next alignment analysis identified single nucleotide polymorphism (SNP) (T/C) in HAS1Va. The substitution of T with C caused amino acid modification in HAS1Va protein sequence, specifically proline is altered to serine. The serine amino acid is known to be substrate for phosphatases which phosphorylate the serine's hydroxyl groups (*Oxford Dictionary of Biochemistry and Molecular Biology*). Therefore, inhibition of phosphatases and/or modification of serine on HAS1Va by a direct mutagenesis approach can be used as therapeutic purposes in the treatment of diseases characterized by abberant HAS gene expression (Heldermon, C. D., et al. *Glycobiology* 11:1017 (2001)).

Microsystems and Cancer: Improved Detection of HAS and Disease Related Genes Using Microfluidics Platforms.

Understanding the risk factors for developing any type of cancer, including myeloma, will provide insight into strategies that may increase the length and quality of life for afflicted individuals. Identification of the genetic signature for each cancer is likely to enable predictions of risk and stratification of treatment. The capabilities of PCR and RT-PCR have accelerated progress in the measurement of molecular and genetic changes in patients, thus increasing identification of the genetic signatures of many types of cancers. The products obtained from RT-PCR are measured by gel-based analysis that frequently fails to detect low-level expressed genes or genes with shorter lifespan. Capillary electrophoresis, a more sensitive method, offers successful detection of low-level expressed genes. However, this method is time-consuming, expensive, and cannot be performed in routine clinical testing.

Integrated and automated microfluidic chips (MFCs, as distinct from microarray chips) offer an alternative means to measure molecular and genetic changes in patients when using, for example, diagnostic/monitoring tests such as RT-PCR, capillary electrophoresis, and/or fluorescent staining. These can be rapidly performed using minute amounts of tissue without specialized operators. Automated MFC platforms offer many advantages over existing macroscale systems: rapidity, compactness, disposability, reproducibility, and decreased sample volumes. We are using MFCs to develop novel Microsystems for fast, accurate and real time genetic screening of multiple myeloma (MM) patients. In MM, multiplex analysis of the clonotypic IgH VDJ signature and of accompanying genetic abnormalities offers the possibility for genetic profiling and monitoring. Comparative analysis confirms analysis of RT-PCR products on-chip is as sensitive—sometimes considerably more so—than conventional analysis of PCR products using capillary electrophoresis. On-chip PCR is robust, and less susceptible to contamination, than is conventional electrophoresis. On-chip sample processing, and the ability to detect product with few cycles of PCR, indicates that quantitative PCR is feasible. Detecting transcripts in single cells is feasible on-chip, which would enable analysis of clonal heterogeneity when diagnosing/monitoring cancer.

This work forecasts high-throughput automated devices able to analyze genetic information using minimal amounts of genetic material in minutes, inexpensively. Once fully integrated systems capable of seamless sample processing, selecting cells of interest and performing genetic analyses of individual cells or groups of cells are available for clinical use, we anticipate that they will contribute significantly at the time of diagnosis and facilitate monitoring genetic characteristics of the malignant clone at every subsequent clinic visit. Real time detection of complex genetic abnormalities in a given cancer clone is likely to detect aggressive variants as they arise and thus enable the development of therapeutic options tailored to the genetic signature of a cancer in each individual patient, at diagnosis and as cancer progresses.

The present invention is further described by the following examples.

EXAMPLES

Materials and Methods

All examples listed herein were performed using the following processes and methodologies, and refer to the following, except where otherwise stated.

Patients

Blood and/or bone marrow samples from patients with multiple myeloma, monoclonal gammopathy of undetermined significance (MGUS), and lymphoma were taken at the time of clinical visit. Specific cell subpopulations were stained with fluorescent tagged antibodies and the cells that bound the antibody were purified using flow cytometry and cell sorting. $CD19^+$ B cells were obtained from the peripheral blood of patients with MM, MGUS, and healthy donors, while $CD38^{hi}CD45^{lo}$ PC were collected from the BM aspirate of patients with MM and lymphoma.

Reagents

FMC63 (anti-CD19) was conjugated with flurorescein isothiocyanate (FITC). To detect other cell surface antigens, cells were stained with anti-CD38 (Leu-17-phycoerythrin (PE)), anti-CD45-FITC, Goat anti-mouse Ig and Goat anti-human Ig (goat-human Ig [H+L]) conjugated to FITC or PE (FITC and PE were purchased from Becton Dickinson and Southern Biotechnology respectively).

Tissue and Cell Preparation

The peripheral, venous, blood from patients was immediately collected into heparinized tubes and further purified on a Ficoll-Hypaque gradient (GIBCO/BRL; Burlington, Ontario, Canada). The mononuclear cells (MC) were harvested from the interface of the Ficoll density gradient washed twice, and re-suspended in phosphate-buffered saline (PBS). Next, >20×10$^6$ cells were stained with -CD19 (FMC63-FITC) (PBMC) or -CD38 (Leul7-PE) and -CD45 (FITC) (BM cells) for 30 min at 40C. For isotype controls, the cells were stained with human IgG2a-FITC or IgG1-PE. After staining, the cells were washed twice with 0.2% EDTA/PBS to inhibit cell agglutination. Mononuclear cells were high speed sorted on a Coulter Elite Altra flow cytometer. CD19$^+$ B cells from the peripheral blood of patients with MM and MGUS were sorted by setting a gate beyond the IgG2a isotype control and back gating to small and large lymphocyte populations, while in case of sorting CD19$^+$ B cells obtained from healthy donors only small populations of lymphocytes were gated. Setting a gate on forward (FS), and side, scatter (SS) eliminated the cellular debris and dead cells in the samples. The BM PC of patients with MM were sorted as a CD38$^{hi}$CD45$^{lo}$ cells and then the gate was back gated on forward and side scatter (FS vs. SS). Sort gates were set to include cells with a fluorescence intensity brighter than that of the isotype-matched control antibodies. Sorted samples had >96% purity on reanalysis by flow cytometry. The sorted cells were collected directly into FBS and then washed and re-suspended in Trizol (GIBCO/BRL) or RLT lysis buffer (Qiagen) for total mRNA isolation Next, the samples were stored at −80° C. until use. Furthermore, unfractionated BM cells and PBMC from >200 MM patients were re-suspended in Trizol for total mRNA isolation, which was performed according manufacturer's directions.

Reverse-Transcriptase Polymerase Chain Reaction (RT-PCR)

cDNA for the PCR reactions was reverse-transcribed from total mRNA isolated from sorted CD19$^+$ B cells and CD38$^{hi}$CD45$^{lo}$ PC or unfractionated PBMC and BM cells using either a standard Trizol (GIBCO/BRL) isolation reaction or RNeasy kit (Qiagen), according to the manufacturer's instructions. Isolated RNA was re-suspended in RNAase-free water. The concentration of RNA was determined by absorbance at 260 mn, and samples were sorted at −80° C. After thawing, mRNA (0.5-1 µg) was denatured for 10 minutes at 70° C. followed by annealing 1 µl of the universal primer oligo dT15 (10 µM) in 11 µL the total volume of the reaction. Next, RNA was reverse-transcribed with 1 µl of 10 mM deoxyribonucleoside triphosphates (dNTP's), 1 µl of 0.1 M dithiothreitol (DTT), 1 µl of 40 U/1 RNAase inhibitor, 1 µl of 200 U/µl superscript (GIBCO/BRL), and 5× superscript buffer in a total volume of 20 µl reaction at 42° C. for 60 minutes and heat-activated for 3 minutes at 99° C.

The cDNA obtained from the reverse transcriptase reaction was amplified by a reverse and forward primer set for each isoenzyme of HAS—HAS1, (SEQ ID NO:15 and SEQ ID NO:16) HAS2, (SEQ ID NO:11 and SEQ ID NO:12) and HAS3, (SEQ ID NO:13 and SEQ ID NO:14). From these primer sets, the 5' primers were labeled at their 5' ends with 6-carboxyflourescein (FAM) (Applied Biosystems). PCR reaction was performed under the following condition: 1 µl cDNA was added to 24 µl of PCR mix containing 2.5 µl of 10×PCR buffer, 1 µl of 50 mM MgCl$_2$, 0.5 µl of 10 mM dNTPs, 1 µl each of 10 µM primers and 0.5 µl of 5 U/µl platinum Taq (GIBCO/BRL). The PCR cycling parameters were the following: primary denaturation for 5 minutes at 94° C., denaturation for 30 seconds at 94° C. 35 cycles, annealing for 30 seconds at 60° C., extension for 30 seconds at 72° C. and final extension for 7 minutes at 72° C. The samples were either stored at −20° C. or processed for the capillary electrophoresis on 3100 DNA genetic analyzer.

Capillary Electrophoresis-DNA Fragment Analysis (GeneScan Analysis)

For GeneSan analysis 1 µl of PCR product was mixed with a loading buffer, 12 µl of formamide and 1 µl of internal size standard GeneScan 500 [TAMRA] and GeneScan 500 [LIZ] (Applied Biosystems). Next, PCR products were denatured for 4 minutes at 96° C. and after quick spin, samples were transferred immediately to ice for 15 minutes. Samples were separated on the ABI3100 genetic analyzer using capillaries filled with POP4 polymer (Applied Biosystems). The electrophoresis conditions were the following: a run voltage and injection voltage 15000 volts, injection duration 6-10 seconds, a temperature 60° C., and a laser within power of 9 milliwatts. The results of capillary electrophoresis were analyzed using GeneScan software (Microsoft).

Cloning and Sequencing mRNA for cloning was extracted using an RNAeasy kit (Qiagen). Next, 1 µg of mRNA was reverse transcribed as above. HAS1 was amplified in a 50 µl PCR reaction mix containing 8 µl cDNA, 5 µl of 1× PCR buffer, 2 mM MgSO$_4$, 0.2 mM dNTP's, 0.4 µM HAS1 primer set (SEQ ID NO:15 and SEQ ID NO:16) and 0.5 U Platinum Hi Fl Taq (GIBCO/BRL). The PCR cycling parameters were denaturation for 5 min at 94° C., followed by 35 cycles of denaturation for 1 min at 94° C., annealing for 2 min at 60° C. and extension at 72° C. for 2 min, with a final extension period of 7 minutes at 72° C. HAS1 PCR products were cloned into the PCR-4-TOPO-TA cloning system and transformed into TOPO10 competent cells according to the manufacturer's instructions (Invitrogen, Life Techologes, Inc). To identify which bacterial colonies contained HAS1 plasmid, individual bacterial colonies were introduced into a PCR reaction mix containing 1× PCR buffer, 2 mM MgCl$_2$, 0.2 mM dNTP's, 0.5 U Taq DNA Polymerase (GIBCO/BRL) and 0.4 µM HAS1 forward and reverse primers. The PCR cycling parameters were bacterial lysis for 10 minutes at 94° C., followed by 25 cycles of denaturation for 30 seconds at 94° C., annealing at 60° C. for 1 minute, and extension at 72° C. for 1 minute, with a final extension period of 7 minutes at 72° C. The amplified products were analyzed by agarose gel electrophoresis, HAS1/PCR-4-TOPO-TA positive colonies were identified and grown overnight in LB medium containing 10 µg/ml ampicillin. Plasmids were prepared with the Qiagen Plasmid Mini Kit and sequenced with T7 and M13 primers with the ABI PRISM BigDye V3 Cycle Sequencing Ready Reaction DNA Sequencing Kit on a Perkin Elmer 310 DNA Genetic Analyzer.

Patients Clinical Data and Statistics

The peripheral blood (PB) and BM samples were collected, after informed consent, from 130 MM patients between December 1995 and November 2001. Information on diagnosis, patient demographics, baseline staging and clinical features, treatment, response to therapy, progression and survival were collected. For this study PB and BM from the time of diagnosis were both available from 29 cases; BM only was available from 41 cases. For WM, blood and/or bone arrow samples were taken at the time of regular clinic visits from 12 patients.

Data for the statistical analysis were analyzed using SAS version 8.2 for windows (SAS Inc., Cary, N.C.) and GraphPad Prism version 3.02 for Windows (GraphPad software, San Diego Calif.). Categorical variables were compared between two groups using Fisher's exact test. Continuous variables were compared using Student's t-test or the Wilcoxon rank sum test as appropriate. Survival distributions were determined using the Kaplan Meier method and compared using the log rank test. Multivariable analysis and hazard ratios were generated using Cox regression models. Statistical significance was set at a p-value of 0.05 using two-sided analysis.

Particle Exclusion Assay

Particle exclusion assay was used to determine the enzymatic activity of HAS proteins encoded by HAS isoenzymes expressed in the B cells of patients with MM, MGUS and normal donors B cells and the BM PC of patients with MM. The method followed the procedure previously described (Knudson, W. et al. J Cell Sci: 99:227 (1991)). Briefly, sorted $CD19^+$ B cells ($2\times10^6$), obtained from the peripheral blood of patients with MM and a normal donors, and $CD38^+$ PC ($2\times10^6$), collected from the bone marrow aspirated of patients with MM, were washed with calcium/magnesium free PBS (CMF-PBS) and re-suspended in a DMEM or RPMI (GIBCO-BRL) medium containing 10% FBS. The cells were cultured in a Poly-L-Lysine (1 mg/ml; Sigma) coated 35 mm culture dish and allowed to recover. After the recovery time, the 4 h, 12 h, 24 h, and 48 h, medium was removed and the cells were washed with CMF-PBS. Next, formalin (3% final concentration) fixed sheep erythrocytes ($50\times10^5$) in PBS containing 0.1% BSA were added to the cultured cells. The culture dish was placed on the microscope stage and was not disturbed until the fixed red blood cells had settled (30-45 minutes). The images were taken using an Axiovert 100M (Zeiss) confocal laser-scanning microscope. As a negative control, the cells were treated with 100 μl (500U/ml) of hyaluronidase (HAase—Type-4s from bovine testes; Sigma) for 1 h at 37° C. prior to adding fixed erythrocytes.

The particles used in the particle exclusion assay were isolated from whole sheep blood by centrifugation and the resulting pellet was washed 3 times with CMF-PBS. The final cell suspension was fixed with 3% formalin, the cells were shaken overnight at room temperature, and fixed cells were washed 4 times with CMF-PBS. Next, the cells were re-suspended in CMF-PBS, and before use, the cell suspension was diluted in CMF-PBS containing BSA at a final concentration of 1 mg/ml.

The Particle Exclusion Assay in Combination with HA Staining

The Particle Exclusion Assay was modified and combined with indirect HA staining to verify that the detected pericellular matrix around the cell plasma membrane includes HA molecules. The sorted $CD19^+$ or $CD38^+$ cells ($2\times10^5$) were cultured in Poly-L-Lysin (PLL) coated 35 mm dish in a IMDM or RPMI medium (GIBCO-BRL) containing 10% FBS. Next, the cells were allowed to recover for 4, 24, and 48 h. After the recovery time, the cells were washed with PBS, fixed with 1% paraformaldehyde and rinsed 3× with PBS. To localize HA, the cells were incubated with biotinylated HA binding protein (HABP; Seikagaku Corp.) 2 μg/ml in PBS containing 1% BSA over night at room temperature. The cells were then washed with PBS to remove nonspecific binding. Alternatively, the biotinylated HABP was detected with streptavidin Alexa Fluor 633 (1:500 dilution for 2 h. at room temperature; Molecular Probes).

As a negative control some sorted cells were treated with 100 μl of 500 U/ml hyaluronidase for 1 h at 37° C. or biotinylated HABP were pre-incubated with 100 μg Hyaluronan. The specificity of streptavidin was detected by staining the cells with streptavidin Alexa Fluor 633 only. The cells were examined with an Axiovert 100M (Zeiss) confocal laser-scanning microscope.

On-chip PCR (Microfluidics)

cDNA for the PCR reactions was reverse-transcribed from total mRNA isolated from sorted $CD19^+$ B cells using RNeasy kit (Qiagen) according to the manufacturer's instructions. Isolated RNA was re-suspended in RNAase-free water. The concentration of RNA was determined by absorbance at 260 nm, and samples were sorted at −80° C. After thawing, mRNA (0.5-1 μg) was denatured for 10 minutes at 70° C. followed by annealing 1 μl of the universal primer oligo dT15 (10 μM) in 11 μl the total volume of the reaction. Next, RNA was reverse-transcribed with 1 μl of 10 mM deoxyribonucleoside triphosphates (dNTP's), 1 μl of 0.1 M dithiothreitol (DTT), 1 μl of 40 U/ml RNAase inhibitor, 1 ml of 200 U/μl Superscript® (GIBCO/BRL), and 5× superscript buffer in a total volume of 20 μl reaction at 42° C. for 60 minutes and heat-activated for 3 minutes at 99° C. The cDNA obtained from RT reaction was amplified by primer represented by SEQ ID NO:9 and SEQ ID NO:10. From these primer sets, the 5' primers were labeled at their 5 ends with 6-carboxyflourescein (VIC) (Applied Biosystems). 2 μl PCR reaction mix (PCR reaction mix contained: 1 μl cDNA was added to 24 μl of PCR mix containing 2.5 μl of 10× PCR buffer, 1 μl of 50 mM $MgCl_2$, 0.5 μl of 10 mM dNTPs, 1 ml each of 10 μM primers and 0.5 μl of 5 U/μl platinum Taq (GIBCO/BRL) was loaded on the automated microfluidics chip and reaction was performed under following conditions: primary denaturation for 5 minutes at 94° C., denaturation for 30 seconds at 94° C. 35 cycles, annealing for 30 sec. at 60° C., extension for 30 sec. at 72° C. and final extension for 7 minutes at 72° C. The 0.9 μl of PCR product was retrieved from the chip and analyzed for the capillary electrophoresis on 3100 DNA genetic analyzer. For GeneSan analysis of microfluidics chip-based PCR, 0.9 ml of PCR product was mixed with a loading buffer, 12 ml of formamide and 1 ml of internal size standard GeneScan 500 [LIZ] (Applied Biosystems). Next, PCR products were denatured for 4 minutes at 96° C. and after quick spin, samples were transferred immediately to ice for 15 minutes. Samples were separated on the capillary filled with POP4 polymer (Applied Biosystems). The electrophoresis conditions were the following: a run voltage and injection voltage 15000 volts, injection duration 8-10 seconds, a temperature 60° C., and a laser within power of 9 milliwatts. The results of capillary electrophoresis were analyzed using GeneScan software (Microsoft).

Example 1

Novel Splice Variants of Hyaluronan Synthase 1 in Multiple Myeloma (MM)

To examine the role of hyaluronan synthases (HASs); HAS1, HAS2, and HAS3; in MM, we determined the expression pattern of HASs in MM B and PC.

Figure 2:
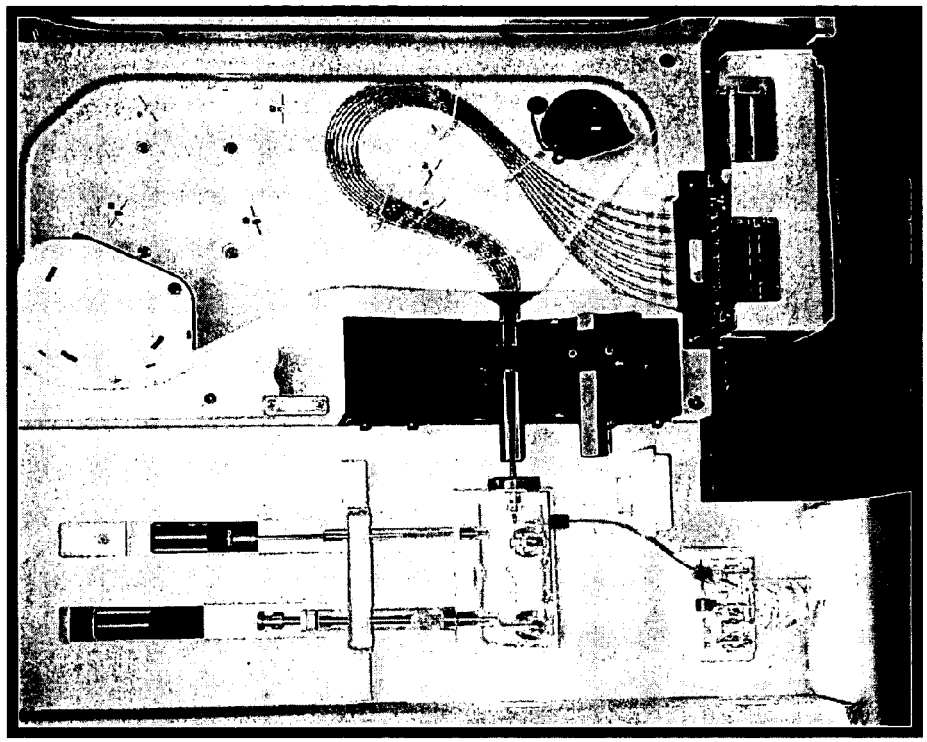
FIG. 2. Detection of HAS1 and its novel variants transcripts in MM patients. Diagramatic depiction of the detection and analysis of HAS isoenzyme and isoenzyme variant expression in MM patients using RT-PCR DNA Fragment Analysis.
Figure 2:
Figure 2:
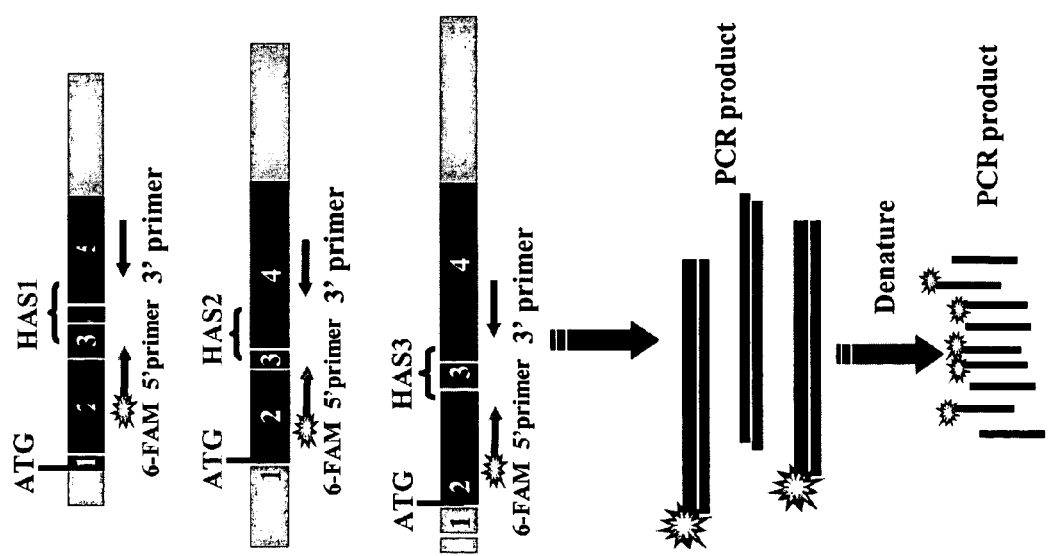

The expression profiles of the HAS genes were analyzed using RT-PCR and detected by a DNA fragment analysis approach in which gene transcription is assessed by detecting changes in the amplified fragments generated from HAS specific primers in a RT-PCR reaction. FIG. 1 depicts expression of HAS1 and its novel isoenzyme variants detected using RT-PCR and DNA fragment analysis approach (FIG. 1). In PCR reactions 5' primers were fluorescently labeled. Total RNA from B and PC were immediately isolated after cell sorting procedure. The X-axes represent molecular size (bp) of PCR product and the Y-axes Relative Fluorescent Units (RFU), with internal size standards and HAS specific peaks present along with PCR product. The PCR reaction was performed using 5' fluorescently labelled primers specific for each of the HAS genes followed by capillary electrophoresis on the ABI 3100 DNA analyzer (Applied Biosystems, U.A.) (FIG. 2).

Figure 3A:
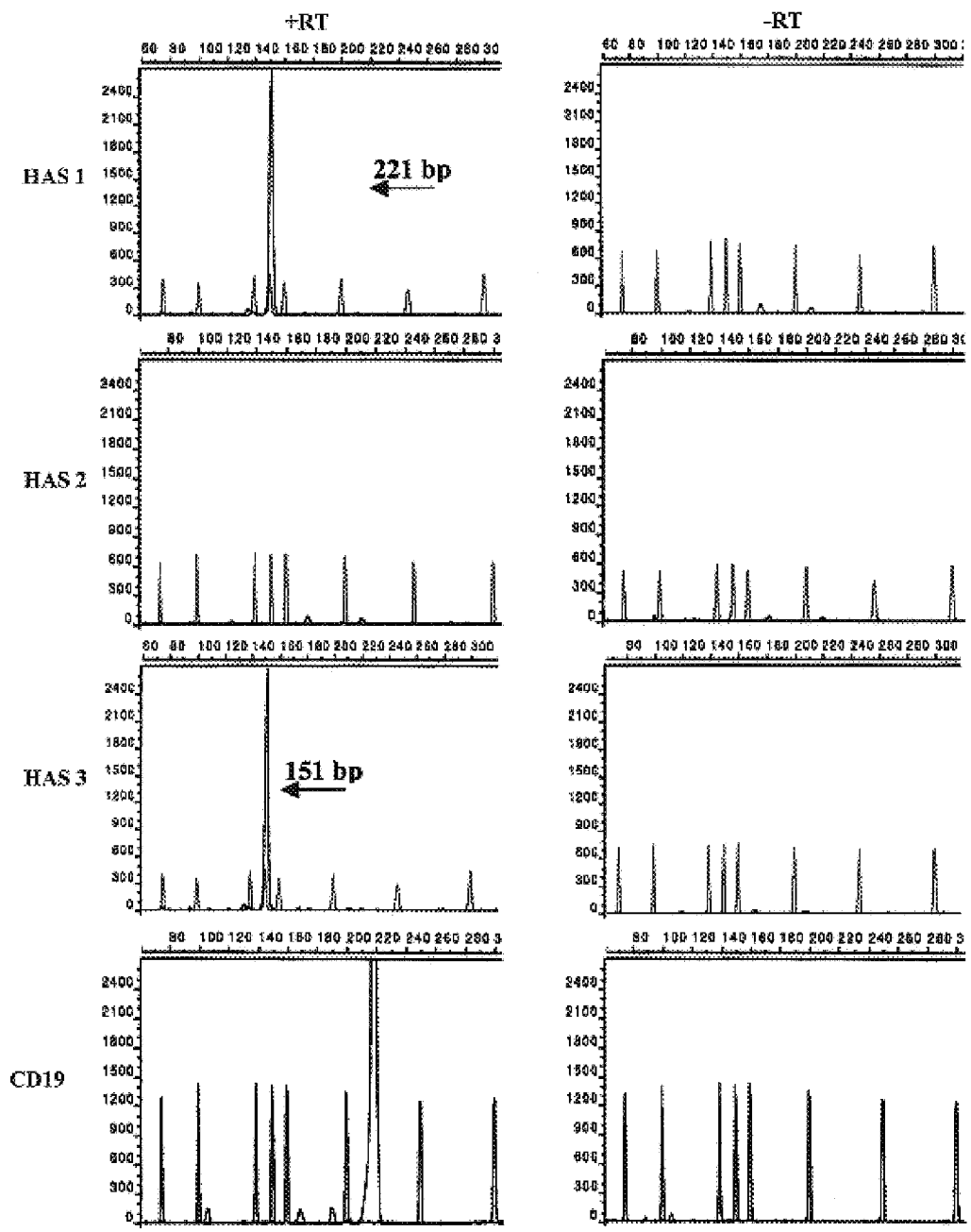
FIG. 3a. Analysis of peripheral blood B-cells. RT-PCR specific amplification of nucleotide products derived from cellular mRNA of peripheral blood collected from MM patients, in which HAS1 and HAS3 isoenzyme specific peaks are observed.

RT-PCR DNA fragment analysis revealed cell-type specific expression of HAS1 and HAS2 in MM B and PC. FIG. 3a shows a DNA fragment analysis electropherogram of PCR products obtained by the amplification of mRNA isolated from B cells of the peripheral blood (PB) collected from MM patients, showing that CD 19$^+$ B cells obtained from MM patients' PB express HAS1 and HAS3 transcripts (FIG. 3a). The x-axes represent molecular size (bp) of PCR product and the y-axes Relative Fluorescent Units (RFU), with internal size standards present along with PCR product. No HAS2 transcripts were detected in MM CD 19$^+$ B cell. Expression of CD19 transcripts were used to evaluate integrity of the total RNA isolated mentioned cell type.

Figure 3B:
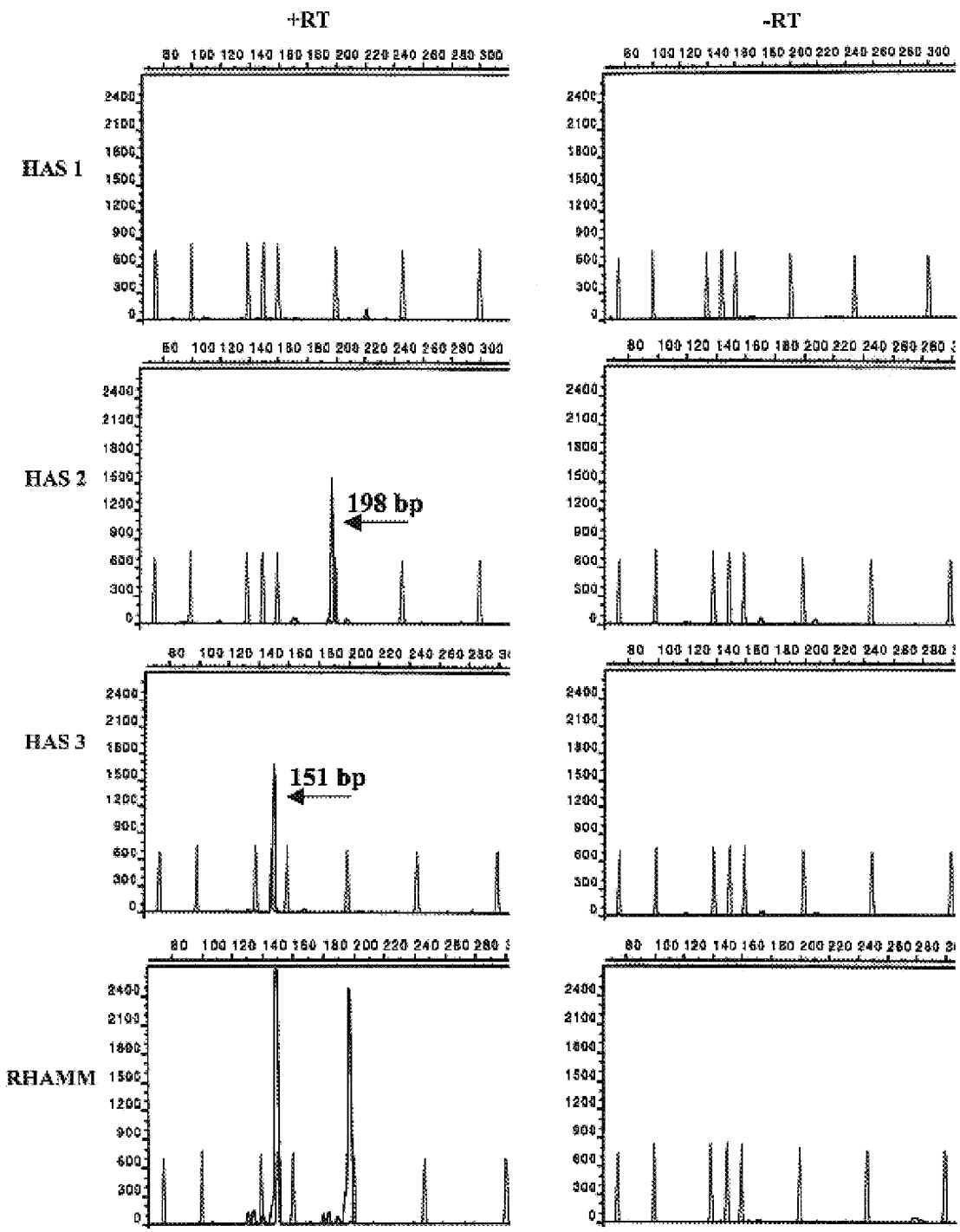
FIG. 3b. Analysis of bone marrow plasma cells. RT-PCR specific amplification of nucleotide products derived from cellular mRNA of bone marrow plasma cells collected from MM patients, in which HAS2 and HAS3 isoenzyme specific peaks are observed with no HAS1 isoenzyme specific peaks detected.

FIG. 3b shows a DNA fragment analysis Electropherogram of PCR products obtained by the amplification of mRNA isolated from BM PC from patients with MM, showing that CD38$^{hi}$CD45$^{lo}$ PC obtained from MM patients' BM aspirates express HAS2 and HAS3 transcripts (FIG. 3b). No HAS1 transcripts were detected in CD38$^{hi}$CD45$^{lo}$ PC. Expression of RHAMM transcripts were used to evaluate integrity of the total RNA isolated mentioned cell type. All tested patients and healthy donors ubiquitously express HAS3 transcripts.

Figure 4A:
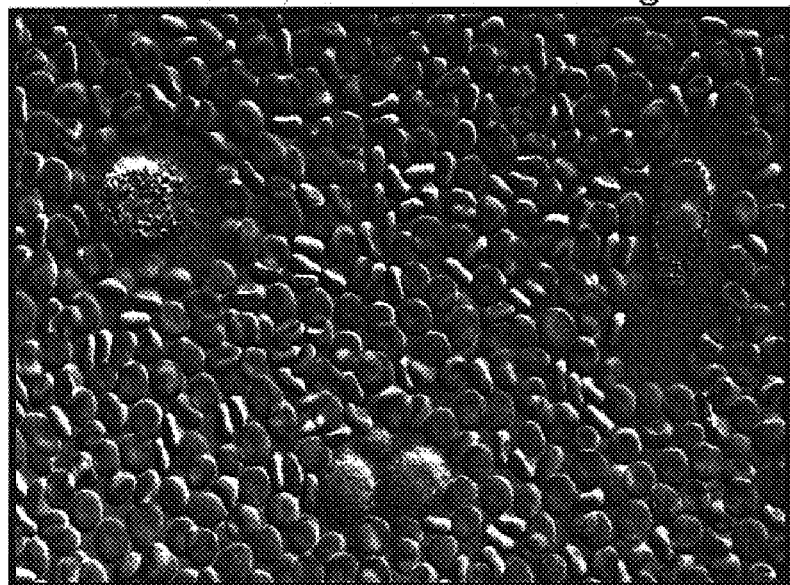
FIG. 4a. Visualization HA pericellular matrix. Micrograph obtained from a particle exclusion assay allowing identification of HAS isoenzyme enzymatic activity in B-cells obtained from Multiple Myeloma patients.
Figure 4A:
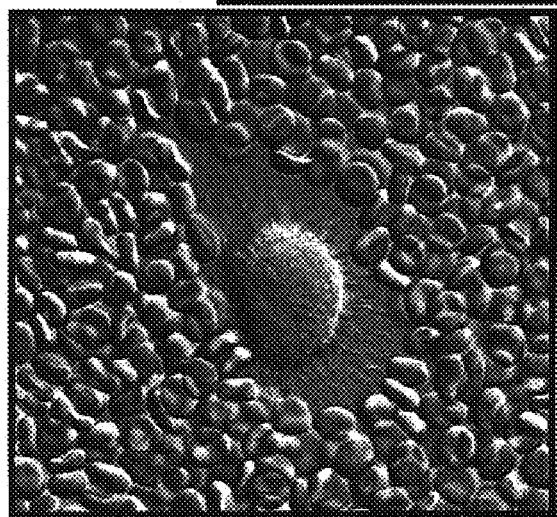
Figure 4A:
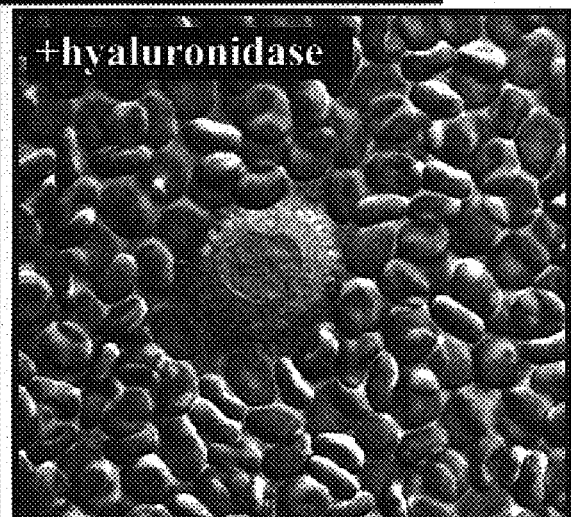

MM B cells, which express HAS1, synthesize extracellular HA halos, as confirmed by particle exclusion assay combined with indirect HA staining. FIG. 4a shows the results of a particle exclusion assay, used to determine the enzymatic activity of HAS proteins encoded by HAS isoenzymes expressed in the B cells of patients with MM, 48 h after culturing (Knudson, W. et al. J Cell Sci: 99:227 (1991)) (FIG. 4a). The images were taken using an Axiovert 100M (Zeiss) confocal laser-scanning microscope. As a negative control, the cells were treated with 100 μl (500 U/ml) of hyaluronidase (HAase—Type-4s from bovine testes; Sigma) for 1 h at 37° C. prior to adding fixed erythrocytes. FIG. 4a shows cells with extracellular matrix around their plasma membrane and cells without matrix (Top; second row left). After Hyaluronidase treatment cell lost extracellular matrix (second row right).

Figure 4B:
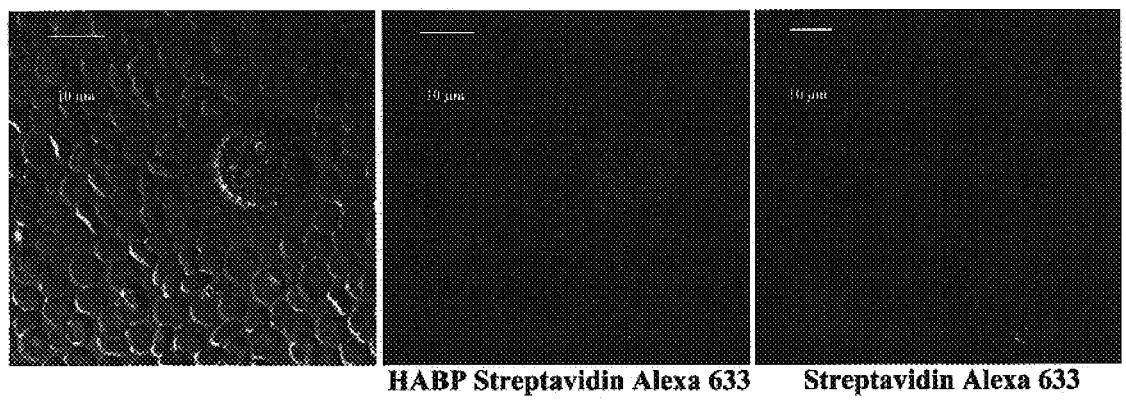
FIG. 4b. Visualization HA pericellular matrix in combination with HA specific staining. Micrograph confirming the pericellular matrix observed in particle exclusion assay includes hyaluronic acid molecules.

FIG. 4b shows the Particle Exclusion Assay modified and combined with indirect HA staining, to verify that the detected pericellular matrix around the cell plasma membrane includes HA molecules (FIG. 4b). The specificity of streptavidin was detected by staining the cells with streptavidin Alexa Fluor 633 only (far left image). The cells were examined with an Axiovert 100M (Zeiss) confocal laser-scanning microscope.

No HA halos were detectable for MM plasma cells nor for B cells from healthy donors. This suggests that HAS1 may be an important component of malignant spread as only MM B cells have migratory capability on HA (see below).

Figure 5A:
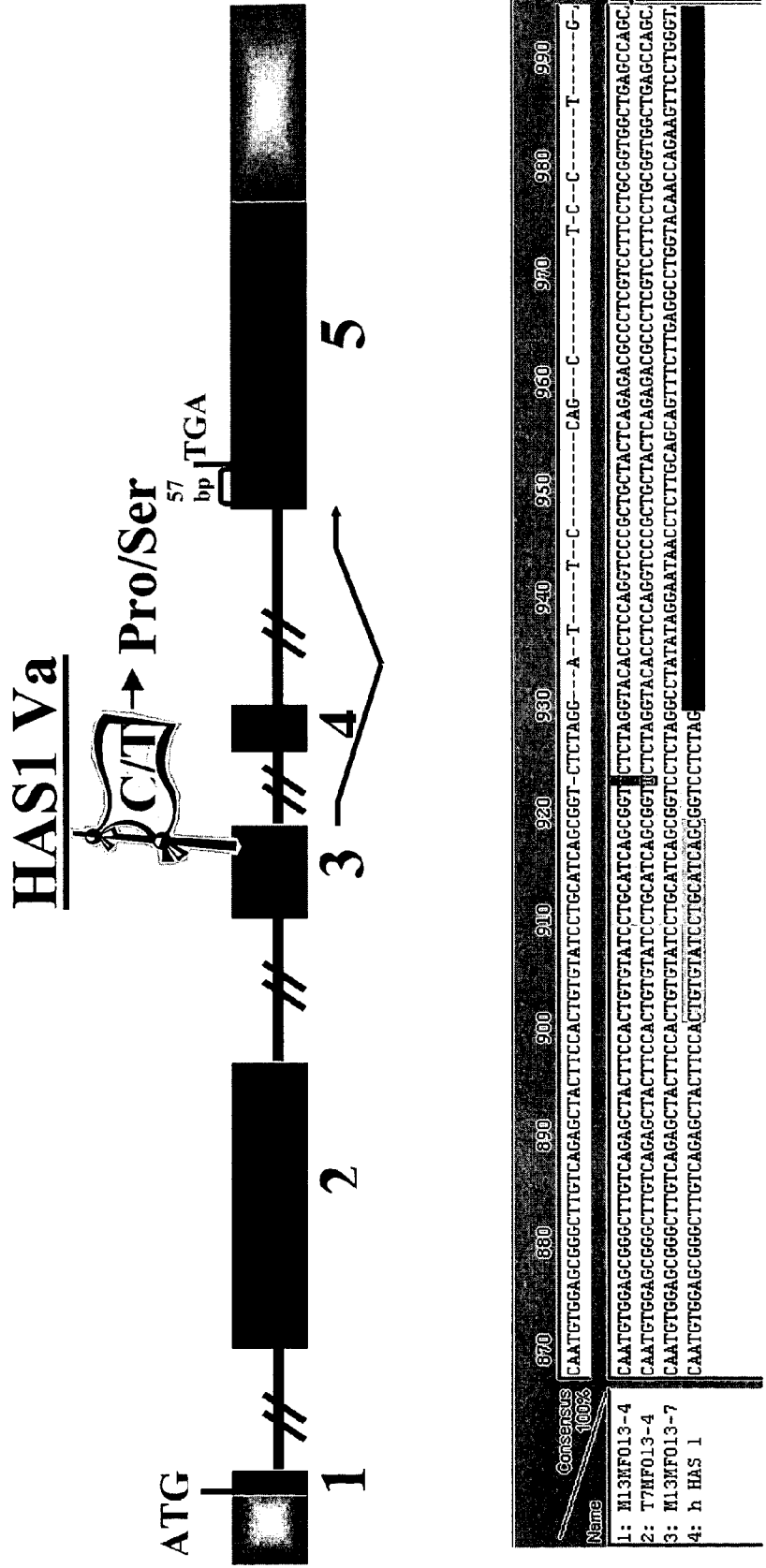
FIG. 5a. HAS1Va novel splice variant of HAS1, SEQ ID NO:1. Representation of the HAS1Va isoenzyme variant, including deduced splice sites and alignment analysis of observed HAS1Va isoenzyme variant with the native, full length, HAS1.
Figure 5B:
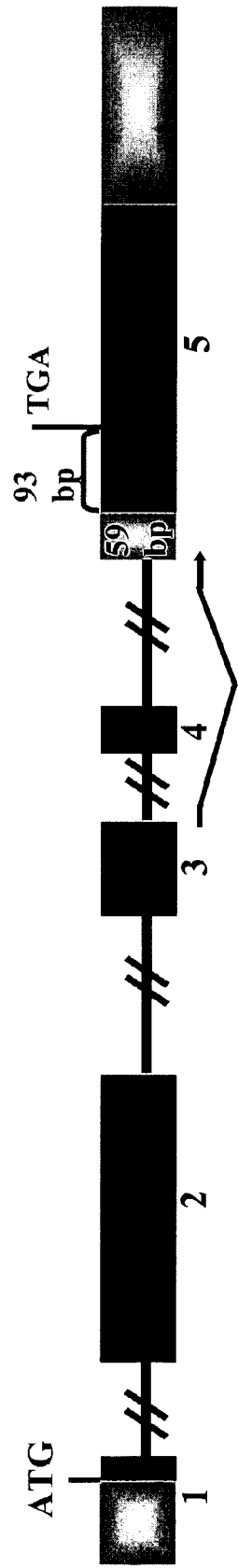
FIG. 5b. HAS1Vb novel intronic splice variant of HAS1. Representation of the HAS1Vb isoenzyme variant including deduced splice sites.
Figure 5C:
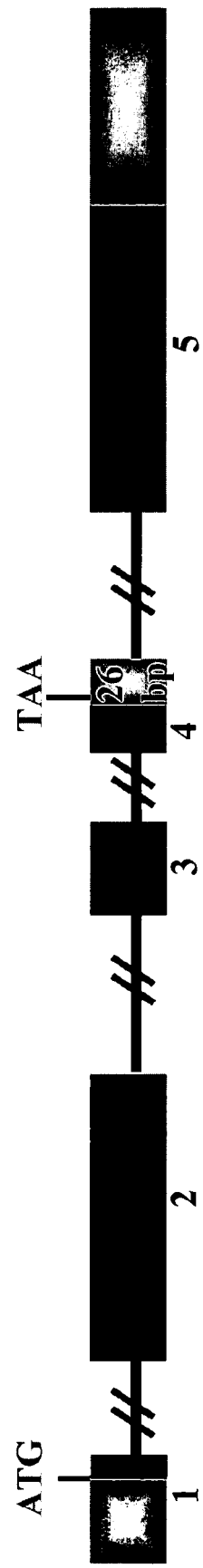
FIG. 5c. HAS1Vc novel intronic splice variant of HAS1. Representation of the HAS1Vc isoenzyme variant inlcluding deduced splice sites.

We identified three novel splice variants of HAS1; HAS1Va, HAS1Vb and HAS1VC; which were detected in MM BM and PB (FIG. 5a). Figure 5a depicts HAS1Va, the result of splicing of exon 4 causing insertion of premature termination codon (PTC) 57 bp downstream of the deleted exon 4. FIG. 5a also depicts a single nucleotide polymorphism detected on exon 4 which cause substitution of Proto-Serine; and also shows alignment analysis of nucleotide sequenced HAS1Va plus (1: M13 MFO13-4), minus (2:T7MFO13-4) strands and HAS1$^{FL}$ (3: MFO13-7) isolated from same MM patient with Human HAS1$^{FL}$ (from NCBI). HAS1Va gene encodes a 329 amino acid long 35.91KD protein (calculated using ExPASy—Translate tool software). FIG. 5b depicts HAS1Vb, the result partial retention of intron 4 (59 bp) and deletion of the entirety of exon 4 similar to HAS1Va (FIG. 5b). The partial retention of intron 4 and deletion of exon 4, leads to an in-frameshift and results in a PTC 93 nucleotides downstream of retained intron 4. HAS1Vb transcript encodes a 361 amino acid long 39.52KD protein (size calculated using ExPASy—Translate tool software). FIG. 5c depicts HAS1Vc, which is similar to HAS1Vb, the result of retention of intron 4 (26 bp). Unlike the other isoenzyme variants of HAS1, HAS1Vc retains exon 4. Retention of intron 4 caused insertion of PTC at the end of exon 3. HAS1Vc transcript encodes a 354 amino acid long 36KD protein (size calculated using ExPASy—Translate tool software).

HAS1Va is overexpressed in malignant cells and is detected at comparable frequency amongst MM patients in their PB and BM cells. HAS1Vb is a result of abnormal intronic splicing which leads to a frameshift. In contrast to HAS1Va, expression of HAS1Vb appears to be restricted to circulating malignant cells in MM PB. cDNA sequence for HAS1, SEQ ID NO: 1 (previously known in the art) and the novel HAS1Va (SEQ ID NO:3), HAS1Vb (SEQ ID NO:5) and HAS1Vc (SEQ ID NO:7) has been determined; with their respective amino acid sequence (SEQ ID NO:2, SEQ ID NO:4, SEQ ID NO:6 and SEQ ID NO:8, respectively).

HAS1Vb derives from MM B cells, as shown by our detection of HAS1Vb in purified MM PB B cells and its absence from MM PB T cells and MM BM PC, raising the possibility that relatively rare expression of HAS1Vb in the BM may derive from BM B cells rather than PC. The highly significant association between PB HAS1Vb and poor survival, and the rare and/or no detection of this variant in the BM supports this view. HAS1Vb is first prognostic marker described that reflects properties of circulating malignant MM B cells. Thus, this finding provides further evidence in support of a key role for early stage MM cells in malignant progression, suggesting potential mechanisms through which MM B cells may impact disease progression. The clinical correlations identified here support the idea that overexpression of HAS genes, and the unusual HAS1 splicing patterns that are largely restricted to malignant cells, play an important role in disease progression in multiple myeloma.

Figure 6:
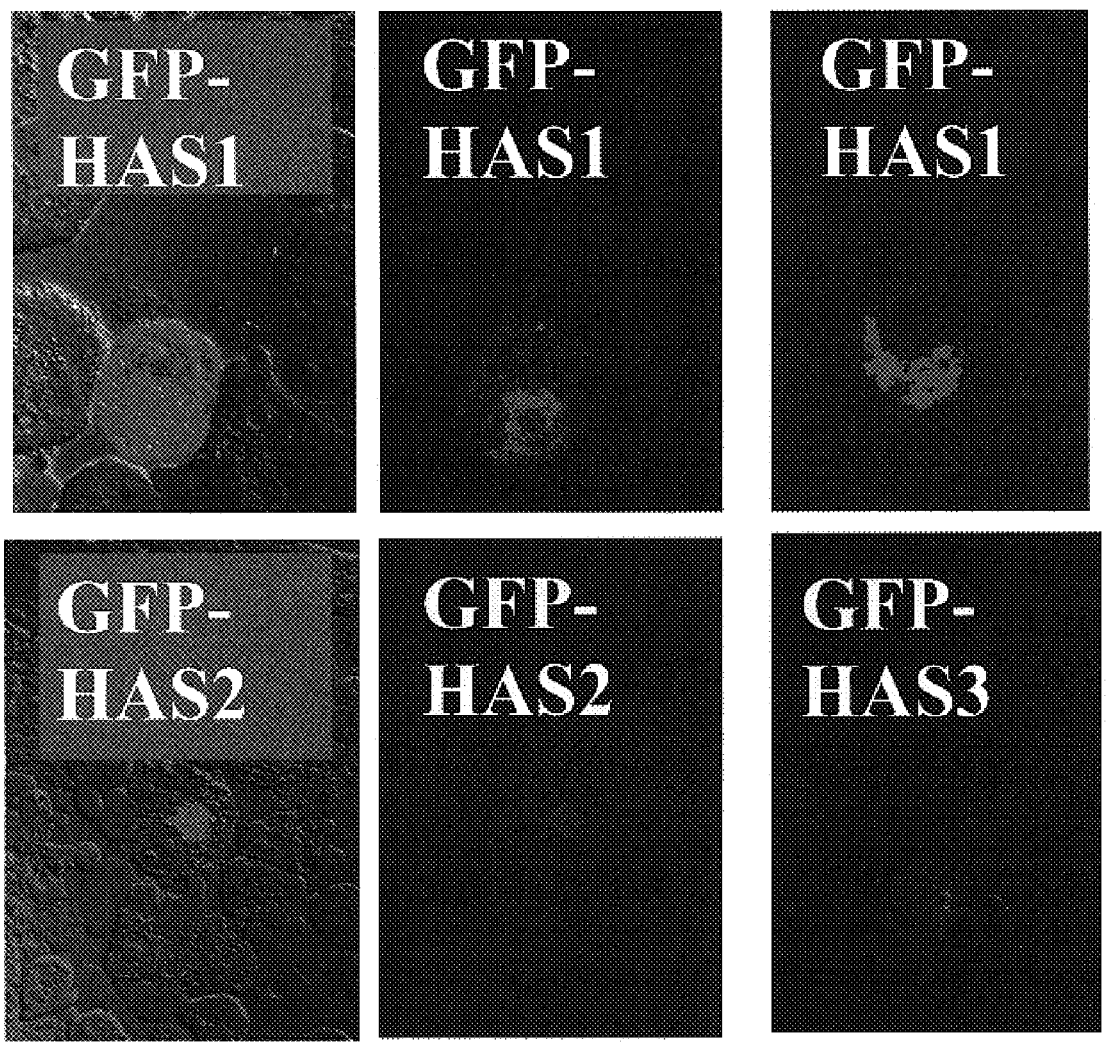
FIG. 6. Localization of HA produced by cells transfected with HAS isoenzyme. Micrograph showing detection of HA production in COS cells transfected with GFP-HAS1, GFP-HAS2 and GFP-HAS3 constructs.

Transfection analysis of GFP-HAS(s) constructs in the COS cell line showed different localization patterns of HAS1, HAS2 and HAS3 proteins. HAS2 and HAS3 appear-to be surface localized isoenzymes with possibly small amounts of intracellular localization. In contrast, HAS1 is abundantly located inside the cell with weak surface localization. The presence of HAS1 inside the cell is consistent with its postulated role in modulating intracellular functions of RHAMM and other intracellular components that bind HA, through synthesis of intracellular HA as shown FIG. 6 shows COS cells transfected with GFP-HAS1, GFP-HAS2 and GFP-HAS3 constructs (donated by Dr. Spicer) 48 hours after transfection; transfected COS cells were examined with an Axiovert 100M (Zeiss) confocal laser-scanning microscope (FIG. 6).

The claim that HAS gene expression modulates intracellular function, impacting genetic instability, is supported by the observation that the circulating clonal B cells in myeloma patients are extensively DNA aneuploid with, on average, 1.07 excess DNA content (Pilarski, L. M. et al. *Clin Cancer Res* 6:585 (2000)), 7% excess DNA is equivalent to the amount of DNA in an additional 3.2 chromosomes, evidence for extensive genetic instability in the malignant B cells that overexpress HAS1 and its variants.

Example 2

Further Examination of HAS Gene Expression in MM Patients.

In order to elucidate the differential effects of HAS isoenzymes on MM oncogenesis, the expression pattern of HASs were examined in MM, monoclonal gammmopathy of undetermined significance (MGUS), and chronic lymphocytic leukemia (CLL) CD9$^+$B cells, MM bone marrow plasma cells (PC, defined as CD38$^{hi}$CD45$^{lo}$ cells), and B cells obtained from healthy donors (Table 2a,b). Through RT-PCR and a highly sensitive DNA fragment analysis using the ABI 3100 genetic analyzer and GeneScan software, we have detected a cell-type specific expression pattern of HAS genes in CD19$^+$B cells obtained from patients with MM (13 patients), MGUS (4 patients) and healthy donors (10 donors), and MM (11 patients) CD38$^{hi}$CD45$^{lo}$ PC (Table 2a,b). This analysis shows that HAS3 gene is ubiquitously expressed in all tested MM and MGUS patients and in all analyzed healthy donors (not shown).

TABLE 2a

Expression of HASs in PB CD19$^+$ B cells and BM PC obtained from MM patients

|  | HAS1Va | HAS1Vb | HAS1Vc | HAS1 | HAS2 |
|---|---|---|---|---|---|
| BM PC cells (n = 11) | 9% | 9% | NA | 27% | 100% |
| Neg. CD38-CD45-PC Cells (n = 3) | 0% | 0% | 0% | 0% | 0% |
| CD19$^+$ B cells (n = 13) | 62% | 54% | 46% | 54% | 0% |
| Neg. (CD19−) cells (n = 9) | 0% | 0% | 0% | 0% | 0% |

NA = Not analyzed

TABLE 2b

DNA Fragment Analysis

|  | HAS1Va | HAS 1 | HAS 2 | HAS 3 |
|---|---|---|---|---|
| Healthy Donor B | 0/10 | 0/10 | 0/10 | 10/10 |
| MGUS B | 4/4 | 3/4 | 0/4 | 4/4 |
| CLL B | 0/3 | 0/3 | 0/3 | 3/3 |
| MM T | 0/4 | 0/4 | 0/4 | 4/4 |

HAS1 and HAS2 isoenzymes exhibit cell-type specific expression in malignant B and PC, respectively. As FIG. 3 shows (FIG. 3a; Table 2a), MM B cells express high levels of HAS1 and HAS3 isoenzymes (221 bp and 151 bp fragments respectively). No HAS2 isoenzyme was detected in MM B cells even after precipitation of PCR products, a method that enables analysis of the entire volume of PCR product. In contrast, GeneScan analysis showed that the PC obtained from the BM aspirate of 11 patients with MM expressed HAS2 and HAS3 transcripts (Table 2a; FIG. 3b). In the control group, CD19$^+$B cells obtained from the peripheral blood of 10 healthy donors, we have detected only expression of HAS3 transcripts. Healthy donors expressed no other HASs, HAS1 or HAS2, even after precipitation of PCR products. The B cells obtained from the peripheral blood of patients with MGUS expressed HAS1 and HAS3 transcripts (Table 2b). This expression pattern of HASs in MGUS patients is similar to the expression pattern of the HASs detected in MM B cells, suggesting that HAS1/HAS2 expression patterns may identify pre-malignant conditions and forecast progression to frank myeloma.

In our study, the expression of CD19 transcripts in malignant and normal B cells and the expression of RHAMM transcripts in BM PC were used to evaluate the integrity of isolated mRNA. CD19$^+$B cells and the CD38$^{hi}$CD45$^{lo}$ PC from MM patients expressed high levels of CD19 or RHAMM transcripts. In our experiments, as a control we used B cells isolated from the peripheral blood of healthy donors and as a negative control for each PCR sample we included samples without superscript (−RT), at the RT step. For all samples tested, HAS family transcripts were detectable only in the CD 19$^+$ sorted cells and were undetectable in the non-CD 19$^+$ fractions. Thus, when total PBMC were analyzed, all detected transcripts derived from the B lineage cells in the aggregate population, not from non-B lineage cells. As a primer control to validate quality of the primers we used mRNA obtained from CCL110 fibroblast cell line (derived from human skin) which expressed all three isoenzymes of the HASs. The integrity of mRNA isolated from B cells was evaluated using CD19 primer set, while integrity of mRNA obtained from MM BM PC was evaluated using RHAMM primer set. All primer sets were designed using the "Primer 3" or "Gene Tool" programs based on the published cDNA sequences of the HASs, CD19 and RHAMM.

We also looked at the expression of HASs in T cells sorted from the PB of patients with MM. This analysis identified expression HAS 3 transcripts only in MM T cells (Table 2b). No HAS1 and/or HAS2 expression was detected in MM T cells even after precipitation of 25 μl of PCR reaction. To verify that expression of HAS1 and HAS2 is specific (characteristic) for MM CD19$^+$B and CD38$^{hi}$CD$^{lo}$ PC respectively, throughout the cell-sorting process we collected CD19− fraction of PBMC from 9 MM patients and CD38/CD45 negative fraction of BM cells from 3 MM patients. The expression analysis of HAS genes in those negative fraction demonstrated that MM patients' CD19 and CD38/CD45 negative fractions of the cells (non- B and non-PC cells) do not express HAS1 or HAS2, however expression of HAS3 transcripts were detected in majority of the samples (Table 2a).

Example 3

Novel Splice Variants of HAS1

In addition to cell type specific expression of HAS1 and HAS2 by MM CD19$^+$ B and CD38$^{hi}$CD$^{lo}$ PC respectively, DNA fragment analysis revealed three novel splice variants of HAS1-HAS1Va, HAS1Vb and HAS1Vcin MM CD19$^+$B cells (Table 2a). We analyzed expression of novel variants in CD38$^{hi}$CD45$^{lo}$ PC obtained from 11 patients with MM and CD19$^+$ B cells isolated from the PB of MM patients. This analysis revealed 9% of patients expressing HAS1 novel variants HAS1Va and HAS1Vb in $CD38^{hi}CD45^{lo}$ PC while 62% and 54% of MM patients expressed HAS1Va and HAS1Vb respectively in CD19+ B cells. HAS1Vc transcripts were expressed by 46% MM patients in their CD19+ B cells. Similarly to other genes of HASs no novel splice variants of HAS1; HAS1Va, HAS1Vb and HAS1Vc; were detected in the CD19 negative fraction of PBMC ("non-B-cell" fraction of PBMC) (9 MM patients) and CD38/CD45 negative fraction of BM cells ("non-plasma cell" fraction of BM) obtained from 3 MM patients.

Using RT-PCR we amplified HAS1Va, HAS1Vb and HAS1Vc cDNA fragments from total RNA obtained from MM patients CD19+ B cells. The novel splice variants of HAS1 were identified using a HAS1 specific primer set (SEQ ID NO:9 and SEQ ID NO:10). The amplified cDNA fragments from different patients were cloned into a TOPO PCR 4 TA vector. Next we performed PCR using HAS1 gene specific primer set (SEQ ID NO:9 and SEQ ID NO:10) to identify positive colonies those containing insert of our interest: HAS1Va, HAS1Vb and HAS1Vc. The plasmids isolated from positive clones were sequenced and sequences were identified by alignment with the published sequence of human HAS complete cDNA.

The alignment analysis identified HAS1Va to be a result of complete deletion of exon 4 which leads to an in-frame shift and insertion of premature termination codon (PTC), stop codon TAG, 57 nucleotides downstream of the deletion (FIG. 5 a). HAS1Vb appears to be result of partial retention of intron 4 (59 bp) and deletion of the entirety of exon 4 similar to HAS1Va. The partial retention of intron 4 and deletion of exon 4, leads to an in-frame shift and results in PTC 93 nucleotides downstream of retained intron 4 (FIG. 5b). In both cases, the start codon and entirety of the encoded enzymatically active intracellular loops previously described for HAS1, are present in the aligned cDNA sequences obtained from CD19+ myeloma B cells.

The third novel variant of HAS1-HAS1Vc, which is similar to HAS1Vb, is the result of retention of intron 4. Unlike the other variants of HAS1, HAS1Vc retains exon 4 (FIG. 4). This very rare intronic splicing appears to be a characteristic of a cell with malignant phenotype and may cause a "−1" ribosomal frameshift. The end product of this type of aberration is a truncated protein with disturbed function. Partial retention of the intron, largely a characteristic of malignant cells, can result from activating cryptic 3' mRNA splice sites. HAS1Vc exhibits aberrant intronic splicing. It encodes a classical truncated protein which is predicted to retain ability to produce HA. This aberrant splicing contributes to genetic diversity by generating multiple forms of proteins which often have very different functions and can inhibit function of its full-length counterparts (Black D. L., Cell 103:367 (2000))

Example 4

HAS Expression Profiles in MM Cell Lines:

Using RT-PCR we looked for the presence of novel variants of HAS1Va and HAS1Vb in MM cell lines. From DNA fragment analysis we observed that when cell lines were harvested at the time of exponential proliferation, they expressed novel splice variants of HAS1. When the cell lines were harvested at the stationary phase of growth, no HAS1Va and/or HAS1Vb transcripts were detected. This work suggests that HAS1 variants are expressed only during active phases of malignant cell growth and that expression is turned off when growth abates. We believe that monitoring of HAS gene expression profiles will provide an early marker for detecting emergence of malignant clones in pre-malignant conditions, a sensitive marker for minimal residual disease, and a sensitive marker for impending relapse. Monitoring such profiles is likely to enable rapid therapeutic attack before clinically detectable relapse occurs.

Example 5

An Examination of the Enzymatic Activity of HAS Genes

Figure 7:
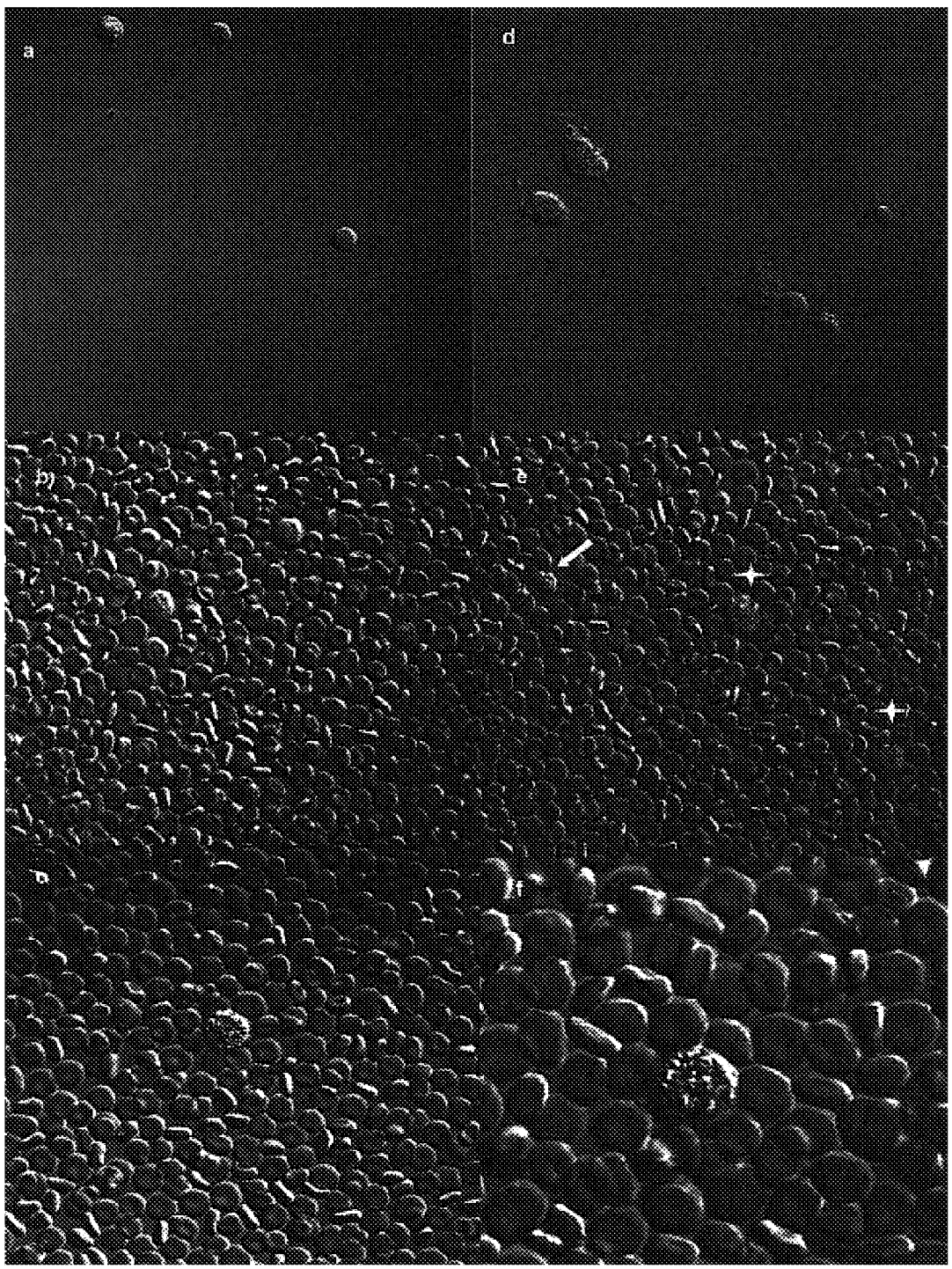
FIG. 7. Visualization of HA pericellular matrix. Micrograph depicting the observed pericellular matrix surrounding B-cells from Multiple Myeloma patients, with no HA matrix observed surrounding B cells until 24 hours after culturing.

Enzymatic activity of the expressed genes of HASs was detected using a particle exclusion assay (PEA). The HA pericellular matrix around the cell plasma membranes was visualized through the addition of a sufficient concentration of fixed erythrocytes to the MM CD19+ B cells and MM $CD38^{hi}CD45^{lo}$ PC in a temporary culture. FIG. 7 shows visualization of a HA pericellular matrix by PEA around MM B cells 4 and 12 h after culturing (FIG. 7). Particle exclusion assay was used to determine the enzymatic activity of HAS proteins encoded by HAS isoenzymes expressed in the B cells of patients with MM, 48 h after culturing (Knudson, W. et al. J Cell Sci: 99:227 (1991)). The images were taken using an Axiovert 100M (Zeiss) confocal laser-scanning microscope. As a negative control, the cells were treated with 100 ml (500 U/ml) of hyaluronidase (HAase-Type-4s from bovine testes; Sigma) for 1 h at 37° C. prior to adding fixed erythrocytes. FIG. 7a,b,c shows the cells 4 h after culturing; FIG. 7d, e, f shows the cells 24 h after culturing. FIG. 7a, d shows the cells before addition of fixed erythrocytes; and FIG. 7c, f shows the cells treated with HAase. Cells with a HA coat are shown by arrows and cells without a HA pericellular matrix by a star.

The fixed erythrocytes were excluded from the cell plasma membranes as result of their large size and the negative charge of the HA. The HA pericellular matrix was detected around MM B cells only, while MM BM PC and B cells obtained from healthy donors did not exhibit any pericellular matrix around their plasma membranes. Furthermore, no HA matrix was detected around the MM B cells plasma membrane 4 h (FIG. 7a,b,c) and 12 h (FIG. 7d,e,f) after their culturing; however 24 h later, a small amount of an HA matrix was detected around some MM B cells plasma membranes, while other B cells in the culture did not exhibit an HA matrix.

Figure 8:
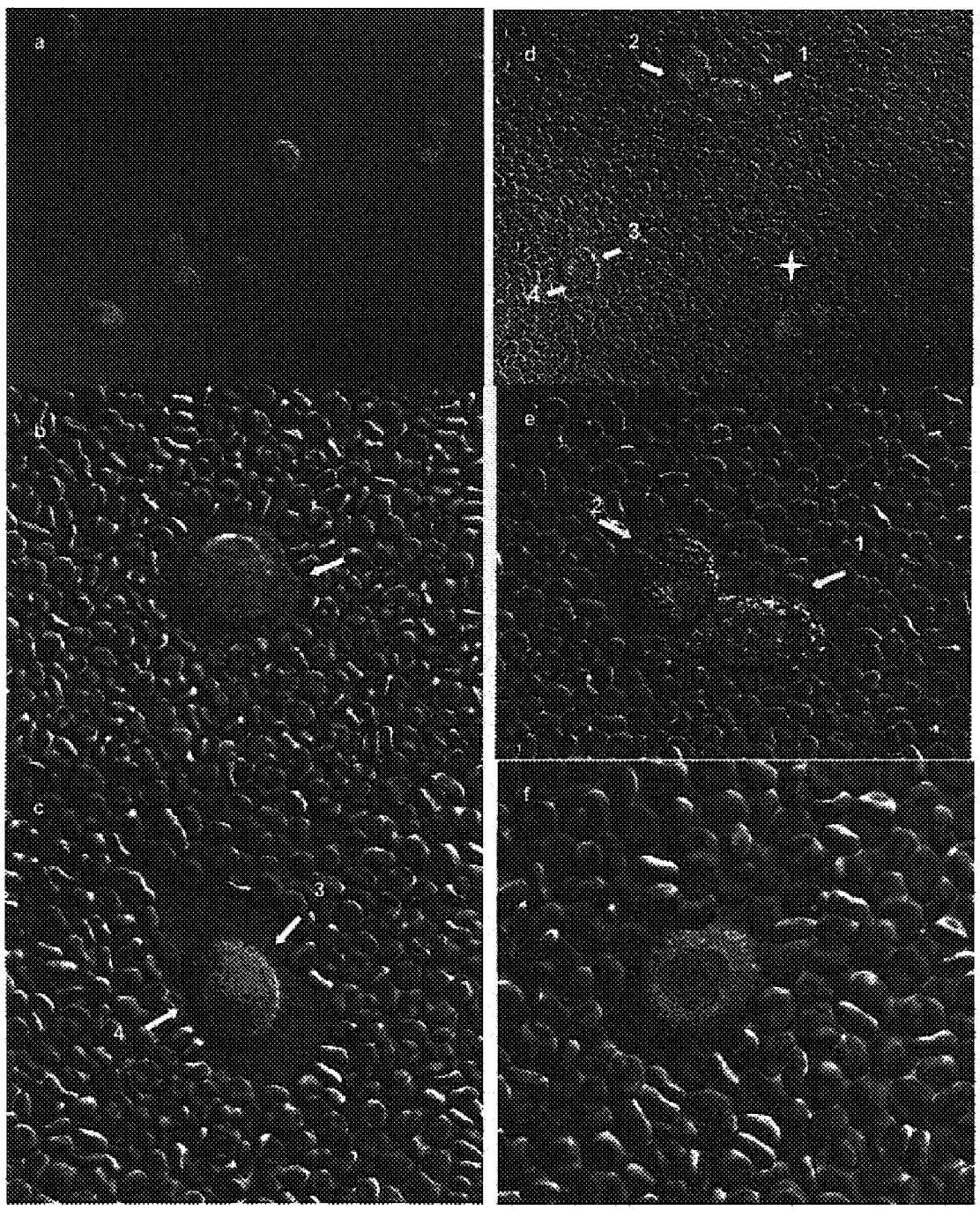
FIG. 8. Visualization of HA pericellular matrix. Micrograph depicting the observed pericellular matrix surrounding B-cells from Multiple Myeloma patients 48 hours post-culture, with the size of the HA pericellular matrix significantly increasing.

FIG. 8 shows the visualization of HA pericellular matrix by PEA around MM B, cells 48 h after culturing (FIG. 8). Particle exclusion assay was used to determine the enzymatic activity of HAS proteins encoded by HAS isoenzymes expressed in the B cells of patients with MM, 48 h after culturing (Knudson, W. et al. J Cell Sci: 99:227 (1991)). The images were taken using an Axiovert 100M (Zeiss) confocal laser-scanning microscope. As a negative control, the cells were treated with 100 µl (500 U/ml) of hyaluronidase (HAase - Type-4s from bovine testes; Sigma) for 1 h at 37° C. prior to adding fixed erythrocytes. FIG. 8a shows the cells before addition of fixed erythrocytes; FIG. 8b,c,d,e shows cells after addition of fixed erythrocytes; FIG. 8f shows the cells treated with HAase; FIG. 8c,d,e show high magnification images of cells with a HA pericellular matrix. The cells with a HA pericellular matrix shown by arrows and the cells without a HA pericellular matrix by the star; green color represents CD19-FITC staining.

Figure 9:
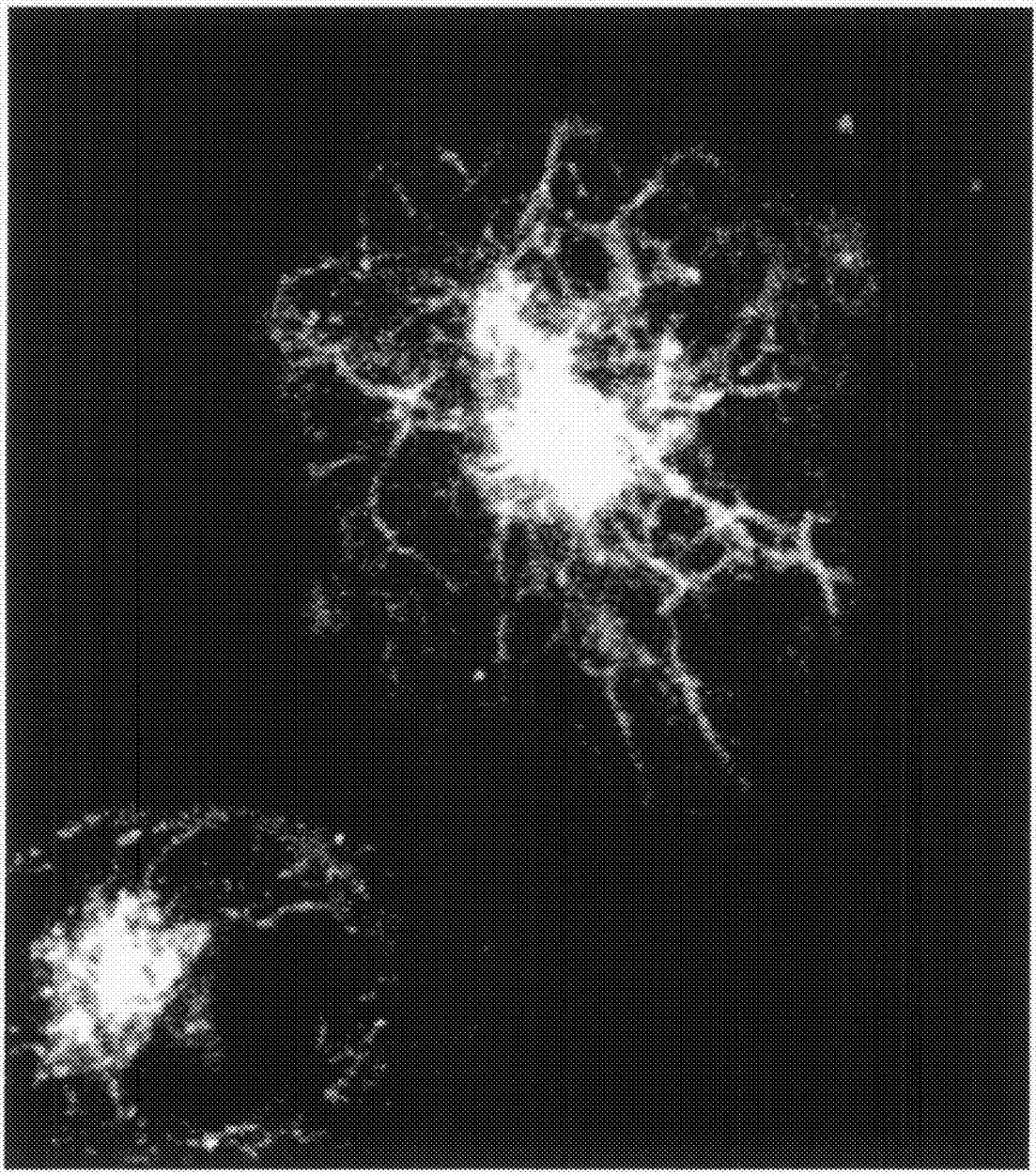
FIG. 9. Visualization of presence of HA in cells. Micrograph showing the presence of intracellular HA by indirect staining of MM cells with HABP.

The size of an HA pericellular matrix significantly increased around some MM B cells 48 h after culturing (FIG. 8a,b,c,d,e,f), while other B cells did not develop an HA pericellular matrix (FIG. 8d—cells with star). Interestingly, in the culture some cells were characterized by the existence of a prominent coat of an HA at one edge of the cell while the opposite edge of the same cell exhibited less of an HA matrix (FIG. 8e). This type of distribution of an HA pericellular matrix around the cells may be due to cell motility. Motile cells would exhibit a prominent HA halo at their trailing edge and a lesser pronounced halo at their leading edge. After Hyaluronidase treatment, no HA matrix was detected around CD19+MM B cell plasma membranes (FIG. 8f). HA was also detectable inside cells expressing HAS1 as demonstrated by indirect staining of cells with HABP (FIG. 9).

Example 6

PEA in Combination with HA Staining

The existence of HA molecules in the pericellular matrix detected by Particle Exclusion Assay was verified by incubating cells with biotinylated Hyaluronan Binding Protein (HBP) prior to the Particle Exclusion Assay (FIG. 4b). This binding was visualized using streptavidin Alexa Fluor 633. As FIG. 4b. shows, the cell and pericellular matrix which excluded fixed erythrocytes was stained with streptavidin Alexa Fluor 633. Interestingly, the cells stained with streptavidin Alexa Fluor 633 only, which was used as a negative control in our experiments to detect specificity of streptavidin, showed a punctuate dim staining which is due to streptavidin binding to integrins and related cell surface molecules (FIG. 4b).

Example 7

Overexpression of HASs and HAS1 Splice Variants in Waldenstrom's Macroglobulinemia Waldenstrom's Macroglobulinemia (WM), which has clinical and pathological similarities with multiple myeloma (MM), is an indolent B cell malignancy. This lymphoplasmoproliferative disorder is characterized by bone marrow (BM) infiltration by lymphocytes and plasmacytoid cells and IgM paraproteinemia. Little is known about the biology or spread of WM. Using DNA fragment analysis we analyzed the expression pattern of HAS genes in BM aspirates and the peripheral blood of patients with WM. HAS3 is expressed in all tested patients and normal donors. However, the expression of HAS1 and HAS2 varies among WM patients. This observation suggests the existence of a heterogeneous population of malignant cells in tested WM patients as well as a degree of patient specificity. In addition, we have detected HAS1Va, HAS1Vb and HAS1Vc in WM patients but not in the normal counterparts of these malignant cells. Analysis of individual sorted B cells from blood and BM of WM patients shows that the majority of cells express exclusively HAS1 variants and frequently lack full length HAS1 (Table 3a,b). This may reflect mutations in genomic DNA or may result from regulation of gene transcription. HAS1 variants are not detected in healthy donors.

TABLE 3a

Expression of HASs in WM patients

| | HAS1Va | HAS1Vb | HAS1 | HAS2 | HAS3 |
|---|---|---|---|---|---|
| BM cells Patient n = 11 | 54 | 9 | 82 | 64 | 100 |
| PBMC Patient n = 7 | 57 | 42 | 57 | 85 | 100 |

TABLE 3b

Expression of HASs in WM CD20+ single cells

| | % Of Individual Cells Expressing: | | | |
|---|---|---|---|---|
| | HAS1Va | HAS1Vb | HAS1 | HAS2 |
| Patient # 1 CD20+ PB | 66% | 10% | 3% | 4% |
| Patient # 2 CD20+ PB | 68% | 11% | 5% | 3% |
| Patient # 2 BM CD20+ | 97% | 76% | 3% | 0% |
| Healthy donors (n = 10) | 0% | 0% | 0% | 0% |

We speculate that HAS1 variants synthesize the intracellular HA ligand for RHAMM. RHAMM contributes to genetic instability in myeloma, and we believe that it may also contribute to genetic instability in WM.

Based on our results, we also suggest that overexpression of full length HAS1 and HAS2 may form an extracellular HA matrix around WM cells, thus preventing their elimination by the immune system. Furthermore, the existence of an HA matrix around the malignant cells is likely to promote their migration, and consequently may facilitate the spread of disease. Thus, HASs may contribute to genetic instability and malignant spread in WM.

Example 8

Aberrant Splicing of Hyaluronan Synthase 1 (HAS1) Gene in Multiple Myeloma (MM): Impact on Patient Survival.

Based on sequence and alignment analysis we find that this point mutation, which is located on the highly conserved exon of HAS1, promotes activation of cryptic splice sites and consequently mediates aberrant splicing of HAS1 gene. Occurrence of the point mutation in HAS1Va transcripts (FIG. 5a) suggests the presence of a new variant allele of HAS1 in MM patients which may be a novel disease marker. This point mutation does not hinder HA synthesis, and is likely to mediate accumulations of intracellular HA.

HA is a ligand for both surface and intracellular RHAMM. Inside the cell, RHAMM is a centrosomal protein likely mediating genetic instability in MM. Thus, HAS1 and its novel variants not only promote RHAMM-dependent MM B cell migration, as previously demonstrated by us, but through synergy with RHAMM, may promote the emergence of increasingly aggressive genetic variants in MM.

FIGS. 10, 11, 12 and 13 show the statistical analysis of 41 MM PBMC demonstrating expression of HAS1 and its novel splice variants correlate strongly with poor survival in these patients (HAS1:P=0.03, HAS1Va:P=0.03 and HAS1Vb: P=0.002) (FIG. 10-13). Data for the statistical analysis were analyzed using SAS version 8.2 for windows (SAS Inc., Cary, N.C.) and GraphPad Prism version 3.02 for Windows (GraphPad software, San Diego Calif.). Categorical variables were compared between two groups using Fisher's exact test. Continuous variables were compared using Student's t-test or the Wilcoxon rank sum test as appropriate. Survival distributions were determined using the Kaplan Meier method and compared using the log rank test. Multivariable analysis and hazard ratios were generated using Cox regression models. Statistical significance was set at a p-value of 0.05 using two-sided analysis. p=0.03.

Figure 10:
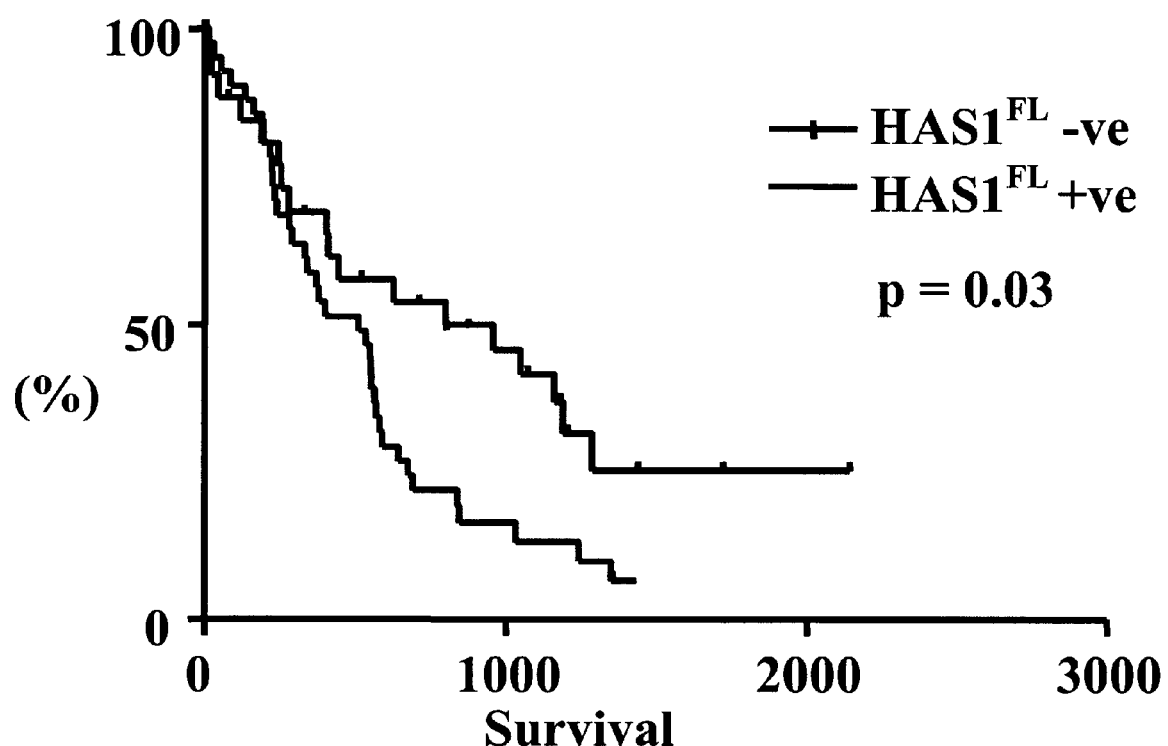
FIG. 10. Kaplan-Meier survival plots of $HAS1^{FL}$. Patients with Multiple Myeloma showed reduced survival if expressing $HAS1^{FL}$ isoenzyme in peripheral blood mononuclear cells.
Figure 11:
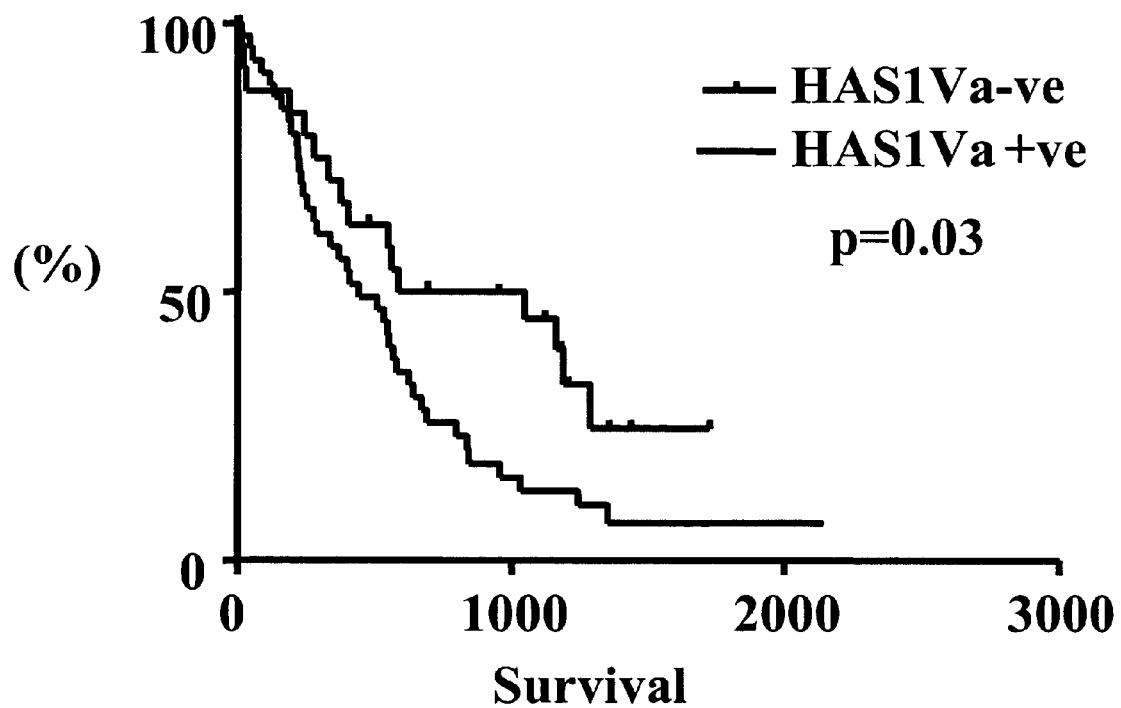
FIG. 11. Kaplan-Meier survival plots of HAS1Va. Patients with Multiple Myeloma showed reduced survival if expressing HAS1Va isoenzyme in peripheral blood mononuclear cells.
Figure 12:
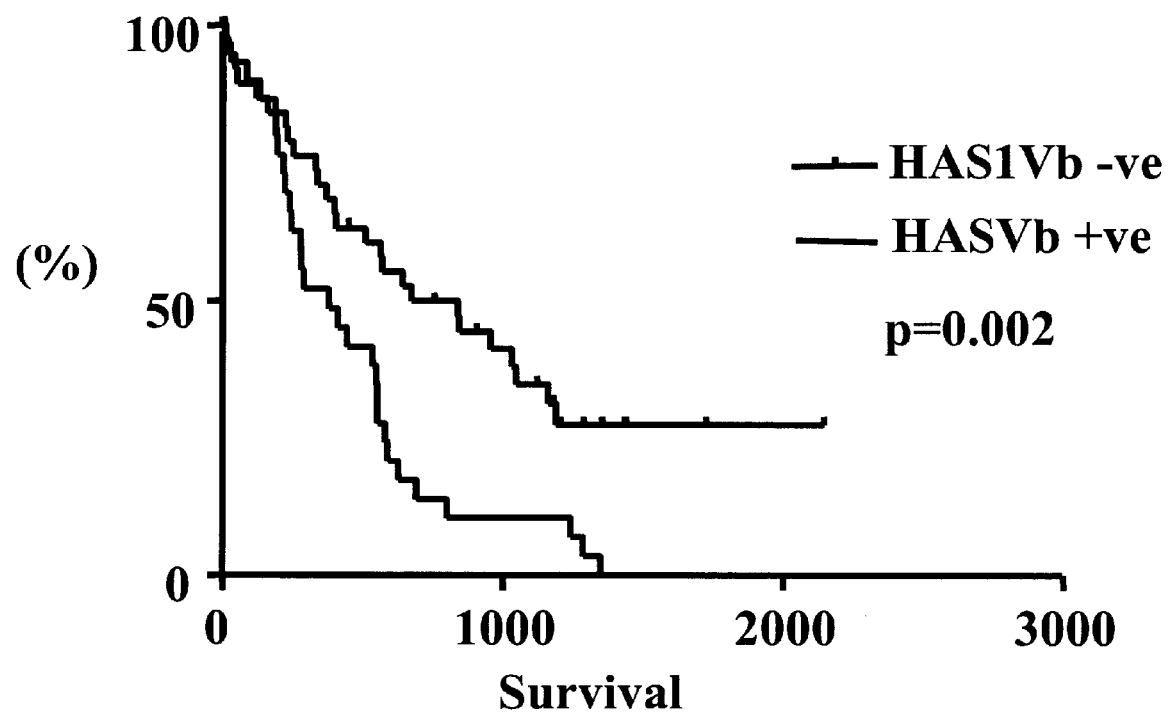
FIG. 12. Kaplan-Meier survival plots of HAS1Vb. Patients with Multiple Myeloma showed reduced survival if expressing HAS1Vb isoenzyme in peripheral blood mononuclear cells.

Longitudinal analysis during the course of disease of HAS1 and its novel variants in 26 MM patients indicates that the majority of the patients express HAS1 and its novel variants at diagnosis and as they relapse. HAS1Va and HAS1Vb are the first survival marker to be described that reflect the properties of circulating, malignant, MM B cells. This provides evidence in support of a key role for early stage MM cells, and highlights potential mechanisms through which MM B cells may impact disease progression. This correlation with reduced patient survival supports the idea that HAS1 and the highly abnormal HAS1 splice variants are central components of disease progression in multiple myeloma (FIG. 10, 11, 12).

Figure 13:
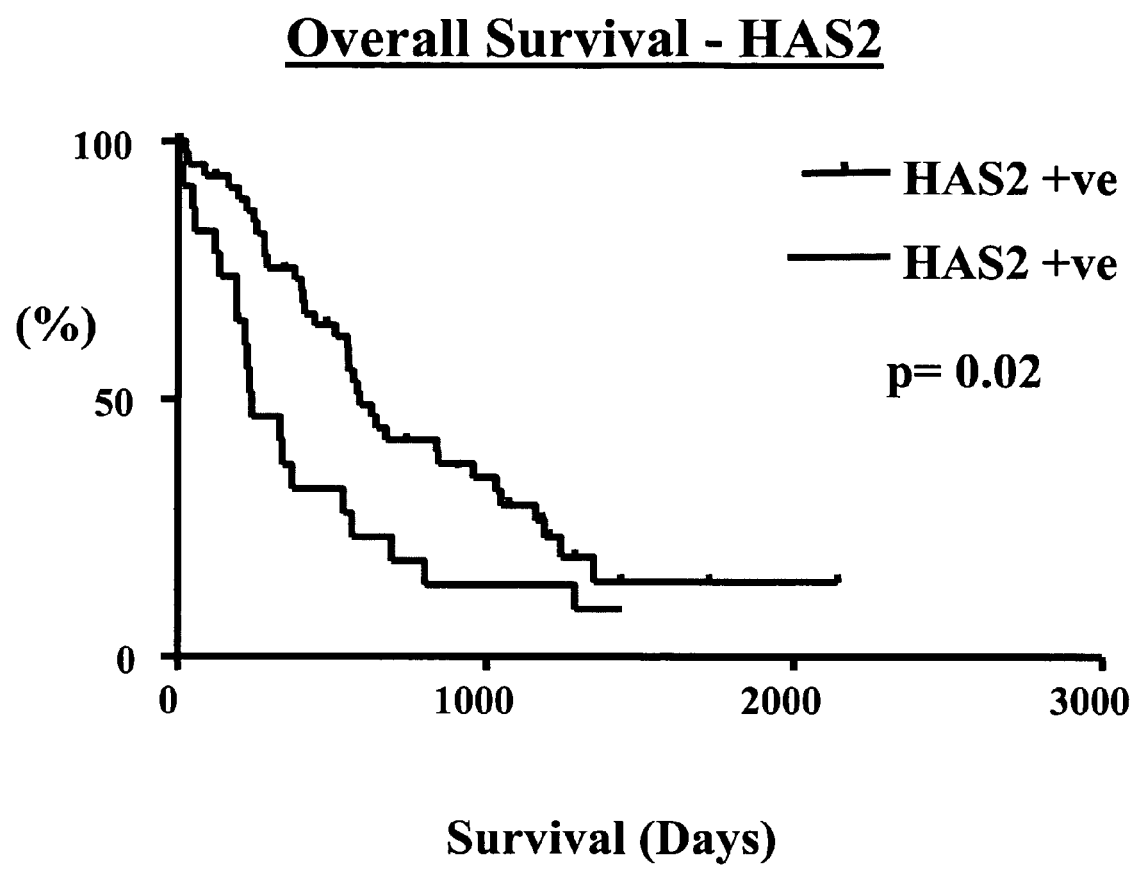
FIG. 13. Kaplan-Meier survival plots of HAS2. Patients with Multiple Myeloma showed reduced survival if expressing HAS2 isoenzyme in blood cells.

In addition, expression of HAS2 by circulating blood cells also correlates with poor survival (p=0.02) (FIG. 13). Since we have been unable to detect HAS2 in purified myeloma B-cells, this expression may reflect circulating plasma cells and may therefore be a surrogate marker for circulating plasma cells as well as a marker for poor clinical outcome.

The clinically significant detection of HAS1, HAS1 isoenzyme variants and HAS2 in peripheral blood cells, provides a relatively painless and non-invasive method to monitor malignancy before, during, and after therapy; in minimal disease and to detect impending relapse. Current methods that rely on BM biopsies require a medically trained practitioner, are painful, difficult to apply, and expensive. This invention provides for a less invasive blood test, which may replace conventional BM-based testing for disease parameters in cancer and for other diseases characterized by overexpression of HAS genes, unfavourable single nucleotide polymorphisms in HAS genes or aberrant HAS1 gene splicing.

Example 9

Figure 14:
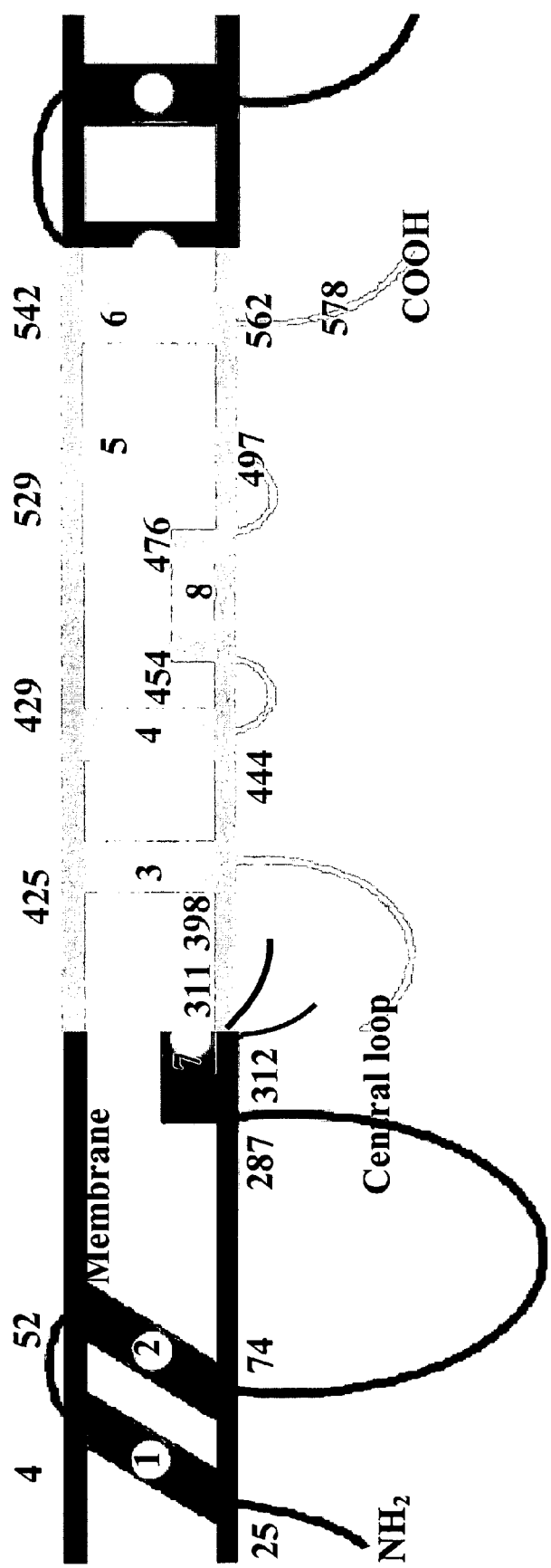
FIG. 14. Topological structure of HAS1 novel variants. Predicted topographical structure of the protein shows retention of the enzymatically active central loop in the truncated HAS1Va, HAS1Vb, and HAS1Vc proteins.
Figure 15:
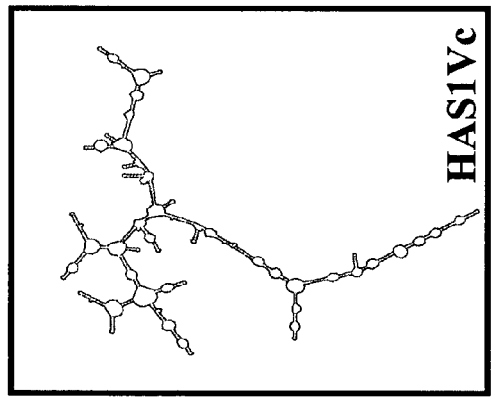
FIG. 15. Secondary mRNA structure of HAS1Va, HAS1Vb and HAS1Vc. Predicted secondary mRNA structure shows the existence of pseudoknots which lead to aberrant "−1" ribosomal frameshifting.
Figure 15:
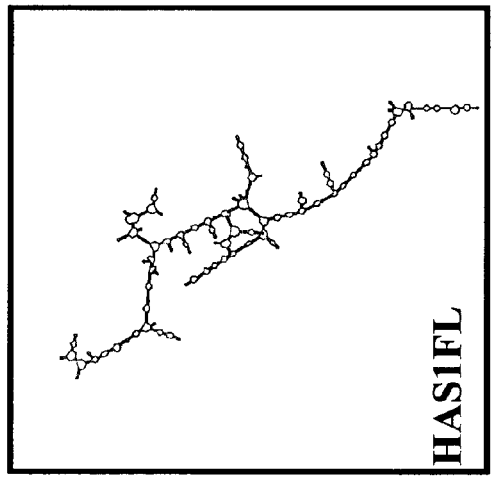
Figure 15:
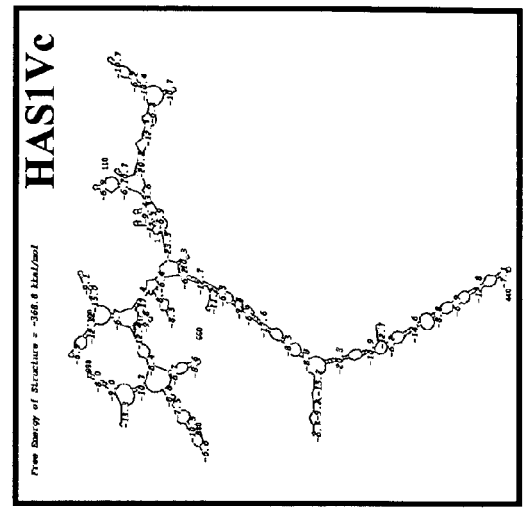
Figure 15:
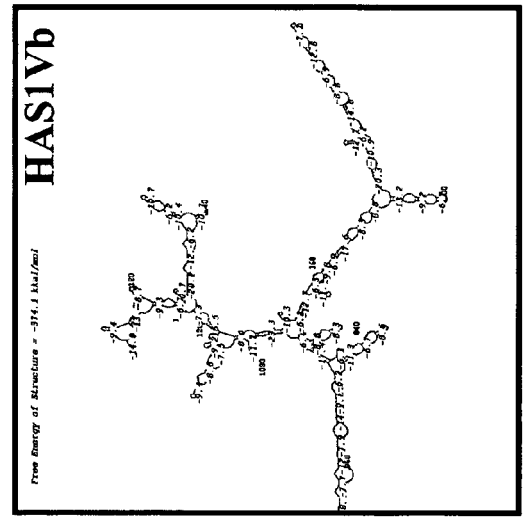
Figure 15:
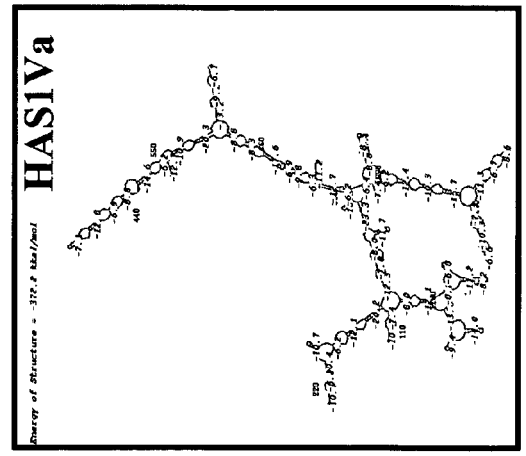

Comparative Analysis of HAS1 Isoenzyme Variant Nucleotide and Amino Acid Sequence Based on alignment analysis it is clear that novel variants HAS1Va, HAS1Vb and HAS1Vc are the results of aberrant splicing (sequence alignment of nucleotides and amino acids). FIG. 14 shows the topological structure of HAS1 novel variants as determined based on: the topological structure of spHAS (Heldermon et al.), with results obtained though secondary structure prediction software (Swiss-Prot) and alignment analysis (FIG. 14). The end product of this type of splicing is a truncated protein. However, these truncated proteins of HAS1Va, HAS1Vb and HAS1Vc retained the central loop of the protein, which is the enzymatically active part of the full length HAS1. The process of aberrant splicing which was identified in the transcripts of HAS1 gene leads to mRNA aberrations and may also have a significant impact on the translational machinery. FIG. 15 shows the predicted secondary mRNA structure for HAS1Va, HAS1Vb and HAS1Vc, obtained using Mfold software and PKNOTS software, with implementation of dynamic programming that includes pseudoknots (FIG. 15). This prediction is based on the calculation of the free energy of different base pairing patterns. Thermodynamic parameters derived from oligonucleotides have permitted the approximation of free energy contributions of double-helical regions and various loops. The secondary structure analysis of HAS1, HAS1Va, HAS1Vb and HAS1Vc mRNA sequences showed the existence of pseudoknots on these transcripts (FIG. 15), previously thought to lead to aberrant "−1" ribosomal frame shifting during translational events.

Example 10

Detection of HAS Isoenzyme Variants using Microfluidics Platform

Figure 16:
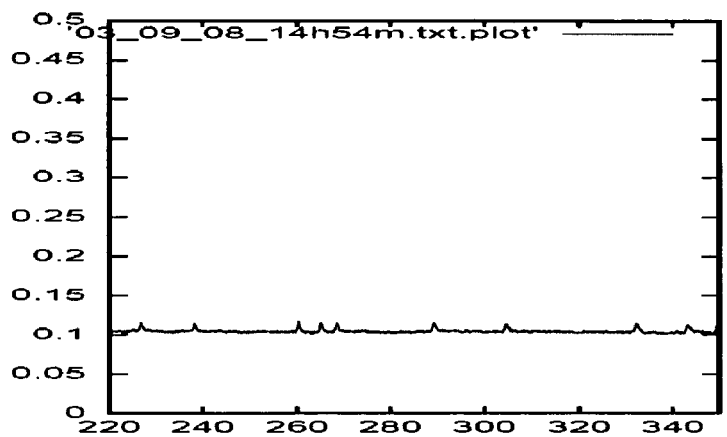
FIG. 16. RT-PCR product analysis on microfluidic chip. Use of a microfluidic device in RT-PCR of cDNA generated from $CD19^+$B-cells using SEQ ID NO:9 and SEQ ID NO:10 as primers; with internal size standards as a function of the X-axes and fluorescence (relative quantity) depicted on the Y-axes.
Figure 16:
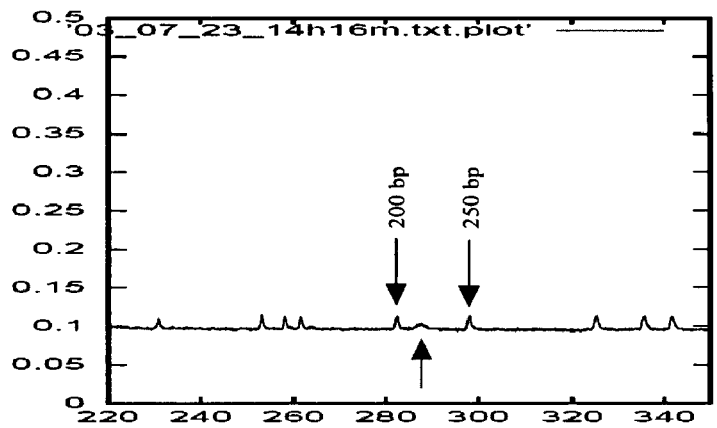
Figure 16:
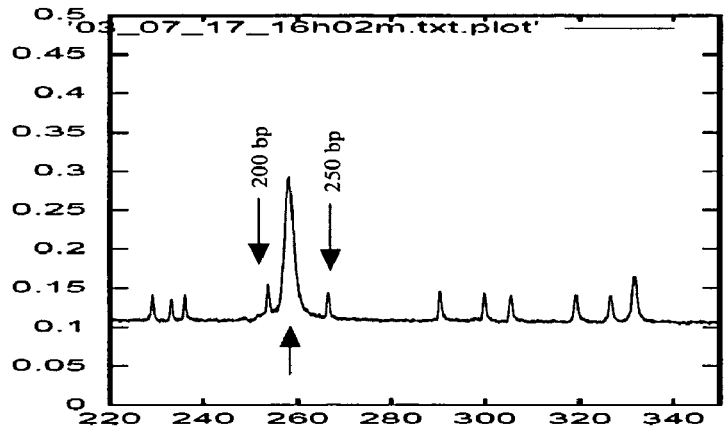

FIG. 16 shows use of a microfluidic device for detection of HAS1 isoenzyme or isoenzyme variants from within a cell population (FIG. 16). cDNA for the PCR reactions was reverse-transcribed from total mRNA isolated from sorted CD19+ B. RNA was reverse-transcribed and cDNA obtained from RT reaction was amplified by primer represented by SEQ ID NO:9 and SEQ ID NO:10. From these primer sets, the 5' primers were labeled at their 5' ends with 6-carboxyflourescein (VIC) (Applied Biosystems). PCR products obtained from different cycles of the reactions were mixed with a loading buffer, 12 ml of formamide and 1 ml of internal size standard GeneScan 500 [LIZ] (Applied Biosystems). Next, PCR products were denatured for 4 minutes at 96° C. and after quick spin, samples were transferred immediately to ice for 15 minutes. Samples were separated on microfluidic chip. Product peaks are indicated with red arrows while size standard peaks are indicated with black arrows.

Figure 17:
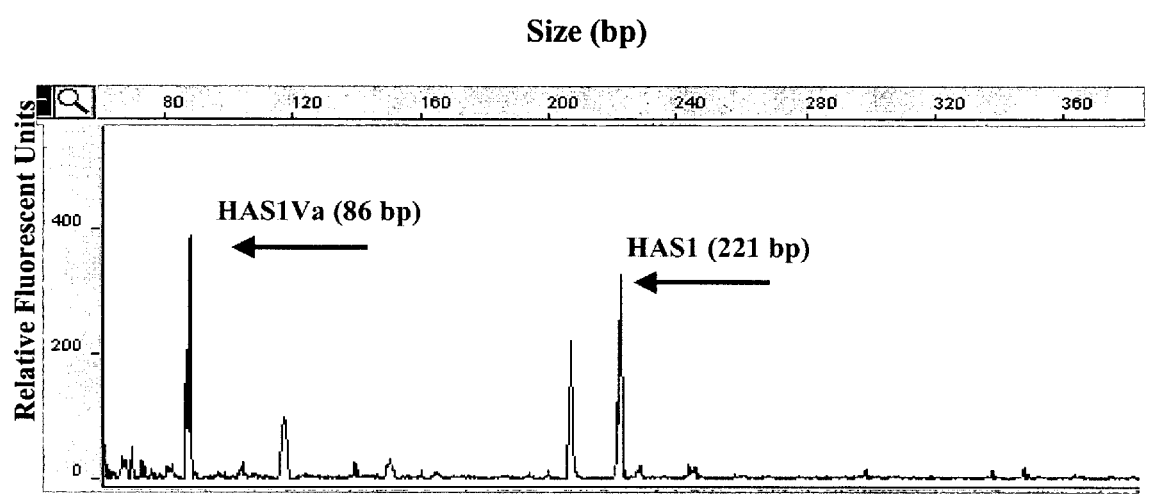
FIG. 17. RT-PCR product analysis on microfluidic chip. Demonstration of the ability to analyze product using the ABI 3100 DNA fragment analyzer, with fragment size a function of the X-axes and fluorescence (relative quantity) depicted on the Y-axes.

We tested the practical aspects and limitations of a microfluidics approach by amplifying HAS1 and its novel isoenzymes variants in MM patients and in cell lines. On-chip analysis enabled detection of HAS1 and its novel variants PCR products after 15 cycles of PCR (FIG. 16). The same product is undetectable with capillary electrophoresis performed on an ABI3100 genetic analyzer even when concentrating 25 µl of PCR reaction. We successfully performed on-chip PCR using an automated intelligent valving system and amplified HAS1 and its novel splice variants in 2 µl of total PCR reaction. FIG. 17 shows on-chip PCR analysis with the ABI 3100 DNA fragment analyzer (FIG. 17.). Total RNA was obtained from MM patients, CD19+ B cells. 2 ul of PCR mix was thermo-cycled on PDMMS-glass PCR chip, next 0.9 ul of PCR product was retrieved mixed with formimide and analyzed on ABI 3100 Genetic Analyzer (FIG. 17).

Example 11

Predicted Splice Site and Mutational Hotspots in the HAS1 Gene:

Splice sites on intron 4 were predicted using Neural Network Splice Site Prediction Tool and SEAN (UK) single nucleotide polymorphism prediction software. The score cutoff was set up between 0 and 1. Predicted splice sites were chosen based on the percent splice sites recognized and the percent false positives for different cutoff scores for 5' versus 3' splice site prediction. (Reese, .G. *J Comp Biol* 4:311 (1997)). Using this program we predicted and then detected HAS1Vc. We have also used these programs to validate the existence of splice sites that characterize HAS1Va and HAS1 Vb. FIG. 18 shows splice sites on intron 4 predicted using the WWW interface for the Neural Network Splice Site Prediction Tool, with a score cutoff between 0 and 1 (FIG. 18). Predicted splice sites were chosen based on the percent splice sites recognized and the percent false positives for different cutoff scores for 5' versus 3' splice site prediction (Reese, .G., *J Comp Biol* 4:311 (1997)). Each splice site corresponds to potential novel aberrant variants of HAS1 gene that could encode truncated proteins of HAS1. Thus by extrapolation, we believe that new splice variants will be detected that utilize the splice sites predicted (FIG. 18).

Identification of seven splice donor and five splice acceptor sites on intron 4 (FIG. 18) suggests existence of potential novel aberrant variants of HAS1 gene that could encode truncated proteins of HAS1. Based on this analysis we could conclude that exon 4 and intron 4 are hot spots for mutations, which can be specific to disease type. A similar phenomenon is reported in case of MDM2 gene. Upregulation of splice variants of MDM2 is characteristic of breast cancer patients while amplifications of full length of MDM2 genes but not splice variants has been detected in patients with soft tissue sarcoma. (Bartel, F. et al. *International J Cancer* 95:168 (2001); Dang, J. et al. *Cancer Res* 62:1222 (2002); Evdokiou A. et al. *International J Oncol* 19:625 (2001); Hori M. et al. *Pathol Int* 50:786 (2000); Maestro, R. et al. *Blood* 85:3239 (1995); Tamborini, E. et al. *International J Cancer* 92:790 (2001)).

Although the disclosure describes and illustrates preferred embodiments of the invention, it is to be understood that the invention is not limited to these particular embodiments. Many variations and modifications will now occur to those skilled in the art. For a definition of the invention reference is to be had to the Summary of the Invention and the attached Claims.

What is claimed is:

1. A method to detect expression of a HAS1 isoenzyme variant, wherein the HAS1 isoenzyme variant is SEQ ID NO.4 comprising:
   i) mixing a cell or sample of cell populate from a human with reverse transcriptase in conditions enabling conversion of mRNA to DNA templates thereby generating cDNA templates;
   ii) mixing said cDNA templates with oligonucleotide primers SEQ ID NO:9 and SEQ ID NO: 10;
      a. Reacting said mixture ii with enzymes and compounds to enable specific fragments of DNA to be increased in number;
      b. Detecting the presence of an increased number of resulting DNA fragments of 86 base pairs from SEQ ID NO:3.

2. The method of claim 1 wherein the process is performed using a microfluidic device.

3. A method to detect expression of HAS1Va isoenzyme variant in a cell or cell population comprising detection of single nucleotide conversion of base 924 of SEQ ID NO:3 from a cytosine to a thymidine residue.

4. A method to determine the likelihood of survival rate over time in a human suffering from multiple myeloma comprising characterizing HAS1Va isoenzyme variant expression in a cell or cell population using the method of claim 1, wherein the HAS1Va isoenzyme variant is SEQ ID NO. 4.

5. The method of claim 4 wherein the cell or cell population is selected from the group comprising blood, B-cells, CD 19.sup.+B cells, CD 19.sup.+peripheral blood mononuclear cells and bone marrow plasma cells.

* * * * *

SEQUENCE LISTING

<160> NUMBER OF SEQ ID NOS: 14

<210> SEQ ID NO 1
<211> LENGTH: 1737
<212> TYPE: DNA
<213> ORGANISM: Homo sapiens

<400> SEQUENCE: 1

```
atgagacagc aggacgcgcc caagcccact cctgcagccc gccgctgctc cggcctggcc      60
cggagggtgc tgaccatcgc cttcgccctg ctcatcctgg gcctcatgac ctgggcctac     120
gccgccgggg tgccgctggc ctccgatcgc tacggcctcc tggccttcgg cctctacggg     180
gccttccttt cagcgcacct ggtggcgcag agcctcttcg cgtacctgga gcaccggcgg     240
gtggcggcgg cggcgcgggg gccgctggat gcagccaccg cgcgcagtgt ggcgctgacc     300
atctccgcct accaggagga ccccgcgtac ctgcgccagt gcctggcgtc cgcccgcgcc     360
ctgctgtacc cgcgcgcgcg gctgcgcgtc ctcatggtgg tggatggcaa ccgcgccgag     420
gacctctaca tggtcgacat gttccgcgag gtcttcgctg acgaggaccc cgccacgtac     480
gtgtgggacg gcaactacca ccagcccctgg gaacccgcgg cggcgggcgc ggtgggcgcc     540
ggagcctatc gggaggtgga ggcggaggat cctgggcggc tggcagtgga ggcgctggtg     600
aggactcgca ggtgcgtgtg cgtggcgcag cgctggggcg gcaagcgcga ggtcatgtac     660
acagccttca aggcgctcgg agattcggtg gactacgtgc aggtctgtga ctcggacaca     720
aggttggacc ccatggcact gctggagctc gtgcgggtac tggacgagga ccccccggta     780
ggggctgttg gtggggacgt gcggatcctt aaccctctgg actcctgggt cagcttccta     840
agcagcctgc gatactgggt agccttcaat gtggagcggg cttgtcagag ctacttccac     900
tgtgtatcct gcatcagcgg tcctctaggc ctatatagga ataacctctt gcagcagttt     960
cttgaggcct ggtacaacca gaagttcctg ggtacccact gtactttgg ggatgaccgg    1020
cacctcacca accgcatgct cagcatgggt tatgctacca agtacacctc caggtcccgc    1080
tgctactcag agacgccctc gtccttcctg cggtggctga gccagcagac acgctggtcc    1140
aagtcgtact tccgtgagtg gctgtacaac gcgctctggt ggcaccggca ccatgcgtgg    1200
atgacctacg aggcggtggt ctccggcctg ttcccctct tcgtggcggc cactgtgctg    1260
cgtctgttct acgcgggccg cccttgggcg ctgctgtggg tgctgctgtg cgtgcagggc    1320
gtggcactgg ccaaggcggc cttcgcggcc tggctgcggg gctgcctgcg catggtgctt    1380
ctgtcgctct acgcgcccct ctacatgtgt ggcctcctgc ctgccaagtt cctggcgcta    1440
gtcaccatga accagagtgg ctgggcacc tcgggccggc ggaagctggc cgctaactac    1500
gtccctctgc tgccctggc gctctgggcg ctgctgctgc ttgggggcct ggtccgcagc    1560
```

```
gtagcacacg aggccagggc cgactggagc ggcccttccc gcgcagccga ggcctaccac    1620
ttggccgcgg gggccggcgc ctacgtgggc tactgggtgg ccatgttgac gctgtactgg    1680
gtgggcgtgc ggaggctttg ccggcggcgg accgggggct accgcgtcca ggtgtga       1737
```

<210> SEQ ID NO 2
<211> LENGTH: 578
<212> TYPE: PRT
<213> ORGANISM: Homo sapiens

<400> SEQUENCE: 2

```
Met Arg Gln Gln Asp Ala Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
        35                  40                  45

Asp Arg Tyr Gly Leu Leu Ala Phe Gly Leu Tyr Gly Ala Phe Leu Ser
    50                  55                  60

Ala His Leu Val Ala Gln Ser Leu Phe Ala Tyr Leu Glu His Arg Arg
65                  70                  75                  80

Val Ala Ala Ala Arg Gly Pro Leu Asp Ala Thr Ala Arg Ser
                85                  90                  95

Val Ala Leu Thr Ile Ser Ala Tyr Gln Glu Asp Pro Ala Tyr Leu Arg
                100                 105                 110

Gln Cys Leu Ala Ser Ala Arg Ala Leu Leu Tyr Pro Arg Ala Arg Leu
            115                 120                 125

Arg Val Leu Met Val Val Asp Gly Asn Arg Ala Glu Asp Leu Tyr Met
        130                 135                 140

Val Asp Met Phe Arg Glu Val Phe Ala Asp Glu Asp Pro Ala Thr Tyr
145                 150                 155                 160

Val Trp Asp Gly Asn Tyr His Gln Pro Trp Glu Pro Ala Ala Gly
                165                 170                 175

Ala Val Gly Ala Gly Ala Tyr Arg Glu Val Glu Ala Glu Asp Pro Gly
                180                 185                 190

Arg Leu Ala Val Glu Ala Leu Val Arg Thr Arg Arg Cys Val Cys Val
            195                 200                 205

Ala Gln Arg Trp Gly Gly Lys Arg Glu Val Met Tyr Thr Ala Phe Lys
        210                 215                 220

Ala Leu Gly Asp Ser Val Asp Tyr Val Gln Val Cys Asp Ser Asp Thr
225                 230                 235                 240

Arg Leu Asp Pro Met Ala Leu Leu Glu Leu Val Arg Val Leu Asp Glu
                245                 250                 255

Asp Pro Arg Val Gly Ala Val Gly Gly Asp Val Arg Ile Leu Asn Pro
                260                 265                 270

Leu Asp Ser Trp Val Ser Phe Leu Ser Ser Leu Arg Tyr Trp Val Ala
            275                 280                 285

Phe Asn Val Glu Arg Ala Cys Gln Ser Tyr Phe His Cys Val Ser Cys
        290                 295                 300

Ile Ser Gly Pro Leu Gly Leu Tyr Arg Asn Asn Leu Leu Gln Gln Phe
305                 310                 315                 320

Leu Glu Ala Trp Tyr Asn Gln Lys Phe Leu Gly Thr His Cys Thr Phe
                325                 330                 335

Gly Asp Asp Arg His Leu Thr Asn Arg Met Leu Ser Met Gly Tyr Ala
```

```
                    340             345              350
Thr Lys Tyr Thr Ser Arg Ser Arg Cys Tyr Ser Glu Thr Pro Ser Ser
                355             360             365
Phe Leu Arg Trp Leu Ser Gln Gln Thr Arg Trp Ser Lys Ser Tyr Phe
            370             375             380
Arg Glu Trp Leu Tyr Asn Ala Leu Trp Trp His Arg His Ala Trp
385             390             395             400
Met Thr Tyr Glu Ala Val Val Ser Gly Leu Phe Pro Phe Phe Val Ala
                405             410             415
Ala Thr Val Leu Arg Leu Phe Tyr Ala Gly Arg Pro Trp Ala Leu Leu
            420             425             430
Trp Val Leu Leu Cys Val Gln Gly Val Ala Leu Ala Lys Ala Ala Phe
            435             440             445
Ala Ala Trp Leu Arg Gly Cys Leu Arg Met Val Leu Leu Ser Leu Tyr
        450             455             460
Ala Pro Leu Tyr Met Cys Gly Leu Leu Pro Ala Lys Phe Leu Ala Leu
465             470             475             480
Val Thr Met Asn Gln Ser Gly Trp Gly Thr Ser Gly Arg Arg Lys Leu
                485             490             495
Ala Ala Asn Tyr Val Pro Leu Leu Pro Leu Ala Leu Trp Ala Leu Leu
            500             505             510
Leu Leu Gly Gly Leu Val Arg Ser Val Ala His Glu Ala Arg Ala Asp
        515             520             525
Trp Ser Gly Pro Ser Arg Ala Ala Glu Ala Tyr His Leu Ala Ala Gly
    530             535             540
Ala Gly Ala Tyr Val Gly Tyr Trp Val Ala Met Leu Thr Leu Tyr Trp
545             550             555             560
Val Gly Val Arg Arg Leu Cys Arg Arg Arg Thr Gly Gly Tyr Arg Val
                565             570             575
Gln Val

<210> SEQ ID NO 3
<211> LENGTH: 1071
<212> TYPE: DNA
<213> ORGANISM: Homo sapiens

<400> SEQUENCE: 3
atgagacagc aggacgcgcc caagcccact cctgcagccc gccgctgctc cggcctggcc      60
cggagggtgc tgaccatcgc cttcgccctg ctcatcctgg gcctcatgac ctgggcctac     120
gccgccgggg tgccgctggc ctccgatcgc tacggcctcc tggccttcgg cctctacggg     180
gccttccttt cagcgcacct ggtggcgcag agcctcttcg cgtacctgga gcaccggcgg     240
gtggcggcgg cggcgcgggg gccgctggat gcagccaccg cgcgcagtgt ggcgctgacc     300
atctccgcct accaggagga ccccgcgtac ctgcgccagt gcctggcgtc cgcccgcgcc     360
ctgctgtacc gcgcgcgcg gctgcgcgtc tcatggtgg tggatggcaa ccgcgccgag     420
gacctctaca tggtcgacat gttccgcgag gtcttcgctg acgaggaccc cgccacgtac     480
gtgtgggacg gcaactacca ccagccctgg gaacccgcgg cggcgggcgc ggtgggcgcc     540
ggagcctatc gggaggtgga ggcggaggat cctgggcggc tggcagtgga ggcgctggtg     600
aggactcgca ggtgcgtgtg cgtggcgcag cgctggggcg gcaagcgcga ggtcatgtac     660
acagccttca ggcgctcggg agattcggtg gactacgtgc aggtctgtga ctcggacaca     720
aggttggacc ccatggcact gctggagctc gtgcgggtac tggacgagga ccccgggta     780
```

-continued

```
ggggctgttg gtggggacgt gcggatcctt aaccctctgg actcctgggt cagcttccta      840
agcagcctgc gatactgggt agccttcaat gtggagcggg cttgtcagag ctacttccac      900
tgtgtatcct gcatcagcgg ttctctaggt acacctccag gtcccgctgc tactcagaga      960
cgccctcgtc cttcctgcgg tggctgagcc agcagacacg ctggtccaag tcgtacttcc     1020
gtgagtggct gtacaacgcg ctctggtggc accggcacca tgcgtggatg a             1071
```

<210> SEQ ID NO 4
<211> LENGTH: 376
<212> TYPE: PRT
<213> ORGANISM: Homo sapiens

<400> SEQUENCE: 4

```
Met Arg Gln Gln Asp Ala Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
        35                  40                  45

Asp Arg Tyr Gly Leu Leu Ala Phe Gly Leu Tyr Gly Ala Phe Leu Ser
    50                  55                  60

Ala His Leu Val Ala Gln Ser Leu Phe Ala Tyr Leu Glu His Arg Arg
65                  70                  75                  80

Val Ala Ala Ala Arg Gly Pro Leu Asp Ala Ala Thr Ala Arg Ser
            85                  90                  95

Val Ala Leu Thr Ile Ser Ala Tyr Gln Glu Asp Pro Ala Tyr Leu Arg
            100                 105                 110

Gln Cys Leu Ala Ser Ala Arg Ala Leu Leu Tyr Pro Arg Ala Arg Leu
        115                 120                 125

Arg Val Leu Met Val Val Asp Gly Asn Arg Ala Glu Asp Leu Tyr Met
    130                 135                 140

Val Asp Met Phe Arg Glu Val Phe Ala Asp Glu Pro Ala Thr Tyr
145                 150                 155                 160

Val Trp Asp Gly Asn Tyr His Gln Pro Trp Glu Pro Ala Ala Gly
                165                 170                 175

Ala Val Gly Ala Gly Ala Tyr Arg Glu Val Ala Glu Asp Pro Gly
            180                 185                 190

Arg Leu Ala Val Glu Ala Leu Val Arg Thr Arg Arg Cys Val Cys Val
        195                 200                 205

Ala Gln Arg Trp Gly Gly Lys Arg Glu Val Met Tyr Thr Ala Phe Lys
    210                 215                 220

Ala Leu Gly Asp Ser Val Asp Tyr Val Gln Val Cys Asp Ser Asp Thr
225                 230                 235                 240

Arg Leu Asp Pro Met Ala Leu Leu Glu Leu Val Arg Val Leu Asp Glu
                245                 250                 255

Asp Pro Arg Val Gly Ala Val Gly Gly Asp Val Arg Ile Leu Asn Pro
            260                 265                 270

Leu Asp Ser Trp Val Ser Phe Leu Ser Ser Leu Arg Tyr Trp Val Ala
        275                 280                 285

Phe Asn Val Glu Arg Ala Cys Gln Ser Tyr Phe His Cys Val Ser Cys
    290                 295                 300

Ile Ser Gly Ser Leu Gly Thr Pro Pro Gly Pro Ala Ala Thr Gln Arg
305                 310                 315                 320
```

```
Arg Pro Arg Pro Ser Cys Gly Gly Ala Ser Arg His Ala Gly Pro Ser
            325                 330                 335

Arg Thr Ser Val Ser Gly Cys Thr Thr Arg Ser Gly Gly Thr Gly Thr
            340                 345                 350

Met Arg Gly Pro Thr Arg Arg Trp Ser Pro Ala Cys Ser Pro Ser Ser
            355                 360                 365

Trp Arg Pro Leu Cys Cys Val Cys
            370                 375

<210> SEQ ID NO 5
<211> LENGTH: 1083
<212> TYPE: DNA
<213> ORGANISM: Homo sapiens

<400> SEQUENCE: 5
atgagacagc aggacgcgcc caagcccact cctgcagccc gccgctgctc cggcctggcc      60
cggagggtgc tgaccatcgc cttcgccctg ctcatcctgg cctcatgac ctgggcctac     120 gccgccgggg tgccgctggc ctccgatcgc tacggcctcc tggccttcgg cctctacggg     180
gccttccttt cagcgcacct ggtggcgcag agcctcttcg cgtacctgga gcaccggcgg     240
gtggcggcgg cggcgcgggg gccgctggat gcagccaccg cgcgcagtgt ggcgctgacc     300
atctccgcct accaggagga ccccgcgtac ctgcgccagt gcctggcgtc cgcccgcgcc     360
ctgctgtacc gcgcgcgcg gctgcgcgtc tcatggtgg tggatggcaa ccgcgccgag     420
gacctctaca tggtcgacat gttccgcgag gtcttcgctg acgaggaccc cgccacgtac     480
gtgtgggacg gcaactacca ccagccctgg gaacccgcgg cggcgggcgc ggtgggcgcc     540
ggagcctatc gggaggtgga ggcggaggat cctgggcggc tggcagtgga ggcgctggtg     600
aggactcgca ggtgcgtgtg cgtggcgcag cgctggggcg gcaagcgcga ggtcatgtac     660
acagccttca aggcgctcgg agattcggtg gactacgtgc aggtctgtga ctcggacaca     720
aggttggacc ccatggcact gctggagctc gtgcgggtac tggacgagga ccccgggta     780 ggggctgttg gtggggacgt gcggatcctt aaccctctgg actcctgggt cagcttccta     840
agcagcctgc gatactgggt agccttcaat gtggagcggg cttgtcagag ctacttccac     900
tgtgtatcct gcatcagcgg tcctctagaa tcctgcccag gccccaggga gcacgcgatg     960
atgccctcat tcctcgcccc cgtgcaggta cacctccagg tcccgctgct actcagagac    1020
gccctcgtcc ttcctgcggt ggctgagcca gcagacacgc tggtccaagt cgtacttccg    1080
tga                                                                  1083

<210> SEQ ID NO 6
<211> LENGTH: 360
<212> TYPE: PRT
<213> ORGANISM: Homo sapiens

<400> SEQUENCE: 6

Met Arg Gln Gln Asp Ala Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
            35                  40                  45

Asp Arg Tyr Gly Leu Leu Ala Phe Gly Leu Tyr Gly Ala Phe Leu Ser
            50                  55                  60

Ala His Leu Val Ala Gln Ser Leu Phe Ala Tyr Leu Glu His Arg Arg
```

```
                65                  70                  75                  80
Val Ala Ala Ala Ala Arg Gly Pro Leu Asp Ala Thr Ala Arg Ser
                85                  90                  95
Val Ala Leu Thr Ile Ser Ala Tyr Gln Glu Asp Pro Ala Tyr Leu Arg
                100                 105                 110
Gln Cys Leu Ala Ser Ala Arg Ala Leu Leu Tyr Pro Arg Ala Arg Leu
                115                 120                 125
Arg Val Leu Met Val Val Asp Gly Asn Arg Ala Glu Asp Leu Tyr Met
                130                 135                 140
Val Asp Met Phe Arg Glu Val Phe Ala Asp Glu Asp Pro Ala Thr Tyr
145                 150                 155                 160
Val Trp Asp Gly Asn Tyr His Gln Pro Trp Glu Pro Ala Ala Gly
                165                 170                 175
Ala Val Gly Ala Gly Ala Tyr Arg Glu Val Glu Ala Glu Asp Pro Gly
                180                 185                 190
Arg Leu Ala Val Glu Ala Leu Val Arg Thr Arg Arg Cys Val Cys Val
                195                 200                 205
Ala Gln Arg Trp Gly Gly Lys Arg Glu Val Met Tyr Thr Ala Phe Lys
                210                 215                 220
Ala Leu Gly Asp Ser Val Asp Tyr Val Gln Val Cys Asp Ser Asp Thr
225                 230                 235                 240
Arg Leu Asp Pro Met Ala Leu Glu Leu Val Arg Val Leu Asp Glu
                245                 250                 255
Asp Pro Arg Val Gly Ala Val Gly Gly Asp Val Arg Ile Leu Asn Pro
                260                 265                 270
Leu Asp Ser Trp Val Ser Phe Leu Ser Ser Leu Arg Tyr Trp Val Ala
                275                 280                 285
Phe Asn Val Glu Arg Ala Cys Gln Ser Tyr Phe His Cys Val Ser Cys
                290                 295                 300
Ile Ser Gly Pro Leu Glu Ser Cys Pro Gly Pro Arg Glu His Ala Met
305                 310                 315                 320
Met Pro Ser Phe Leu Ala Pro Val Gln Val His Leu Gln Val Pro Leu
                325                 330                 335
Leu Leu Arg Asp Ala Leu Val Leu Pro Ala Val Ala Glu Pro Ala Asp
                340                 345                 350
Thr Leu Val Gln Val Val Leu Pro
                355                 360

<210> SEQ ID NO 7
<211> LENGTH: 1065
<212> TYPE: DNA
<213> ORGANISM: Homo sapiens

<400> SEQUENCE: 7
atgagacagc aggacgcgcc caagcccact cctgcagccc gccgctgctc cggcctggcc      60
cggagggtgc tgaccatcgc cttcgccctg ctcatcctgg gcctcatgac ctgggcctac     120
gccgccgggg tgccgctggc ctccgatcgc tacggcctcc tggccttcgg cctctacggg     180
gccttccttt cagcgcacct ggtggcgcag agcctcttcg cgtacctgga gcaccggcgg     240
gtggcggcgg cggcgggggg gccgctggat gcagccaccg cgcgcagtgt ggcgctgacc     300
atctccgcct accaggagga ccccgcgtac ctgcgccagt gcctggcgtc gcccgcgcc     360 ctgctgtacc cgcgcgcgcg gctgcgcgtc tcatggtgg tggatggcaa ccgcgccgag     420
gacctctaca tggtcgacat gttccgcgag gtcttcgctg acgaggaccc cgccacgtac     480
```

```
gtgtgggacg gcaactacca ccagccctgg gaacccgcgg cggcgggcgc ggtgggcgcc      540
ggagcctatc gggaggtgga ggcggaggat cctgggcggc tggcagtgga ggcgctggtg      600
aggactcgca ggtgcgtgtg cgtggcgcag cgctggggcg gcaagcgcga ggtcatgtac      660
acagccttca aggcgctcgg agattcggtg gactacgtgc aggtctgtga ctcggacaca      720
aggttggacc ccatggcact gctggagctc gtgcgggtac tggacgagga ccccgggta       780 ggggctgttg gtggggacgt gcggatcctt aaccctctgg actcctgggt cagcttccta      840
agcagcctgc gatactgggt agccttcaat gtggagcggg cttgtcagag ctacttccac      900
tgtgtatcct gcatcagcgg tcctctaggc ctatatagga ataacctctt gcagcagttt      960
cttgaggcct ggtacaacca gaagttcctg ggtacccact gtactttggg ggatgaccgg     1020
cacctcacca accgcatgct cagcatgggt tatgctacca agtaa                     1065
```

<210> SEQ ID NO 8
<211> LENGTH: 320
<212> TYPE: PRT
<213> ORGANISM: Homo sapiens

<400> SEQUENCE: 8

```
Ala Phe Leu Ser Ala His Leu Val Ala Gln Ser Leu Phe Ala Tyr Leu
1               5                   10                  15

Glu His Arg Arg Val Ala Ala Ala Arg Gly Pro Leu Asp Ala Ala
            20                  25                  30

Thr Ala Arg Ser Val Ala Leu Thr Ile Ser Ala Tyr Gln Glu Asp Pro
        35                  40                  45

Ala Tyr Leu Arg Gln Cys Leu Ala Ser Ala Arg Ala Leu Leu Tyr Pro
    50                  55                  60

Arg Ala Arg Leu Arg Val Leu Met Val Val Asp Gly Asn Arg Ala Glu
65                  70                  75                  80

Asp Leu Tyr Met Val Asp Met Phe Arg Glu Val Phe Ala Asp Glu Asp
                85                  90                  95

Pro Ala Thr Tyr Val Trp Asp Gly Asn Tyr His Gln Pro Trp Glu Pro
            100                 105                 110

Ala Ala Ala Gly Ala Val Gly Ala Gly Ala Tyr Arg Glu Val Glu Ala
        115                 120                 125

Glu Asp Pro Gly Arg Leu Ala Val Glu Ala Leu Val Arg Thr Arg Arg
    130                 135                 140

Cys Val Cys Val Ala Gln Arg Trp Gly Gly Lys Arg Glu Val Met Tyr
145                 150                 155                 160

Thr Ala Phe Lys Ala Leu Gly Asp Ser Val Asp Tyr Val Gln Val Cys
                165                 170                 175

Asp Ser Asp Thr Arg Leu Asp Pro Met Ala Leu Leu Glu Leu Val Arg
            180                 185                 190

Val Leu Asp Glu Asp Pro Arg Val Gly Ala Val Gly Gly Asp Val Arg
        195                 200                 205

Ile Leu Asn Pro Leu Asp Ser Trp Val Ser Phe Leu Ser Ser Leu Arg
    210                 215                 220

Tyr Trp Val Ala Phe Asn Val Glu Arg Ala Cys Gln Ser Tyr Phe His
225                 230                 235                 240

Cys Val Ser Cys Ile Ser Gly Pro Leu Gly Leu Tyr Arg Asn Asn Leu
                245                 250                 255

Leu Gln Gln Phe Leu Glu Ala Trp Tyr Asn Gln Lys Phe Leu Gly Thr
            260                 265                 270
```

```
His Cys Thr Phe Gly Asp Asp Arg His Leu Thr Asn Arg Met Leu Ser
        275                 280                 285

Met Gly Tyr Ala Thr Lys Ala Glu Gly Thr Arg Trp Ser Gly Thr Pro
        290                 295                 300

Pro Gly Pro Ala Ala Thr Gln Arg Arg Pro Arg Pro Ser Cys Gly Gly
305                 310                 315                 320

<210> SEQ ID NO 9
<211> LENGTH: 20
<212> TYPE: DNA
<213> ORGANISM: Homo sapiens

<400> SEQUENCE: 9
cgggcttgtc agagctactt                                                     20

<210> SEQ ID NO 10
<211> LENGTH: 20
<212> TYPE: DNA
<213> ORGANISM: Homo sapiens

<400> SEQUENCE: 10
agggcgtctc tgagtagcag                                                     20

<210> SEQ ID NO 11
<211> LENGTH: 20
<212> TYPE: DNA
<213> ORGANISM: Homo sapiens

<400> SEQUENCE: 11
gcctcatctg tggagatggt                                                     20

<210> SEQ ID NO 12
<211> LENGTH: 20
<212> TYPE: DNA
<213> ORGANISM: Homo sapiens

<400> SEQUENCE: 12
tcccagaggt ccactaatgc                                                     20

<210> SEQ ID NO 13
<211> LENGTH: 20
<212> TYPE: DNA
<213> ORGANISM: Homo sapiens

<400> SEQUENCE: 13
catccaggtg tgcgactctg                                                     20

<210> SEQ ID NO 14
<211> LENGTH: 20
<212> TYPE: DNA
<213> ORGANISM: Homo sapiens

<400> SEQUENCE: 14
cgctgctcag gaaggaaatc                                                     20
```